(12) United States Patent
Cameron et al.

(10) Patent No.: US 7,167,801 B2
(45) Date of Patent: Jan. 23, 2007

(54) METHOD OF IDENTIFYING POTENTIAL INHIBITORS OF HUMAN PAPILLOMAVIRUS PROTEIN E2 USING X-RAY ATOMIC COORDINATES

(75) Inventors: Dale R. Cameron, Richmond (CA); Jacques Archambault, Rosemere (CA); Christiane Yoakim, Laval (CA); Peter White, Montreal (CA); Yong Wang, Carmel, IN (US)

(73) Assignee: Boehringer Ingelheim (Canada) Ltd., Laval (CA)

( * ) Notice: Subject to any disclaimer, the term of this patent is extended or adjusted under 35 U.S.C. 154(b) by 417 days.

(21) Appl. No.: 10/193,460

(22) Filed: Jul. 11, 2002

(65) Prior Publication Data

US 2003/0082769 A1    May 1, 2003

Related U.S. Application Data

(60) Provisional application No. 60/304,412, filed on Jul. 12, 2001.

(51) Int. Cl.
G06F 7/58    (2006.01)
(52) U.S. Cl. ........................................ 702/11
(58) Field of Classification Search ............... None
See application file for complete search history.

(56) References Cited

U.S. PATENT DOCUMENTS 5,620,849 A    4/1997    Botchan et al.

FOREIGN PATENT DOCUMENTS

| EP | 0 969 013 A | 1/2000 |
|---|---|---|
| WO | WO-99-57283 A1 | 11/1999 |
| WO | WO 01/21645 A | 3/2001 |
| WO | WO 02/50082 A | 6/2002 |

OTHER PUBLICATIONS

Sedman, Juhan et al; Co-Operative interaction between the initiator E1 and the transcriptional activator E2 is required for replicator specific DNA replication of bovine papillomavirus in vivo and in vitro; The EMBO Journal; 1995; V. 14; No. 24; 6218-6228.
McBride, Alison A. et al; The Papillomavirus E2 Regulatory Proteins; The Journal of Biological Chemistry; 1991; V. 266; No. 28; 18411-18414.
Seo, Yeon-Soo et al; Bovine papilloma virus (BPV)-encoded E2 protein enhances binding of E1 protein to the BPV replication origin; PNAS; 1993; V. 90: 2865-2869.
LeMaster, David M. et al; 1H-15N Heternuclear NMR Studies of *Escherichia coli* Thioredoxin in Samples Isotopically Labeled by Residue Type: Biochemistry; 1985; V. 24; 7263-7268.
Sakai, Hiroyuki et al; Targeted Mutagenesis of the Human Papillmavirus Type 16 E2 Transactivation Domain Reveals Separable Transcriptional Activation and DNA Replication Functions; Journal of Virology; 1996; 1602-1611.

Beutner, Karl R. et al; Therapeutic Approaches to Genital Warts; The American Journal of Medicine: 1997; V. 102 (5A): 28-37.
Hughes, Fiona J. et al; E1 protein of human papillomavirus is a DNA helicase/ATPase; Nucleic Acids Research; 1993; V. 21, No. 25; 5817-5823.
Clark, Paul R. et al; A novel drug screening assay for papillomavirus specific antiviral activity; Antiviral Research: 1998; V. 37: 97-106.
Hajduk, Philip J. et al: NMR-Based Discovery of Lead Inhibitors That Block DNA Binding of the Human Papillomavirus E2 Protein; J. Med. Chem; 1997; V. 40; 3144-3150.
Cowsert, Lex M. et al; In Vitro Evaluation of Phosphorothioate Oligonucleotides Targeted to the E2 mRNA of Papillomavirus: Potential Treatment for Genital Warts; Antimicrobial Agents and Chemotherapy; 1993; 171-177.
Liu, Jen-Sing et al; The Functions fo Human Papillomavirus Type II E1, E2 and E2C Proteins in Cerfree DNA Replication. The Journal of Biological Chemistry 1995. V 270, No. 45, 27283-27291.
Mohr, Ian J. et al; Targeting the E1 Replication Protein to the Papillomavirus Origin of Replication by Complex Formation with the E2 Transactivator; Science; 1990; V. 250; 1694-1699.
Harris, Seth F. et al; Crystal Structure of the Human Papillomavirus Type 18 E2 Activation Domain; Science: 1999; V. 284; 1673-1677.
Antson, Alfred A. et al; Structure of the intact transactivation domain of the human papillomavirus E2 protein; Nature; 2000; V. 403; 805-809.
Kreider, John W. et al; Preclinical System for Evaluating Topical Podofilox Treatment of Papillomas: Dose-Response and Duration of Growth Prior to Treatment; The Journal of Investigative Dermatology; 1992; V. 99; 813-818.
McKay, R.D.G.; Binding to Simian Virus 40 T Antigen-related Protein to DNA; J. Mol. Biol.; 1981; V. 145;471-488.

(Continued)

*Primary Examiner*—Kathleen M. Kerr
*Assistant Examiner*—Suzanne M. Noakes
(74) *Attorney, Agent, or Firm*—Michael P. Morris; Mary Ellen Devlin; David A. Dow

(57) ABSTRACT

A crystallizable composition, comprising an human papillomavirus (HPV-11) E2 transactivation domain (TAD)-like polypeptide of SEQ ID NO. 2 complexed with an inhibitor L (sodium (2R,3R,4S,5R)-5-(3,4-dichlorophenyl)-5'-methyl-1',3'-dioxo-4-({[4-(1,2,3-thiadiazol-4-yl)phenyl]amino}carbonyl)-1',3',4,5-tetrahydro-3H-spiro[furan-2,2'-indene]-3-carboxylate). The invention also provides a method for producing the crystallized HPV E2 TAD-inhibitor complex (HPV E2 TAD-L) comprising: a) mixing purified HPV E2 TAD, contained in a purification buffer, with solublized inhibitor L to generate a complex solution containing the HPV E2 TAD-L complex; and b) crystallizing the complex from a) in a crystallization buffer. The invention also provides a method for producing crystallized apo HPV E2 TAD, comprising: a) mixing apo HPV E2 TAD, contained in a purification buffer, with a crystallization buffer.

Figure 2:
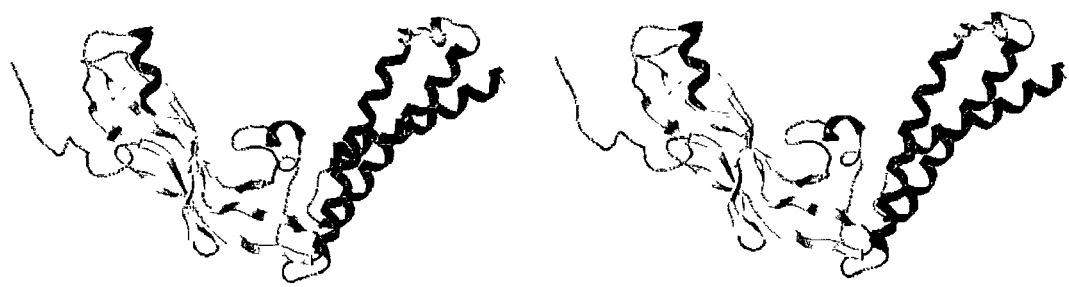
Figure 3:
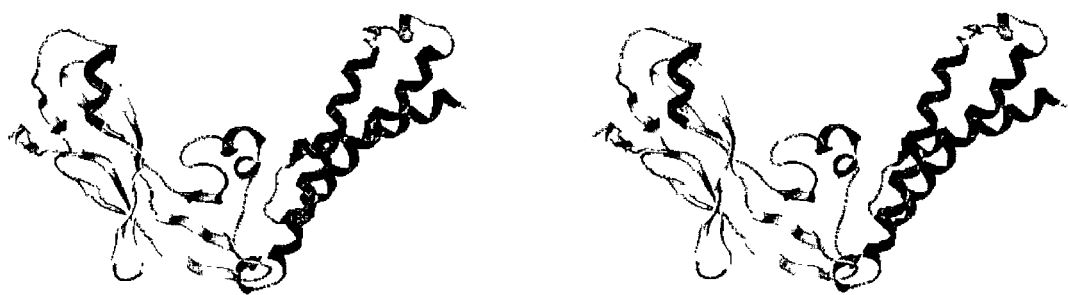
Figure 4:
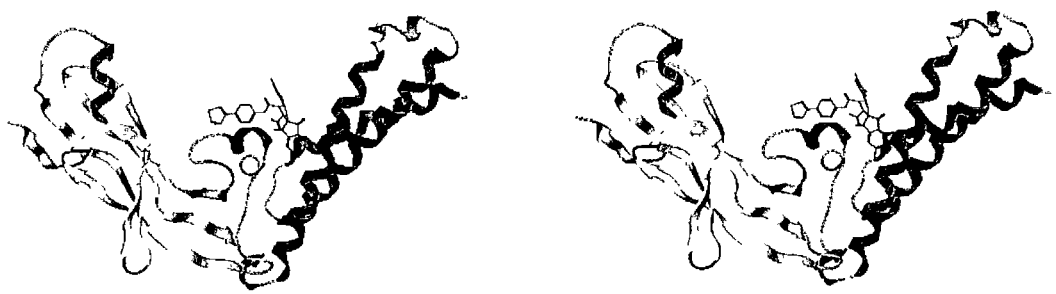

X-ray crystal structure coordinates the HPV E2 TAD-L complex, are also provided, which define an inhibitor binding pocket. The inhibitor binding pocket is useful for screening potential small molecule inhibitors that bind to the pocket that may be inhibitors of papillomavirus infection.

3 Claims, 38 Drawing Sheets

OTHER PUBLICATIONS

Bailey, S. (CCP4 Secretary); The CCP4 Suite: Programs for Protein Crystallography; Acta Cryst.; 1994: D50: 760-763.

Chiang, Cheng-Ming et al; Viral E1 and E2 proteins support replication of homologous and heterologous papillomavirus origins; PNAS: 1992; V. 89; 5799-5803.

Kuo, Shu-Ru: Cell-Free Replication of the Human Papillomavirus DNA with Homologous Viral E1 and E2 Proteins and Human Cell Extracts: The Journal of Biological Chemistry; 1994; V. 269; N. 39; 24058-24065.

Lehninger, A.L.; The Molecular Basis of Cell Structure and Function; Biochemistry; 2nd edition; 1975; Chapter 4; pp. 73-75; Woth Publisher's Inc.; New York, N.Y.

Dayhoff, M.O.; 23 Matrices for Detecting Distant Relationships; Atlas of Protein Sequence and Structure; V. 5; Suppl.3; 1978; pp. 353-358; National Biochemical Research Foundation; Washington, D.C.

Kim, Seung-Sup, et al.; The Structural Basis of DNA Target Discrimination by Papillomavirus E2 Proteins; The Journal of Biological Chemistry, vol. 275, No. 40, Oct. 6, 2000, pp. 31245-31254.

Gauthier, Jean-Michel, et al.; Two DNA-Bound E2 Dimers are Required for Strong Transcriptional Activation and for Cooperation with Cellular Factors in Most Cells; The New Biologist, vol. 3, No. 5 May 1991, pp. 498-509.

Wang, Y., et al. "Crystal Structure of the E2 Transactivation Domain of Human Papillomavirus Type 11 Bound to a Protein Interaction Inhibitor", The Journal of Biological Chemistry, vol. 279, No. 8, 2004, p6976-6985 XP002390791.

FIGURE 1A

SEQ ID NO. 1

HPV11 E2 1-220 (maximal TAD, range used in Sakai, et al. J Virol. V70 1602-11 (96))

1...

MEAIAKRLDA CQDQLLELYE ENSIDIHKHI MHWKCIRLES VLLHKAKQMG LSHIGLQVVP
PLTVSETKGH NAIEMQMHLE SLAKTQYGVE PWTLQDTSYE MWLTPPKRCF KKQGNTVEVK
FDGCEDNVME YVVWTHIYLQ DNDSWVKVTS SVDAKGIYYT CGQFKTYYVN FNKEAQKYGS
TNHWEVCYGS TVICSPASVS STVREVSIAE PTTYTPAQTT

...220

FIGURE 1B

SEQ ID NO.2

AMINO ACID SEQUENCE of E2 TAD FROM HPV-11 USED FOR CRYSTALLIZATION OF THE PROTEIN-COMPOUND L COMPLEX 1          2...

(GHHHHHH)EAI AKRLDACQDQ LLELYEENSI DIHKHIMHWK CIRLESVLLH
KAKQMGLSHI GLQVVPPLTV SETKGHNAIE MQMHLESLAK TQYGVEPWTL
QDTSYEMWLT PPKRCFKKQG NTVEVKFDGC EDNVMEYVVW THIYLQDNDS
WVKVTSSVDA KGIYYTCGQF KTYYVNFNKE AQKYGSTNHW EVCYGSTVIC
SPASVSS (KKKK)

...201

- Y19 and H32: Open up the pocket

- Y19 all-atom rms = 1.959 Å,
  Main chain rms = 0.618 Å
  - $\chi^1$ changes 85° $\chi^2$ changes ~40°
  - Large rotation moves ring out

- H32 all-atom rms = 0.704 Å,
  Main chain rms = 0.063 Å
  - $\chi^1$ changes 0.6° $\chi^2$ changes ~90°
  - Imidazole ring portion rotates

|      |    |     | A.A. |    | X      | Y       | Z       | Occ. | B     | Chain | Element |
|------|----|-----|------|----|--------|---------|---------|------|-------|-------|---------|
| ATOM | 1  | CB  | ALA  | 2  | 69.219 | -15.638 | -12.012 | 1.00 | 76.46 | A     | C       |
| ATOM | 2  | C   | ALA  | 2  | 69.280 | -13.178 | -12.483 | 1.00 | 76.11 | A     | C       |
| ATOM | 3  | O   | ALA  | 2  | 69.740 | -13.020 | -11.347 | 1.00 | 76.56 | A     | O       |
| ATOM | 4  | N   | ALA  | 2  | 68.992 | -14.822 | -14.346 | 1.00 | 76.54 | A     | N       |
| ATOM | 5  | CA  | ALA  | 2  | 68.690 | -14.517 | -12.914 | 1.00 | 76.36 | A     | C       |
| ATOM | 6  | N   | ALA  | 3  | 69.274 | -12.214 | -13.392 | 1.00 | 75.51 | A     | N       |
| ATOM | 7  | CA  | ALA  | 3  | 69.793 | -10.890 | -13.069 | 1.00 | 75.25 | A     | C       |
| ATOM | 8  | CB  | ALA  | 3  | 70.173 | -10.141 | -14.354 | 1.00 | 75.07 | A     | C       |
| ATOM | 9  | C   | ALA  | 3  | 68.700 | -10.132 | -12.315 | 1.00 | 74.59 | A     | C       |
| ATOM | 10 | O   | ALA  | 3  | 68.943 | -9.071  | -11.742 | 1.00 | 74.61 | A     | O       |
| ATOM | 11 | N   | ILE  | 4  | 67.501 | -10.709 | -12.310 | 1.00 | 73.75 | A     | N       |
| ATOM | 12 | CA  | ILE  | 4  | 66.337 | -10.113 | -11.664 | 1.00 | 73.48 | A     | C       |
| ATOM | 13 | CB  | ILE  | 4  | 65.096 | -11.032 | -11.831 | 1.00 | 73.52 | A     | C       |
| ATOM | 14 | CG2 | ILE  | 4  | 65.122 | -12.154 | -10.809 | 1.00 | 73.29 | A     | C       |
| ATOM | 15 | CG1 | ILE  | 4  | 63.819 | -10.209 | -11.686 | 1.00 | 73.74 | A     | C       |
| ATOM | 16 | CD1 | ILE  | 4  | 63.641 | -9.181  | -12.781 | 1.00 | 74.09 | A     | C       |
| ATOM | 17 | C   | ILE  | 4  | 66.526 | -9.775  | -10.179 | 1.00 | 72.84 | A     | C       |
| ATOM | 18 | O   | ILE  | 4  | 66.096 | -8.717  | -9.728  | 1.00 | 72.83 | A     | O       |
| ATOM | 19 | N   | ALA  | 5  | 67.172 | -10.663 | -9.425  | 1.00 | 72.37 | A     | N       |
| ATOM | 20 | CA  | ALA  | 5  | 67.402 | -10.440 | -7.994  | 1.00 | 71.55 | A     | C       |
| ATOM | 21 | CB  | ALA  | 5  | 67.905 | -11.712 | -7.339  | 1.00 | 71.52 | A     | C       |
| ATOM | 22 | C   | ALA  | 5  | 68.385 | -9.304  | -7.743  | 1.00 | 70.92 | A     | C       |
| ATOM | 23 | O   | ALA  | 5  | 68.138 | -8.441  | -6.904  | 1.00 | 70.71 | A     | O       |
| ATOM | 24 | N   | LYS  | 6  | 69.508 | -9.309  | -8.457  | 1.00 | 70.37 | A     | N       |
| ATOM | 25 | CA  | LYS  | 6  | 70.495 | -8.247  | -8.301  | 1.00 | 69.87 | A     | C       |
| ATOM | 26 | CB  | LYS  | 6  | 71.693 | -8.439  | -9.243  | 1.00 | 70.91 | A     | C       |
| ATOM | 27 | CG  | LYS  | 6  | 72.708 | -9.515  | -8.853  | 1.00 | 72.11 | A     | C       |
| ATOM | 28 | CD  | LYS  | 6  | 74.089 | -9.161  | -9.444  | 1.00 | 73.12 | A     | C       |
| ATOM | 29 | CE  | LYS  | 6  | 75.130 | -10.262 | -9.238  | 1.00 | 74.05 | A     | C       |
| ATOM | 30 | NZ  | LYS  | 6  | 74.864 | -11.451 | -10.115 | 1.00 | 74.63 | A     | N       |
| ATOM | 31 | C   | LYS  | 6  | 69.835 | -6.916  | -8.636  | 1.00 | 68.76 | A     | C       |
| ATOM | 32 | O   | LYS  | 6  | 70.147 | -5.896  | -8.032  | 1.00 | 68.67 | A     | O       |
| ATOM | 33 | N   | ARG  | 7  | 68.929 | -6.931  | -9.610  | 1.00 | 67.48 | A     | N       |
| ATOM | 34 | CA  | ARG  | 7  | 68.240 | -5.715  | -10.011 | 1.00 | 66.34 | A     | C       |
| ATOM | 35 | CB  | ARG  | 7  | 67.539 | -5.902  | -11.357 | 1.00 | 67.61 | A     | C       |
| ATOM | 36 | CG  | ARG  | 7  | 68.435 | -5.656  | -12.555 | 1.00 | 69.82 | A     | C       |
| ATOM | 37 | CD  | ARG  | 7  | 68.961 | -4.223  | -12.573 | 1.00 | 71.83 | A     | C       |
| ATOM | 38 | NE  | ARG  | 7  | 69.811 | -3.990  | -13.739 | 1.00 | 74.26 | A     | N       |
| ATOM | 39 | CZ  | ARG  | 7  | 70.534 | -2.891  | -13.944 | 1.00 | 74.98 | A     | C       |
| ATOM | 40 | NH1 | ARG  | 7  | 71.274 | -2.784  | -15.042 | 1.00 | 75.99 | A     | N       |
| ATOM | 41 | NH2 | ARG  | 7  | 70.524 | -1.903  | -13.057 | 1.00 | 75.62 | A     | N       |
| ATOM | 42 | C   | ARG  | 7  | 67.233 | -5.255  | -8.979  | 1.00 | 64.58 | A     | C       |
| ATOM | 43 | O   | ARG  | 7  | 67.078 | -4.056  | -8.762  | 1.00 | 64.20 | A     | O       |
| ATOM | 44 | N   | LEU  | 8  | 66.549 | -6.205  | -8.349  | 1.00 | 62.83 | A     | N       |
| ATOM | 45 | CA  | LEU  | 8  | 65.561 | -5.882  | -7.329  | 1.00 | 61.70 | A     | C       |
| ATOM | 46 | CB  | LEU  | 8  | 64.695 | -7.099  | -7.009  | 1.00 | 61.40 | A     | C       |
| ATOM | 47 | CG  | LEU  | 8  | 63.592 | -6.762  | -5.998  | 1.00 | 61.65 | A     | C       |
| ATOM | 48 | CD1 | LEU  | 8  | 62.565 | -5.835  | -6.668  | 1.00 | 61.23 | A     | C       |
| ATOM | 49 | CD2 | LEU  | 8  | 62.916 | -8.032  | -5.497  | 1.00 | 61.52 | A     | C       |
| ATOM | 50 | C   | LEU  | 8  | 66.224 | -5.382  | -6.042  | 1.00 | 61.18 | A     | C       |
| ATOM | 51 | O   | LEU  | 8  | 65.795 | -4.386  | -5.456  | 1.00 | 60.93 | A     | O       |
| ATOM | 52 | N   | ASP  | 9  | 67.267 | -6.077  | -5.601  | 1.00 | 60.54 | A     | N       |
| ATOM | 53 | CA  | ASP  | 9  | 67.984 | -5.680  | -4.397  | 1.00 | 59.85 | A     | C       |

Figure 9-1

```
ATOM   54  CB   ASP   9    69.116  -6.662  -4.094 1.00 61.48    A  C
ATOM   55  CG   ASP   9    69.950  -6.234  -2.890 1.00 63.72    A  C
ATOM   56  OD1  ASP   9    69.441  -6.312  -1.745 1.00 65.15    A  O
ATOM   57  OD2  ASP   9    71.112  -5.805  -3.084 1.00 64.96    A  O
ATOM   58  C    ASP   9    68.569  -4.285  -4.577 1.00 58.31    A  C
ATOM   59  O    ASP   9    68.719  -3.537  -3.610 1.00 58.44    A  O
ATOM   60  N    ALA  10    68.898   3.938  -5.817 1.00 56.38    A  N
ATOM   61  CA   ALA  10    69.467  -2.634  -6.113 1.00 55.05    A  C
ATOM   62  CB   ALA  10    70.180  -2.662  -7.451 1.00 54.97    A  C
ATOM   63  C    ALA  10    68.389  -1.565  -6.123 1.00 54.14    A  C
ATOM   64  O    ALA  10    68.642  -0.409  -5.771 1.00 54.31    A  O
ATOM   65  N    CYS  11    67.187  -1.958  -6.525 1.00 52.95    A  N
ATOM   66  CA   CYS  11    66.056  -1.044  -6.581 1.00 52.55    A  C
ATOM   67  CB   CYS  11    64.939  -1.674  -7.416 1.00 52.53    A  C
ATOM   68  SG   CYS  11    63.393  -0.743  -7.506 1.00 54.92    A  S
ATOM   69  C    CYS  11    65.557  -0.721  -5.161 1.00 51.97    A  C
ATOM   70  O    CYS  11    65.313   0.439  -4.814 1.00 50.67    A  O
ATOM   71  N    GLN  12    65.426  -1.758  -4.340 1.00 52.15    A  N
ATOM   72  CA   GLN  12    64.961  -1.584  -2.972 1.00 52.03    A  C
ATOM   73  CB   GLN  12    64.634  -2.938  -2.363 1.00 51.18    A  C
ATOM   74  CG   GLN  12    63.529  -3.578  -3.150 1.00 51.12    A  C
ATOM   75  CD   GLN  12    63.082  -4.905  -2.606 1.00 50.78    A  C
ATOM   76  OE1  GLN  12    63.900  -5.754  -2.239 1.00 51.27    A  O
ATOM   77  NE2  GLN  12    61.770  -5.109  -2.577 1.00 49.59    A  N
ATOM   78  C    GLN  12    65.974  -0.832  -2.141 1.00 52.24    A  C
ATOM   79  O    GLN  12    65.602  -0.117  -1.212 1.00 52.22    A  O
ATOM   80  N    ASP  13    67.252  -0.967  -2.484 1.00 52.39    A  N
ATOM   81  CA   ASP  13    68.280  -0.239  -1.754 1.00 52.75    A  C
ATOM   82  CB   ASP  13    69.668  -0.713  -2.157 1.00 54.64    A  C
ATOM   83  CG   ASP  13    70.636  -0.676  -1.002 1.00 57.09    A  C
ATOM   84  OD1  ASP  13    70.439  -1.463  -0.044 1.00 58.19    A  O
ATOM   85  OD2  ASP  13    71.584   0.146  -1.043 1.00 59.05    A  O
ATOM   86  C    ASP  13    68.127   1.248  -2.054 1.00 52.11    A  C
ATOM   87  O    ASP  13    68.239   2.088  -1.164 1.00 52.48    A  O
ATOM   88  N    GLN  14    67.845   1.564  -3.314 1.00 51.25    A  N
ATOM   89  CA   GLN  14    67.643   2.942  -3.755 1.00 50.51    A  C
ATOM   90  CB   GLN  14    67.405   2.962  -5.266 1.00 52.25    A  C
ATOM   91  CG   GLN  14    68.094   4.090  -6.007 1.00 55.34    A  C
ATOM   92  CD   GLN  14    68.709   3.606  -7.324 1.00 57.48    A  C
ATOM   93  OE1  GLN  14    69.408   4.359  -8.015 1.00 58.25    A  O
ATOM   94  NE2  GLN  14    68.450   2.339  -7.672 1.00 57.77    A  N
ATOM   95  C    GLN  14    66.419   3.513  -3.029 1.00 49.12    A  C
ATOM   96  O    GLN  14    66.445   4.650  -2.561 1.00 48.46    A  O
ATOM   97  N    LEU  15    65.350   2.716  -2.952 1.00 47.83    A  N
ATOM   98  CA   LEU  15    64.132   3.127  -2.262 1.00 47.01    A  C
ATOM   99  CB   LEU  15    63.079   2.011  -2.297 1.00 45.61    A  C
ATOM  100  CG   LEU  15    62.408   1.846  -3.667 1.00 45.40    A  C
ATOM  101  CD1  LEU  15    61.702   0.500  -3.762 1.00 44.37    A  C
ATOM  102  CD2  LEU  15    61.454   3.014  -3.899 1.00 44.15    A  C
ATOM  103  C    LEU  15    64.482   3.467  -0.831 1.00 47.02    A  C
ATOM  104  O    LEU  15    64.105   4.524  -0.323 1.00 46.54    A  O
ATOM  105  N    LEU  16    65.234   2.585  -0.190 1.00 47.75    A  N
ATOM  106  CA   LEU  16    65.620   2.834   1.178 1.00 49.61    A  C
ATOM  107  CB   LEU  16    66.452   1.683   1.721 1.00 50.53    A  C
ATOM  108  CG   LEU  16    66.740   1.796   3.223 1.00 50.64    A  C
ATOM  109  CD1  LEU  16    65.432   2.048   3.995 1.00 49.34    A  C
ATOM  110  CD2  LEU  16    67.424   0.503   3.694 1.00 50.83    A  C
```

Figure 9-2

| | | | | | | | | | | | |
|---|---|---|---|---|---|---|---|---|---|---|---|
| ATOM | 111 | C | LEU | 16 | 66.419 | 4.126 | 1.255 | 1.00 | 50.90 | A | C |
| ATOM | 112 | O | LEU | 16 | 66.234 | 4.922 | 2.173 | 1.00 | 50.88 | A | O |
| ATOM | 113 | N | GLU | 17 | 67.292 | 4.338 | 0.275 | 1.00 | 52.21 | A | N |
| ATOM | 114 | CA | GLU | 17 | 68.108 | 5.548 | 0.219 | 1.00 | 53.50 | A | C |
| ATOM | 115 | CB | GLU | 17 | 69.148 | 5.422 | -0.895 | 1.00 | 55.35 | A | C |
| ATOM | 116 | CG | GLU | 17 | 70.202 | 6.498 | -0.869 | 1.00 | 58.20 | A | C |
| ATOM | 117 | CD | GLU | 17 | 70.935 | 6.537 | 0.467 | 1.00 | 59.88 | A | C |
| ATOM | 118 | OE1 | GLU | 17 | 71.514 | 5.489 | 0.842 | 1.00 | 60.70 | A | O |
| ATOM | 119 | OE2 | GLU | 17 | 70.927 | 7.605 | 1.132 | 1.00 | 60.92 | A | O |
| ATOM | 120 | C | GLU | 17 | 67.262 | 6.811 | -0.003 | 1.00 | 54.02 | A | C |
| ATOM | 121 | O | GLU | 17 | 67.550 | 7.872 | 0.542 | 1.00 | 54.41 | A | O |
| ATOM | 122 | N | LEU | 18 | 66.225 | 6.701 | -0.824 | 1.00 | 53.82 | A | N |
| ATOM | 123 | CA | LEU | 18 | 65.341 | 7.836 | -1.078 | 1.00 | 53.41 | A | C |
| ATOM | 124 | CB | LEU | 18 | 64.382 | 7.514 | -2.228 | 1.00 | 52.97 | A | C |
| ATOM | 125 | CG | LEU | 18 | 65.043 | 7.389 | -3.603 | 1.00 | 53.31 | A | C |
| ATOM | 126 | CD1 | LEU | 18 | 64.085 | 6.806 | -4.645 | 1.00 | 52.42 | A | C |
| ATOM | 127 | CD2 | LEU | 18 | 65.523 | 8.772 | -4.010 | 1.00 | 53.18 | A | C |
| ATOM | 128 | C | LEU | 18 | 64.550 | 8.157 | 0.193 | 1.00 | 53.87 | A | C |
| ATOM | 129 | O | LEU | 18 | 64.302 | 9.322 | 0.522 | 1.00 | 53.42 | A | O |
| ATOM | 130 | N | TYR | 19 | 64.161 | 7.109 | 0.909 | 1.00 | 54.36 | A | N |
| ATOM | 131 | CA | TYR | 19 | 63.423 | 7.275 | 2.150 | 1.00 | 55.05 | A | C |
| ATOM | 132 | CB | TYR | 19 | 62.977 | 5.917 | 2.705 | 1.00 | 54.57 | A | C |
| ATOM | 133 | CG | TYR | 19 | 62.339 | 6.040 | 4.072 | 1.00 | 54.45 | A | C |
| ATOM | 134 | CD1 | TYR | 19 | 61.057 | 6.579 | 4.217 | 1.00 | 55.01 | A | C |
| ATOM | 135 | CE1 | TYR | 19 | 60.503 | 6.796 | 5.481 | 1.00 | 54.69 | A | C |
| ATOM | 136 | CD2 | TYR | 19 | 63.050 | 5.711 | 5.229 | 1.00 | 54.15 | A | C |
| ATOM | 137 | CE2 | TYR | 19 | 62.509 | 5.921 | 6.498 | 1.00 | 54.03 | A | C |
| ATOM | 138 | CZ | TYR | 19 | 61.235 | 6.466 | 6.615 | 1.00 | 54.95 | A | C |
| ATOM | 139 | OH | TYR | 19 | 60.696 | 6.705 | 7.860 | 1.00 | 55.20 | A | O |
| ATOM | 140 | C | TYR | 19 | 64.246 | 7.994 | 3.222 | 1.00 | 56.01 | A | C |
| ATOM | 141 | O | TYR | 19 | 63.726 | 8.838 | 3.929 | 1.00 | 55.82 | A | O |
| ATOM | 142 | N | GLU | 20 | 65.526 | 7.657 | 3.329 | 1.00 | 57.45 | A | N |
| ATOM | 143 | CA | GLU | 20 | 66.397 | 8.243 | 4.346 | 1.00 | 59.44 | A | C |
| ATOM | 144 | CB | GLU | 20 | 67.700 | 7.469 | 4.415 | 1.00 | 61.02 | A | C |
| ATOM | 145 | CG | GLU | 20 | 67.609 | 6.005 | 4.785 | 1.00 | 64.41 | A | C |
| ATOM | 146 | CD | GLU | 20 | 68.975 | 5.363 | 4.642 | 1.00 | 67.07 | A | C |
| ATOM | 147 | OE1 | GLU | 20 | 69.969 | 6.086 | 4.915 | 1.00 | 69.14 | A | O |
| ATOM | 148 | OE2 | GLU | 20 | 69.067 | 4.170 | 4.264 | 1.00 | 68.06 | A | O |
| ATOM | 149 | C | GLU | 20 | 66.756 | 9.709 | 4.123 | 1.00 | 59.87 | A | C |
| ATOM | 150 | O | GLU | 20 | 67.100 | 10.425 | 5.062 | 1.00 | 59.65 | A | O |
| ATOM | 151 | N | GLU | 21 | 66.694 | 10.141 | 2.870 | 1.00 | 60.23 | A | N |
| ATOM | 152 | CA | GLU | 21 | 67.047 | 11.499 | 2.493 | 1.00 | 60.34 | A | C |
| ATOM | 153 | CB | GLU | 21 | 66.990 | 11.617 | 0.975 | 1.00 | 62.05 | A | C |
| ATOM | 154 | CG | GLU | 21 | 67.433 | 12.952 | 0.460 | 1.00 | 64.80 | A | C |
| ATOM | 155 | CD | GLU | 21 | 67.355 | 13.027 | -1.045 | 1.00 | 66.96 | A | C |
| ATOM | 156 | OE1 | GLU | 21 | 66.250 | 12.820 | -1.599 | 1.00 | 67.88 | A | O |
| ATOM | 157 | OE2 | GLU | 21 | 68.402 | 13.288 | -1.676 | 1.00 | 68.30 | A | O |
| ATOM | 158 | C | GLU | 21 | 66.222 | 12.616 | 3.141 | 1.00 | 60.05 | A | C |
| ATOM | 159 | O | GLU | 21 | 66.762 | 13.681 | 3.464 | 1.00 | 59.32 | A | O |
| ATOM | 160 | N | ASN | 22 | 64.926 | 12.373 | 3.331 | 1.00 | 59.33 | A | N |
| ATOM | 161 | CA | ASN | 22 | 64.034 | 13.363 | 3.928 | 1.00 | 58.57 | A | C |
| ATOM | 162 | CB | ASN | 22 | 64.406 | 13.600 | 5.388 | 1.00 | 60.08 | A | C |
| ATOM | 163 | CG | ASN | 22 | 63.242 | 13.375 | 6.341 | 1.00 | 61.22 | A | C |
| ATOM | 164 | OD1 | ASN | 22 | 63.434 | 13.353 | 7.559 | 1.00 | 61.31 | A | O |
| ATOM | 165 | ND2 | ASN | 22 | 62.032 | 13.205 | 5.797 | 1.00 | 61.77 | A | N |
| ATOM | 166 | C | ASN | 22 | 64.152 | 14.670 | 3.150 | 1.00 | 57.86 | A | C |
| ATOM | 167 | O | ASN | 22 | 64.342 | 15.742 | 3.726 | 1.00 | 57.53 | A | O |

Figure 9-3

```
ATOM    168  N    SER   23      64.047  14.555   1.831  1.00 56.63      A  N
ATOM    169  CA   SER   23      64.135  15.679   0.907  1.00 55.31      A  C
ATOM    170  CB   SER   23      64.401  15.130  -0.504  1.00 55.62      A  C
ATOM    171  OG   SER   23      64.284  16.128  -1.510  1.00 56.88      A  O
ATOM    172  C    SER   23      62.854  16.516   0.892  1.00 54.41      A  C
ATOM    173  O    SER   23      61.764  16.008   1.171  1.00 54.04      A  O
ATOM    174  N    ILE   24      62.993  17.803   0.581  1.00 53.28      A  N
ATOM    175  CA   ILE   24      61.839  18.685   0.468  1.00 52.49      A  C
ATOM    176  CB   ILE   24      61.983  19.942   1.349  1.00 53.11      A  C
ATOM    177  CG2  ILE   24      62.187  19.537   2.795  1.00 53.50      A  C
ATOM    178  CG1  ILE   24      63.156  20.798   0.865  1.00 54.05      A  C
ATOM    179  CD1  ILE   24      63.216  22.168   1.519  1.00 53.59      A  C
ATOM    180  C    ILE   24      61.701  19.104  -1.003  1.00 51.26      A  C
ATOM    181  O    ILE   24      60.945  20.011  -1.336  1.00 50.75      A  O
ATOM    182  N    ASP   25      62.444  18.423  -1.871  1.00 50.30      A  N
ATOM    183  CA   ASP   25      62.441  18.692  -3.307  1.00 50.07      A  C
ATOM    184  CB   ASP   25      63.873  18.515  -3.842  1.00 50.92      A  C
ATOM    185  CG   ASP   25      63.981  18.664  -5.365  1.00 52.01      A  C
ATOM    186  OD1  ASP   25      63.058  19.225  -6.004  1.00 51.75      A  O
ATOM    187  OD2  ASP   25      65.024  18.224  -5.918  1.00 52.58      A  O
ATOM    188  C    ASP   25      61.450  17.774  -4.037  1.00 49.04      A  C
ATOM    189  O    ASP   25      61.655  16.569  -4.144  1.00 48.85      A  O
ATOM    190  N    ILE   26      60.365  18.350  -4.532  1.00 48.24      A  N
ATOM    191  CA   ILE   26      59.365  17.558  -5.224  1.00 48.06      A  C
ATOM    192  CB   ILE   26      58.269  18.454  -5.851  1.00 47.50      A  C
ATOM    193  CG2  ILE   26      58.856  19.272  -7.013  1.00 47.07      A  C
ATOM    194  CG1  ILE   26      57.097  17.568  -6.302  1.00 45.99      A  C
ATOM    195  CD1  ILE   26      55.824  18.309  -6.578  1.00 45.38      A  C
ATOM    196  C    ILE   26      59.938  16.623  -6.303  1.00 48.33      A  C
ATOM    197  O    ILE   26      59.411  15.530  -6.519  1.00 48.35      A  O
ATOM    198  N    HIS   27      61.023  17.027  -6.963  1.00 47.99      A  N
ATOM    199  CA   HIS   27      61.613  16.175  -7.997  1.00 47.56      A  C
ATOM    200  CB   HIS   27      62.659  16.956  -8.794  1.00 48.56      A  C
ATOM    201  CG   HIS   27      62.066  18.059  -9.612  1.00 49.99      A  C
ATOM    202  CD2  HIS   27      62.052  19.399  -9.424  1.00 50.47      A  C
ATOM    203  ND1  HIS   27      61.284  17.819 -10.724  1.00 50.84      A  N
ATOM    204  CE1  HIS   27      60.809  18.965 -11.182  1.00 50.91      A  C
ATOM    205  NE2  HIS   27      61.260  19.939 -10.410  1.00 51.47      A  N
ATOM    206  C    HIS   27      62.190  14.866  -7.469  1.00 46.62      A  C
ATOM    207  O    HIS   27      62.194  13.872  -8.179  1.00 46.51      A  O
ATOM    208  N    LYS   28      62.679  14.856  -6.234  1.00 45.76      A  N
ATOM    209  CA   LYS   28      63.188  13.613  -5.651  1.00 45.51      A  C
ATOM    210  CB   LYS   28      63.945  13.889  -4.352  1.00 47.34      A  C
ATOM    211  CG   LYS   28      65.416  14.194  -4.544  1.00 50.54      A  C
ATOM    212  CD   LYS   28      66.139  12.970  -5.084  1.00 53.73      A  C
ATOM    213  CE   LYS   28      67.615  13.271  -5.341  1.00 55.54      A  C
ATOM    214  NZ   LYS   28      68.308  13.665  -4.080  1.00 57.03      A  N
ATOM    215  C    LYS   28      62.022  12.653  -5.360  1.00 44.10      A  C
ATOM    216  O    LYS   28      62.154  11.433  -5.460  1.00 43.29      A  O
ATOM    217  N    HIS   29      60.872  13.214  -5.018  1.00 42.36      A  N
ATOM    218  CA   HIS   29      59.707  12.394  -4.720  1.00 41.64      A  C
ATOM    219  CB   HIS   29      58.664  13.231  -3.966  1.00 39.75      A  C
ATOM    220  CG   HIS   29      59.195  13.824  -2.699  1.00 38.81      A  C
ATOM    221  CD2  HIS   29      59.063  15.061  -2.165  1.00 38.36      A  C
ATOM    222  ND1  HIS   29      59.983  13.109  -1.819  1.00 37.80      A  N
ATOM    223  CE1  HIS   29      60.310  13.882  -0.800  1.00 37.57      A  C
ATOM    224  NE2  HIS   29      59.766  15.070  -0.986  1.00 37.81      A  N
```

Figure 9-4

```
ATOM    225  C    HIS   29      59.126  11.773  -5.995  1.00  41.39      A  C
ATOM    226  O    HIS   29      58.560  10.680  -5.955  1.00  40.64      A  O
ATOM    227  N    ILE   30      59.271  12.475  -7.117  1.00  40.70      A  N
ATOM    228  CA   ILE   30      58.809  11.971  -8.400  1.00  40.90      A  C
ATOM    229  CB   ILE   30      58.891  13.076  -9.496  1.00  40.43      A  C
ATOM    230  CG2  ILE   30      58.707  12.476 -10.890  1.00  38.88      A  C
ATOM    231  CG1  ILE   30      57.836  14.141  -9.208  1.00  39.33      A  C
ATOM    232  CD1  ILE   30      57.917  15.367 -10.091  1.00  39.37      A  C
ATOM    233  C    ILE   30      59.707  10.794  -8.766  1.00  41.60      A  C
ATOM    234  O    ILE   30      59.245   9.752  -9.223  1.00  42.31      A  O
ATOM    235  N    MET   31      60.998  10.954  -8.547  1.00  42.39      A  N
ATOM    236  CA   MET   31      61.940   9.887  -8.830  1.00  44.18      A  C
ATOM    237  CB   MET   31      63.362  10.396  -8.583  1.00  48.11      A  C
ATOM    238  CG   MET   31      64.486   9.415  -8.895  1.00  53.11      A  C
ATOM    239  SD   MET   31      66.062  10.096  -8.218  1.00  62.00      A  S
ATOM    240  CE   MET   31      67.334   8.738  -8.657  1.00  59.07      A  C
ATOM    241  C    MET   31      61.629   8.711  -7.896  1.00  43.29      A  C
ATOM    242  O    MET   31      61.792   7.539  -8.254  1.00  43.65      A  O
ATOM    243  N    HIS   32      61.186   9.029  -6.687  1.00  41.63      A  N
ATOM    244  CA   HIS   32      60.870   7.991  -5.717  1.00  40.79      A  C
ATOM    245  CB   HIS   32      60.581   8.627  -4.354  1.00  40.22      A  C
ATOM    246  CG   HIS   32      60.660   7.666  -3.219  1.00  40.19      A  C
ATOM    247  CD2  HIS   32      60.590   6.314  -3.190  1.00  40.64      A  C
ATOM    248  ND1  HIS   32      60.806   8.072  -1.910  1.00  40.77      A  N
ATOM    249  CE1  HIS   32      60.821   7.011  -1.124  1.00  39.75      A  C
ATOM    250  NE2  HIS   32      60.692   5.933  -1.875  1.00  40.60      A  N
ATOM    251  C    HIS   32      59.683   7.149  -6.220  1.00  39.73      A  C
ATOM    252  O    HIS   32      59.706   5.903  -6.146  1.00  39.15      A  O
ATOM    253  N    TRP   33      58.659   7.821  -6.740  1.00  38.56      A  N
ATOM    254  CA   TRP   33      57.523   7.098  -7.285  1.00  39.42      A  C
ATOM    255  CB   TRP   33      56.386   8.057  -7.620  1.00  37.61      A  C
ATOM    256  CG   TRP   33      55.604   8.354  -6.390  1.00  37.25      A  C
ATOM    257  CD2  TRP   33      54.885   7.403  -5.601  1.00  36.51      A  C
ATOM    258  CE2  TRP   33      54.437   8.076  -4.441  1.00  36.69      A  C
ATOM    259  CE3  TRP   33      54.577   6.043  -5.762  1.00  36.83      A  C
ATOM    260  CD1  TRP   33      55.555   9.539  -5.701  1.00  36.63      A  C
ATOM    261  NE1  TRP   33      54.863   9.376  -4.531  1.00  36.59      A  N
ATOM    262  CZ2  TRP   33      53.694   7.435  -3.441  1.00  36.26      A  C
ATOM    263  CZ3  TRP   33      53.836   5.403  -4.768  1.00  36.84      A  C
ATOM    264  CH2  TRP   33      53.403   6.101  -3.622  1.00  36.34      A  C
ATOM    265  C    TRP   33      57.924   6.257  -8.511  1.00  40.59      A  C
ATOM    266  O    TRP   33      57.377   5.174  -8.731  1.00  39.92      A  O
ATOM    267  N    LYS   34      58.891   6.748  -9.294  1.00  41.94      A  N
ATOM    268  CA   LYS   34      59.366   6.001 -10.461  1.00  43.02      A  C
ATOM    269  CB   LYS   34      60.401   6.820 -11.250  1.00  43.13      A  C
ATOM    270  CG   LYS   34      59.734   7.899 -12.113  1.00  43.71      A  C
ATOM    271  CD   LYS   34      60.716   8.791 -12.868  1.00  44.32      A  C
ATOM    272  CE   LYS   34      59.948   9.884 -13.626  1.00  45.48      A  C
ATOM    273  NZ   LYS   34      60.830  10.748 -14.462  1.00  46.76      A  N
ATOM    274  C    LYS   34      59.945   4.668 -10.011  1.00  43.38      A  C
ATOM    275  O    LYS   34      59.610   3.625 -10.581  1.00  43.34      A  O
ATOM    276  N    CYS   35      60.782   4.705  -8.973  1.00  43.85      A  N
ATOM    277  CA   CYS   35      61.402   3.496  -8.419  1.00  44.64      A  C
ATOM    278  CB   CYS   35      62.439   3.874  -7.363  1.00  46.14      A  C
ATOM    279  SG   CYS   35      63.748   4.938  -8.023  1.00  51.26      A  S
ATOM    280  C    CYS   35      60.383   2.522  -7.809  1.00  44.23      A  C
ATOM    281  O    CYS   35      60.629   1.324  -7.761  1.00  43.70      A  O
```

Figure 9-5

```
ATOM    282  N   ILE  36     59.251   3.025  -7.329  1.00 43.83     A   N
ATOM    283  CA  ILE  36     58.245   2.128  -6.793  1.00 43.85     A   C
ATOM    284  CB  ILE  36     57.081   2.901  -6.126  1.00 43.61     A   C
ATOM    285  CG2 ILE  36     55.846   1.991  -5.993  1.00 43.35     A   C
ATOM    286  CG1 ILE  36     57.531   3.468  -4.777  1.00 43.29     A   C
ATOM    287  CD1 ILE  36     57.775   2.426  -3.703  1.00 42.14     A   C
ATOM    288  C   ILE  36     57.702   1.338  -7.990  1.00 44.31     A   C
ATOM    289  O   ILE  36     57.386   0.150  -7.862  1.00 44.39     A   O
ATOM    290  N   ARG  37     57.593   2.008  -9.143  1.00 43.84     A   N
ATOM    291  CA  ARG  37     57.105   1.379 -10.370  1.00 43.92     A   C
ATOM    292  CB  ARG  37     56.968   2.407 -11.490  1.00 44.62     A   C
ATOM    293  CG  ARG  37     55.858   3.421 -11.293  1.00 45.78     A   C
ATOM    294  CD  ARG  37     55.882   4.455 -12.410  1.00 46.61     A   C
ATOM    295  NE  ARG  37     55.905   3.840 -13.746  1.00 46.47     A   N
ATOM    296  CZ  ARG  37     56.022   4.535 -14.879  1.00 46.48     A   C
ATOM    297  NH1 ARG  37     56.127   5.858 -14.843  1.00 45.50     A   N
ATOM    298  NH2 ARG  37     56.037   3.915 -16.054  1.00 47.32     A   N
ATOM    299  C   ARG  37     58.091   0.312 -10.820  1.00 43.59     A   C
ATOM    300  O   ARG  37     57.708  -0.783 -11.219  1.00 43.77     A   O
ATOM    301  N   LEU  38     59.371   0.643 -10.769  1.00 43.46     A   N
ATOM    302  CA  LEU  38     60.387  -0.314 -11.155  1.00 43.99     A   C
ATOM    303  CB  LEU  38     61.789   0.308 -11.044  1.00 42.95     A   C
ATOM    304  CG  LEU  38     62.915  -0.664 -11.394  1.00 42.97     A   C
ATOM    305  CD1 LEU  38     62.695  -1.205 -12.820  1.00 43.19     A   C
ATOM    306  CD2 LEU  38     64.249   0.026 -11.286  1.00 42.36     A   C
ATOM    307  C   LEU  38     60.292  -1.558 -10.270  1.00 44.26     A   C
ATOM    308  O   LEU  38     60.311  -2.678 -10.772  1.00 44.35     A   O
ATOM    309  N   GLU  39     60.173  -1.364  -8.955  1.00 45.09     A   N
ATOM    310  CA  GLU  39     60.092  -2.495  -8.028  1.00 45.86     A   C
ATOM    311  CB  GLU  39     59.949  -2.013  -6.582  1.00 47.29     A   C
ATOM    312  CG  GLU  39     59.855  -3.149  -5.556  1.00 49.15     A   C
ATOM    313  CD  GLU  39     59.241  -2.696  -4.234  1.00 51.41     A   C
ATOM    314  OE1 GLU  39     58.157  -2.060  -4.279  1.00 51.92     A   O
ATOM    315  OE2 GLU  39     59.830  -2.982  -3.156  1.00 52.31     A   O
ATOM    316  C   GLU  39     58.936  -3.437  -8.352  1.00 45.88     A   C
ATOM    317  O   GLU  39     59.121  -4.657  -8.422  1.00 44.98     A   O
ATOM    318  N   SER  40     57.750  -2.869  -8.551  1.00 46.13     A   N
ATOM    319  CA  SER  40     56.577  -3.668  -8.859  1.00 47.69     A   C
ATOM    320  CB  SER  40     55.327  -2.811  -8.763  1.00 48.20     A   C
ATOM    321  OG  SER  40     55.532  -1.627  -9.489  1.00 50.40     A   O
ATOM    322  C   SER  40     56.678  -4.296 -10.241  1.00 48.34     A   C
ATOM    323  O   SER  40     56.154  -5.385 -10.472  1.00 47.80     A   O
ATOM    324  N   VAL  41     57.332  -3.603 -11.168  1.00 49.25     A   N
ATOM    325  CA  VAL  41     57.518  -4.168 -12.494  1.00 49.86     A   C
ATOM    326  CB  VAL  41     58.216  -3.164 -13.444  1.00 49.94     A   C
ATOM    327  CG1 VAL  41     58.889  -3.910 -14.598  1.00 49.67     A   C
ATOM    328  CG2 VAL  41     57.193  -2.168 -13.988  1.00 48.67     A   C
ATOM    329  C   VAL  41     58.387  -5.426 -12.326  1.00 50.58     A   C
ATOM    330  O   VAL  41     58.101  -6.467 -12.902  1.00 50.26     A   O
ATOM    331  N   LEU  42     59.430  -5.327 -11.507  1.00 51.44     A   N
ATOM    332  CA  LEU  42     60.321  -6.459 -11.260  1.00 52.96     A   C
ATOM    333  CB  LEU  42     61.577  -5.993 -10.529  1.00 52.24     A   C
ATOM    334  CG  LEU  42     62.477  -5.056 -11.326  1.00 51.87     A   C
ATOM    335  CD1 LEU  42     63.592  -4.514 -10.449  1.00 51.81     A   C
ATOM    336  CD2 LEU  42     63.042  -5.805 -12.511  1.00 52.06     A   C
ATOM    337  C   LEU  42     59.651  -7.584 -10.459  1.00 54.08     A   C
ATOM    338  O   LEU  42     59.845  -8.763 -10.751  1.00 54.14     A   O
```

Figure 9-6

```
ATOM  339 N    LEU 43   58.870  -7.224  -9.444 1.00 55.38      A N
ATOM  340 CA   LEU 43   58.173  -8.228  -8.648 1.00 56.23      A C
ATOM  341 CB   LEU 43   57.541  -7.591  -7.409 1.00 55.91      A C
ATOM  342 CG   LEU 43   58.547  -7.268  -6.301 1.00 56.27      A C
ATOM  343 CD1  LEU 43   57.833  -6.677  -5.089 1.00 55.71      A C
ATOM  344 CD2  LEU 43   59.295  -8.550  -5.917 1.00 56.03      A C
ATOM  345 C    LEU 43   57.107  -8.886  -9.509 1.00 56.98      A C
ATOM  346 O    LEU 43   56.917 -10.100  -9.464 1.00 56.77      A O
ATOM  347 N    HIS 44   56.412  -8.079 -10.297 1.00 58.29      A N
ATOM  348 CA   HIS 44   55.392  -8.611 -11.180 1.00 60.10      A C
ATOM  349 CB   HIS 44   54.793  -7.509 -12.035 1.00 60.55      A C
ATOM  350 CG   HIS 44   53.589  -7.942 -12.807 1.00 61.91      A C
ATOM  351 CD2  HIS 44   53.449  -8.333 -14.096 1.00 62.12      A C
ATOM  352 ND1  HIS 44   52.335  -8.026 -12.241 1.00 62.19      A N
ATOM  353 CE1  HIS 44   51.473  -8.448 -13.149 1.00 62.39      A C
ATOM  354 NE2  HIS 44   52.124  -8.642 -14.282 1.00 62.61      A N
ATOM  355 C    HIS 44   56.042  -9.642 -12.096 1.00 61.07      A C
ATOM  356 O    HIS 44   55.558 -10.767 -12.229 1.00 61.43      A O
ATOM  357 N    LYS 45   57.144  -9.258 -12.727 1.00 61.91      A N
ATOM  358 CA   LYS 45   57.843 -10.168 -13.622 1.00 63.23      A C
ATOM  359 CB   LYS 45   59.067  -9.476 -14.232 1.00 63.48      A C
ATOM  360 CG   LYS 45   59.688 -10.224 -15.408 1.00 65.06      A C
ATOM  361 CD   LYS 45   58.671 -10.411 -16.536 1.00 66.65      A C
ATOM  362 CE   LYS 45   59.213 -11.287 -17.655 1.00 67.48      A C
ATOM  363 NZ   LYS 45   58.173 -11.590 -18.694 1.00 68.22      A N
ATOM  364 C    LYS 45   58.278 -11.411 -12.849 1.00 63.93      A C
ATOM  365 O    LYS 45   58.177 -12.532 -13.344 1.00 63.98      A O
ATOM  366 N    ALA 46   58.740 -11.203 -11.622 1.00 65.00      A N
ATOM  367 CA   ALA 46   59.210 -12.294 -10.780 1.00 66.07      A C
ATOM  368 CB   ALA 46   59.692 -11.748  -9.447 1.00 66.33      A C
ATOM  369 C    ALA 46   58.168 -13.377 -10.551 1.00 67.03      A C
ATOM  370 O    ALA 46   58.503 -14.562 -10.537 1.00 66.87      A O
ATOM  371 N    LYS 47   56.908 -12.996 -10.364 1.00 67.96      A N
ATOM  372 CA   LYS 47   55.911 -14.024 -10.145 1.00 69.19      A C
ATOM  373 CB   LYS 47   54.694 -13.499  -9.385 1.00 69.02      A C
ATOM  374 CG   LYS 47   53.830 -14.666  -8.922 1.00 69.09      A C
ATOM  375 CD   LYS 47   52.861 -14.328  -7.825 1.00 69.34      A C
ATOM  376 CE   LYS 47   52.344 -15.611  -7.160 1.00 69.85      A C
ATOM  377 NZ   LYS 47   53.425 -16.315  -6.399 1.00 69.49      A N
ATOM  378 C    LYS 47   55.455 -14.687 -11.435 1.00 70.15      A C
ATOM  379 O    LYS 47   54.952 -15.810 -11.406 1.00 70.51      A O
ATOM  380 N    GLN 48   55.613 -14.004 -12.565 1.00 71.01      A N
ATOM  381 CA   GLN 48   55.234 -14.606 -13.838 1.00 72.01      A C
ATOM  382 CB   GLN 48   55.331 -13.593 -14.979 1.00 72.10      A C
ATOM  383 CG   GLN 48   54.108 -12.707 -15.146 1.00 72.64      A C
ATOM  384 CD   GLN 48   54.156 -11.892 -16.432 1.00 73.16      A C
ATOM  385 OE1  GLN 48   53.208 -11.171 -16.769 1.00 72.74      A O
ATOM  386 NE2  GLN 48   55.265 -12.007 -17.162 1.00 72.92      A N
ATOM  387 C    GLN 48   56.188 -15.774 -14.104 1.00 72.50      A C
ATOM  388 O    GLN 48   55.777 -16.829 -14.573 1.00 72.46      A O
ATOM  389 N    MET 49   57.462 -15.572 -13.790 1.00 73.20      A N
ATOM  390 CA   MET 49   58.482 -16.593 -13.977 1.00 74.13      A C
ATOM  391 CB   MET 49   59.871 -15.984 -13.812 1.00 74.97      A C
ATOM  392 CG   MET 49   60.421 -15.290 -15.045 1.00 75.95      A C
ATOM  393 SD   MET 49   61.908 -14.349 -14.628 1.00 78.02      A S
ATOM  394 CE   MET 49   63.001 -15.638 -13.995 1.00 77.58      A C
ATOM  395 C    MET 49   58.331 -17.744 -12.992 1.00 74.62      A C
```

Figure 9-7

```
ATOM    396  O    MET  49      59.100  -18.704  -13.039  1.00  74.84      A  O
ATOM    397  N    GLY  50      57.361  -17.642  -12.088  1.00  74.92      A  N
ATOM    398  CA   GLY  50      57.142  -18.704  -11.123  1.00  75.60      A  C
ATOM    399  C    GLY  50      57.832  -18.590   -9.772  1.00  76.32      A  C
ATOM    400  O    GLY  50      57.556  -19.392   -8.879  1.00  76.41      A  O
ATOM    401  N    LEU  51      58.721  -17.612   -9.600  1.00  76.99      A  N
ATOM    402  CA   LEU  51      59.416  -17.447   -8.324  1.00  77.49      A  C
ATOM    403  CB   LEU  51      60.363  -16.240   -8.346  1.00  77.59      A  C
ATOM    404  CG   LEU  51      61.685  -16.273   -9.115  1.00  77.64      A  C
ATOM    405  CD1  LEU  51      62.403  -17.577   -8.808  1.00  77.84      A  C
ATOM    406  CD2  LEU  51      61.432  -16.136  -10.609  1.00  77.94      A  C
ATOM    407  C    LEU  51      58.442  -17.265   -7.166  1.00  78.07      A  C
ATOM    408  O    LEU  51      57.326  -16.767   -7.340  1.00  78.08      A  O
ATOM    409  N    SER  52      58.880  -17.671   -5.978  1.00  78.55      A  N
ATOM    410  CA   SER  52      58.074  -17.546   -4.772  1.00  78.91      A  C
ATOM    411  CB   SER  52      57.852  -18.920   -4.133  1.00  79.15      A  C
ATOM    412  OG   SER  52      57.048  -19.745   -4.957  1.00  79.45      A  O
ATOM    413  C    SER  52      58.791  -16.641   -3.784  1.00  78.82      A  C
ATOM    414  O    SER  52      58.170  -16.051   -2.905  1.00  78.82      A  O
ATOM    415  N    HIS  53      60.104  -16.539   -3.943  1.00  79.10      A  N
ATOM    416  CA   HIS  53      60.923  -15.729   -3.060  1.00  79.47      A  C
ATOM    417  CB   HIS  53      61.424  -16.575   -1.887  1.00  80.08      A  C
ATOM    418  CG   HIS  53      60.334  -17.210   -1.085  1.00  81.19      A  C
ATOM    419  CD2  HIS  53      59.814  -18.460   -1.120  1.00  81.41      A  C
ATOM    420  ND1  HIS  53      59.615  -16.522   -0.129  1.00  81.62      A  N
ATOM    421  CE1  HIS  53      58.699  -17.321    0.388  1.00  81.90      A  C
ATOM    422  NE2  HIS  53      58.797  -18.503   -0.197  1.00  81.66      A  N
ATOM    423  C    HIS  53      62.137  -15.167   -3.777  1.00  79.57      A  C
ATOM    424  O    HIS  53      62.596  -15.714   -4.777  1.00  79.36      A  O
ATOM    425  N    ILE  54      62.643  -14.063   -3.243  1.00  79.68      A  N
ATOM    426  CA   ILE  54      63.842  -13.404   -3.739  1.00  79.81      A  C
ATOM    427  CB   ILE  54      63.546  -12.096   -4.482  1.00  79.85      A  C
ATOM    428  CG2  ILE  54      64.859  -11.463   -4.919  1.00  79.82      A  C
ATOM    429  CG1  ILE  54      62.634  -12.350   -5.689  1.00  80.09      A  C
ATOM    430  CD1  ILE  54      63.294  -13.088   -6.833  1.00  79.94      A  C
ATOM    431  C    ILE  54      64.516  -13.059   -2.427  1.00  80.08      A  C
ATOM    432  O    ILE  54      64.034  -12.204   -1.681  1.00  80.16      A  O
ATOM    433  N    GLY  55      65.622  -13.727   -2.131  1.00  80.10      A  N
ATOM    434  CA   GLY  55      66.276  -13.472   -0.866  1.00  79.87      A  C
ATOM    435  C    GLY  55      65.301  -13.996    0.170  1.00  79.59      A  C
ATOM    436  O    GLY  55      64.716  -15.065   -0.016  1.00  79.69      A  O
ATOM    437  N    LEU  56      65.092  -13.247    1.245  1.00  79.13      A  N
ATOM    438  CA   LEU  56      64.164  -13.684    2.281  1.00  78.46      A  C
ATOM    439  CB   LEU  56      64.704  -13.253    3.647  1.00  79.27      A  C
ATOM    440  CG   LEU  56      66.144  -13.754    3.817  1.00  80.06      A  C
ATOM    441  CD1  LEU  56      66.785  -13.118    5.032  1.00  80.45      A  C
ATOM    442  CD2  LEU  56      66.144  -15.283    3.919  1.00  80.38      A  C
ATOM    443  C    LEU  56      62.773  -13.104    2.017  1.00  77.35      A  C
ATOM    444  O    LEU  56      61.782  -13.513    2.619  1.00  76.92      A  O
ATOM    445  N    GLN  57      62.722  -12.164    1.079  1.00  76.11      A  N
ATOM    446  CA   GLN  57      61.492  -11.484    0.684  1.00  74.76      A  C
ATOM    447  CB   GLN  57      61.866  -10.261   -0.149  1.00  74.52      A  C
ATOM    448  CG   GLN  57      60.701   -9.492   -0.720  1.00  74.53      A  C
ATOM    449  CD   GLN  57      61.155   -8.363   -1.624  1.00  74.34      A  C
ATOM    450  OE1  GLN  57      60.334   -7.671   -2.228  1.00  73.87      A  O
ATOM    451  NE2  GLN  57      62.473   -8.173   -1.722  1.00  73.35      A  N
ATOM    452  C    GLN  57      60.531  -12.380   -0.108  1.00  73.81      A  C
```

Figure 9-8

```
ATOM  453 O    GLN 57   60.957 -13.150  -0.961 1.00 74.07   A O
ATOM  454 N    VAL 58   59.236 -12.260   0.171 1.00 72.61   A N
ATOM  455 CA   VAL 58   58.205 -13.046  -0.507 1.00 71.65   A C
ATOM  456 CB   VAL 58   57.004 -13.309   0.429 1.00 71.86   A C
ATOM  457 CG1  VAL 58   55.827 -13.863  -0.361 1.00 71.66   A C
ATOM  458 CG2  VAL 58   57.408 -14.278   1.529 1.00 72.30   A C
ATOM  459 C    VAL 58   57.671 -12.336  -1.749 1.00 71.04   A C
ATOM  460 O    VAL 58   57.469 -11.128  -1.732 1.00 71.47   A O
ATOM  461 N    VAL 59   57.425 -13.084  -2.821 1.00 69.79   A N
ATOM  462 CA   VAL 59   56.906 -12.489  -4.051 1.00 68.54   A C
ATOM  463 CB   VAL 59   57.283 -13.318  -5.297 1.00 68.36   A C
ATOM  464 CG1  VAL 59   56.464 -12.866  -6.494 1.00 67.94   A C
ATOM  465 CG2  VAL 59   58.762 -13.158  -5.592 1.00 68.50   A C
ATOM  466 C    VAL 59   55.392 -12.349  -4.002 1.00 67.77   A C
ATOM  467 O    VAL 59   54.668 -13.342  -4.008 1.00 67.87   A O
ATOM  468 N    PRO 60   54.897 -11.101  -3.984 1.00 66.96   A N
ATOM  469 CD   PRO 60   55.709  -9.881  -4.157 1.00 66.59   A C
ATOM  470 CA   PRO 60   53.473 -10.764  -3.933 1.00 65.90   A C
ATOM  471 CB   PRO 60   53.495  -9.249  -3.769 1.00 66.07   A C
ATOM  472 CG   PRO 60   54.681  -8.867  -4.593 1.00 66.24   A C
ATOM  473 C    PRO 60   52.687 -11.184  -5.169 1.00 65.27   A C
ATOM  474 O    PRO 60   53.258 -11.435  -6.221 1.00 65.02   A O
ATOM  475 N    PRO 61   51.353 -11.267  -5.047 1.00 64.85   A N
ATOM  476 CD   PRO 61   50.560 -11.118  -3.813 1.00 64.51   A C
ATOM  477 CA   PRO 61   50.492 -11.650  -6.168 1.00 64.05   A C
ATOM  478 CB   PRO 61   49.101 -11.725  -5.529 1.00 63.76   A C
ATOM  479 CG   PRO 61   49.380 -11.996  -4.094 1.00 63.90   A C
ATOM  480 C    PRO 61   50.561 -10.555  -7.238 1.00 63.69   A C
ATOM  481 O    PRO 61   50.829  -9.397  -6.925 1.00 63.83   A O
ATOM  482 N    LEU 62   50.314 -10.923  -8.490 1.00 63.18   A N
ATOM  483 CA   LEU 62   50.341  -9.981  -9.605 1.00 62.42   A C
ATOM  484 CB   LEU 62   49.988 -10.716 -10.908 1.00 62.47   A C
ATOM  485 CG   LEU 62   50.879 -11.908 -11.292 1.00 62.53   A C
ATOM  486 CD1  LEU 62   50.247 -12.670 -12.444 1.00 62.12   A C
ATOM  487 CD2  LEU 62   52.274 -11.429 -11.670 1.00 61.73   A C
ATOM  488 C    LEU 62   49.379  -8.803  -9.388 1.00 62.25   A C
ATOM  489 O    LEU 62   49.690  -7.653  -9.745 1.00 62.19   A O
ATOM  490 N    THR 63   48.212  -9.084  -8.807 1.00 61.33   A N
ATOM  491 CA   THR 63   47.225  -8.033  -8.547 1.00 60.60   A C
ATOM  492 CB   THR 63   45.957  -8.583  -7.872 1.00 60.86   A C
ATOM  493 OG1  THR 63   46.302  -9.144  -6.595 1.00 60.93   A O
ATOM  494 CG2  THR 63   45.303  -9.639  -8.748 1.00 61.27   A C
ATOM  495 C    THR 63   47.791  -6.957  -7.622 1.00 59.59   A C
ATOM  496 O    THR 63   47.408  -5.791  -7.705 1.00 59.50   A O
ATOM  497 N    VAL 64   48.688  -7.354  -6.728 1.00 58.40   A N
ATOM  498 CA   VAL 64   49.283  -6.407  -5.807 1.00 57.58   A C
ATOM  499 CB   VAL 64   49.955  -7.118  -4.629 1.00 57.81   A C
ATOM  500 CG1  VAL 64   50.671  -6.096  -3.755 1.00 58.28   A C
ATOM  501 CG2  VAL 64   48.913  -7.868  -3.825 1.00 57.62   A C
ATOM  502 C    VAL 64   50.310  -5.528  -6.512 1.00 56.91   A C
ATOM  503 O    VAL 64   50.286  -4.301  -6.374 1.00 57.16   A O
ATOM  504 N    SER 65   51.210  -6.147  -7.267 1.00 55.49   A N
ATOM  505 CA   SER 65   52.213  -5.378  -7.989 1.00 54.22   A C
ATOM  506 CB   SER 65   53.199  -6.296  -8.701 1.00 52.67   A C
ATOM  507 OG   SER 65   53.899  -7.076  -7.770 1.00 51.05   A O
ATOM  508 C    SER 65   51.525  -4.494  -9.011 1.00 54.34   A C
ATOM  509 O    SER 65   51.977  -3.381  -9.275 1.00 54.46   A O
```

Figure 9-9

```
ATOM  510  N    GLU  66   50.437  -4.995  -9.593  1.00  54.16  A  N
ATOM  511  CA   GLU  66   49.703  -4.220 -10.582  1.00  54.10  A  C
ATOM  512  CB   GLU  66   48.594  -5.061 -11.221  1.00  55.91  A  C
ATOM  513  CG   GLU  66   49.040  -5.903 -12.409  1.00  58.04  A  C
ATOM  514  CD   GLU  66   48.067  -7.039 -12.712  1.00  60.11  A  C
ATOM  515  OE1  GLU  66   46.841  -6.827 -12.567  1.00  61.14  A  O
ATOM  516  OE2  GLU  66   48.524  -8.138 -13.110  1.00  60.59  A  O
ATOM  517  C    GLU  66   49.105  -2.995  -9.925  1.00  52.81  A  C
ATOM  518  O    GLU  66   49.218  -1.885 -10.446  1.00  52.58  A  O
ATOM  519  N    THR  67   48.486  -3.191  -8.768  1.00  51.50  A  N
ATOM  520  CA   THR  67   47.874  -2.075  -8.065  1.00  50.77  A  C
ATOM  521  CB   THR  67   47.064  -2.558  -6.874  1.00  51.06  A  C
ATOM  522  OG1  THR  67   45.928  -3.276  -7.364  1.00  51.12  A  O
ATOM  523  CG2  THR  67   46.580  -1.373  -6.022  1.00  51.15  A  C
ATOM  524  C    THR  67   48.902  -1.052  -7.620  1.00  49.72  A  C
ATOM  525  O    THR  67   48.696   0.146  -7.792  1.00  49.78  A  O
ATOM  526  N    LYS  68   50.007  -1.521  -7.056  1.00  49.07  A  N
ATOM  527  CA   LYS  68   51.068  -0.620  -6.634  1.00  48.70  A  C
ATOM  528  CB   LYS  68   52.156  -1.402  -5.885  1.00  48.42  A  C
ATOM  529  CG   LYS  68   51.682  -1.935  -4.535  1.00  48.63  A  C
ATOM  530  CD   LYS  68   52.743  -2.730  -3.818  1.00  49.00  A  C
ATOM  531  CE   LYS  68   53.855  -1.834  -3.310  1.00  50.39  A  C
ATOM  532  NZ   LYS  68   54.897  -2.633  -2.597  1.00  51.08  A  N
ATOM  533  C    LYS  68   51.655   0.127  -7.848  1.00  47.98  A  C
ATOM  534  O    LYS  68   51.935   1.322  -7.768  1.00  48.13  A  O
ATOM  535  N    GLY  69   51.822  -0.566  -8.973  1.00  47.18  A  N
ATOM  536  CA   GLY  69   52.348   0.085 -10.158  1.00  46.57  A  C
ATOM  537  C    GLY  69   51.405   1.156 -10.695  1.00  46.36  A  C
ATOM  538  O    GLY  69   51.829   2.182 -11.223  1.00  45.98  A  O
ATOM  539  N    HIS  70   50.111   0.918 -10.549  1.00  46.88  A  N
ATOM  540  CA   HIS  70   49.088   1.852 -11.015  1.00  47.05  A  C
ATOM  541  CB   HIS  70   47.726   1.128 -11.049  1.00  49.95  A  C
ATOM  542  CG   HIS  70   46.565   2.001 -11.430  1.00  53.51  A  C
ATOM  543  CD2  HIS  70   45.701   2.720 -10.667  1.00  54.15  A  C
ATOM  544  ND1  HIS  70   46.159   2.176 -12.738  1.00  55.24  A  N
ATOM  545  CE1  HIS  70   45.092   2.961 -12.764  1.00  56.29  A  C
ATOM  546  NE2  HIS  70   44.794   3.306 -11.521  1.00  55.51  A  N
ATOM  547  C    HIS  70   49.039   3.080 -10.091  1.00  46.04  A  C
ATOM  548  O    HIS  70   48.942   4.206 -10.567  1.00  46.02  A  O
ATOM  549  N    ASN  71   49.107   2.873  -8.780  1.00  44.23  A  N
ATOM  550  CA   ASN  71   49.064   4.006  -7.859  1.00  43.49  A  C
ATOM  551  CB   ASN  71   48.979   3.552  -6.399  1.00  43.31  A  C
ATOM  552  CG   ASN  71   47.700   2.804  -6.093  1.00  43.38  A  C
ATOM  553  OD1  ASN  71   46.637   3.124  -6.630  1.00  42.92  A  O
ATOM  554  ND2  ASN  71   47.792   1.814  -5.210  1.00  42.84  A  N
ATOM  555  C    ASN  71   50.308   4.848  -8.027  1.00  43.40  A  C
ATOM  556  O    ASN  71   50.246   6.082  -7.968  1.00  43.20  A  O
ATOM  557  N    ALA  72   51.436   4.169  -8.224  1.00  42.52  A  N
ATOM  558  CA   ALA  72   52.709   4.827  -8.415  1.00  42.91  A  C
ATOM  559  CB   ALA  72   53.794   3.789  -8.565  1.00  43.36  A  C
ATOM  560  C    ALA  72   52.671   5.738  -9.640  1.00  43.69  A  C
ATOM  561  O    ALA  72   53.210   6.846  -9.609  1.00  44.42  A  O
ATOM  562  N    ILE  73   52.031   5.276 -10.714  1.00  44.16  A  N
ATOM  563  CA   ILE  73   51.923   6.056 -11.943  1.00  45.29  A  C
ATOM  564  CB   ILE  73   51.330   5.204 -13.108  1.00  46.53  A  C
ATOM  565  CG2  ILE  73   51.207   6.048 -14.378  1.00  45.93  A  C
ATOM  566  CG1  ILE  73   52.231   3.996 -13.393  1.00  47.40  A  C
```

Figure 9-10

```
ATOM    567  CD1 ILE   73      51.620   3.000 -14.390  1.00 48.08      A C
ATOM    568  C   ILE   73      51.042   7.281 -11.716  1.00 45.23      A C
ATOM    569  O   ILE   73      51.361   8.375 -12.173  1.00 45.93      A O
ATOM    570  N   GLU   74      49.928   7.100 -11.020  1.00 45.39      A N
ATOM    571  CA  GLU   74      49.043   8.218 -10.726  1.00 45.81      A C
ATOM    572  CB  GLU   74      47.766   7.707 -10.037  1.00 47.67      A C
ATOM    573  CG  GLU   74      46.934   8.767  -9.277  1.00 51.96      A C
ATOM    574  CD  GLU   74      45.572   8.231  -8.787  1.00 54.09      A C
ATOM    575  OE1 GLU   74      45.011   8.787  -7.819  1.00 55.11      A O
ATOM    576  OE2 GLU   74      45.050   7.259  -9.381  1.00 56.56      A O
ATOM    577  C   GLU   74      49.773   9.254  -9.855  1.00 44.93      A C
ATOM    578  O   GLU   74      49.691  10.441 -10.115  1.00 44.51      A O
ATOM    579  N   MET   75      50.494   8.817  -8.828  1.00 44.69      A N
ATOM    580  CA  MET   75      51.218   9.769  -7.983  1.00 44.77      A C
ATOM    581  CB  MET   75      51.948   9.044  -6.838  1.00 43.45      A C
ATOM    582  CG  MET   75      51.016   8.468  -5.771  1.00 41.26      A C
ATOM    583  SD  MET   75      49.743   9.681  -5.292  1.00 40.93      A S
ATOM    584  CE  MET   75      50.726  10.925  -4.472  1.00 38.01      A C
ATOM    585  C   MET   75      52.231  10.560  -8.817  1.00 45.09      A C
ATOM    586  O   MET   75      52.254  11.797  -8.799  1.00 45.08      A O
ATOM    587  N   GLN   76      53.063   9.833  -9.552  1.00 45.68      A N
ATOM    588  CA  GLN   76      54.069  10.449 -10.399  1.00 46.49      A C
ATOM    589  CB  GLN   76      54.781   9.370 -11.208  1.00 46.46      A C
ATOM    590  CG  GLN   76      55.925   9.861 -12.051  1.00 47.16      A C
ATOM    591  CD  GLN   76      56.325   8.859 -13.133  1.00 48.45      A C
ATOM    592  OE1 GLN   76      56.408   7.657 -12.889  1.00 48.25      A O
ATOM    593  NE2 GLN   76      56.584   9.364 -14.334  1.00 49.70      A N
ATOM    594  C   GLN   76      53.477  11.498 -11.348  1.00 46.98      A C
ATOM    595  O   GLN   76      53.992  12.612 -11.428  1.00 47.05      A O
ATOM    596  N   MET   77      52.398  11.154 -12.054  1.00 47.48      A N
ATOM    597  CA  MET   77      51.780  12.090 -13.007  1.00 48.68      A C
ATOM    598  CB  MET   77      50.641  11.425 -13.783  1.00 51.56      A C
ATOM    599  CG  MET   77      51.086  10.229 -14.604  1.00 55.80      A C
ATOM    600  SD  MET   77      50.032   9.902 -16.034  1.00 61.56      A S
ATOM    601  CE  MET   77      48.386  10.496 -15.441  1.00 59.60      A C
ATOM    602  C   MET   77      51.257  13.366 -12.390  1.00 48.01      A C
ATOM    603  O   MET   77      51.466  14.446 -12.932  1.00 48.30      A O
ATOM    604  N   HIS   78      50.558  13.245 -11.268  1.00 47.22      A N
ATOM    605  CA  HIS   78      50.025  14.410 -10.589  1.00 46.56      A C
ATOM    606  CB  HIS   78      49.091  13.975  -9.467  1.00 46.56      A C
ATOM    607  CG  HIS   78      47.799  13.405  -9.952  1.00 47.21      A C
ATOM    608  CD2 HIS   78      47.335  12.132  -9.970  1.00 47.31      A C
ATOM    609  ND1 HIS   78      46.807  14.182 -10.511  1.00 47.21      A N
ATOM    610  CE1 HIS   78      45.788  13.412 -10.851  1.00 46.97      A C
ATOM    611  NE2 HIS   78      46.083  12.165 -10.533  1.00 46.84      A N
ATOM    612  C   HIS   78      51.159  15.275 -10.038  1.00 46.61      A C
ATOM    613  O   HIS   78      51.105  16.506 -10.114  1.00 45.64      A O
ATOM    614  N   LEU   79      52.188  14.634  -9.492  1.00 46.91      A N
ATOM    615  CA  LEU   79      53.322  15.378  -8.955  1.00 48.23      A C
ATOM    616  CB  LEU   79      54.305  14.446  -8.238  1.00 47.50      A C
ATOM    617  CG  LEU   79      53.774  14.000  -6.880  1.00 47.25      A C
ATOM    618  CD1 LEU   79      54.689  12.965  -6.272  1.00 46.12      A C
ATOM    619  CD2 LEU   79      53.639  15.224  -5.974  1.00 46.83      A C
ATOM    620  C   LEU   79      54.039  16.146 -10.056  1.00 49.25      A C
ATOM    621  O   LEU   79      54.370  17.315  -9.863  1.00 48.44      A O
ATOM    622  N   GLU   80      54.270  15.492 -11.199  1.00 50.89      A N
ATOM    623  CA  GLU   80      54.935  16.138 -12.331  1.00 52.95      A C
```

Figure 9-11

| | | | | | | | | | | | |
|---|---|---|---|---|---|---|---|---|---|---|---|
| ATOM | 624 | CB | GLU | 80 | 55.153 | 15.148 | -13.485 | 1.00 | 54.30 | A | C |
| ATOM | 625 | CG | GLU | 80 | 56.186 | 14.083 | -13.173 | 1.00 | 57.20 | A | C |
| ATOM | 626 | CD | GLU | 80 | 56.489 | 13.172 | -14.351 | 1.00 | 59.28 | A | C |
| ATOM | 627 | OE1 | GLU | 80 | 55.530 | 12.730 | -15.026 | 1.00 | 60.50 | A | O |
| ATOM | 628 | OE2 | GLU | 80 | 57.689 | 12.887 | -14.592 | 1.00 | 60.47 | A | O |
| ATOM | 629 | C | GLU | 80 | 54.106 | 17.328 | -12.804 | 1.00 | 53.25 | A | C |
| ATOM | 630 | O | GLU | 80 | 54.655 | 18.390 | -13.123 | 1.00 | 53.27 | A | O |
| ATOM | 631 | N | SER | 81 | 52.787 | 17.154 | -12.836 | 1.00 | 53.42 | A | N |
| ATOM | 632 | CA | SER | 81 | 51.894 | 18.239 | -13.233 | 1.00 | 54.18 | A | C |
| ATOM | 633 | CB | SER | 81 | 50.450 | 17.767 | -13.221 | 1.00 | 54.74 | A | C |
| ATOM | 634 | OG | SER | 81 | 49.576 | 18.850 | -13.490 | 1.00 | 55.20 | A | O |
| ATOM | 635 | C | SER | 81 | 52.046 | 19.424 | -12.277 | 1.00 | 54.89 | A | C |
| ATOM | 636 | O | SER | 81 | 52.216 | 20.558 | -12.712 | 1.00 | 55.36 | A | O |
| ATOM | 637 | N | LEU | 82 | 51.983 | 19.164 | -10.973 | 1.00 | 55.30 | A | N |
| ATOM | 638 | CA | LEU | 82 | 52.152 | 20.229 | -9.988 | 1.00 | 55.75 | A | C |
| ATOM | 639 | CB | LEU | 82 | 51.936 | 19.699 | -8.571 | 1.00 | 54.69 | A | C |
| ATOM | 640 | CG | LEU | 82 | 52.099 | 20.781 | -7.504 | 1.00 | 54.34 | A | C |
| ATOM | 641 | CD1 | LEU | 82 | 50.815 | 21.562 | -7.414 | 1.00 | 53.84 | A | C |
| ATOM | 642 | CD2 | LEU | 82 | 52.436 | 20.177 | -6.166 | 1.00 | 54.01 | A | C |
| ATOM | 643 | C | LEU | 82 | 53.568 | 20.803 | -10.081 | 1.00 | 56.56 | A | C |
| ATOM | 644 | O | LEU | 82 | 53.802 | 21.976 | -9.783 | 1.00 | 56.24 | A | O |
| ATOM | 645 | N | ALA | 83 | 54.511 | 19.962 | -10.493 | 1.00 | 58.03 | A | N |
| ATOM | 646 | CA | ALA | 83 | 55.905 | 20.369 | -10.616 | 1.00 | 59.47 | A | C |
| ATOM | 647 | CB | ALA | 83 | 56.785 | 19.147 | -10.846 | 1.00 | 58.61 | A | C |
| ATOM | 648 | C | ALA | 83 | 56.110 | 21.396 | -11.736 | 1.00 | 60.74 | A | C |
| ATOM | 649 | O | ALA | 83 | 57.097 | 22.137 | -11.733 | 1.00 | 60.83 | A | O |
| ATOM | 650 | N | LYS | 84 | 55.184 | 21.449 | -12.690 | 1.00 | 61.59 | A | N |
| ATOM | 651 | CA | LYS | 84 | 55.302 | 22.418 | -13.774 | 1.00 | 62.56 | A | C |
| ATOM | 652 | CB | LYS | 84 | 54.404 | 22.030 | -14.950 | 1.00 | 62.71 | A | C |
| ATOM | 653 | CG | LYS | 84 | 54.909 | 20.850 | -15.758 | 1.00 | 63.52 | A | C |
| ATOM | 654 | CD | LYS | 84 | 53.983 | 20.555 | -16.926 | 1.00 | 64.42 | A | C |
| ATOM | 655 | CE | LYS | 84 | 54.494 | 19.395 | -17.762 | 1.00 | 65.33 | A | C |
| ATOM | 656 | NZ | LYS | 84 | 54.681 | 18.148 | -16.949 | 1.00 | 66.33 | A | N |
| ATOM | 657 | C | LYS | 84 | 54.940 | 23.832 | -13.321 | 1.00 | 63.12 | A | C |
| ATOM | 658 | O | LYS | 84 | 55.436 | 24.812 | -13.879 | 1.00 | 63.88 | A | O |
| ATOM | 659 | N | THR | 85 | 54.100 | 23.935 | -12.294 | 1.00 | 62.82 | A | N |
| ATOM | 660 | CA | THR | 85 | 53.640 | 25.228 | -11.794 | 1.00 | 62.19 | A | C |
| ATOM | 661 | CB | THR | 85 | 52.278 | 25.082 | -11.110 | 1.00 | 62.28 | A | C |
| ATOM | 662 | OG1 | THR | 85 | 52.458 | 24.554 | -9.789 | 1.00 | 62.58 | A | O |
| ATOM | 663 | CG2 | THR | 85 | 51.397 | 24.128 | -11.900 | 1.00 | 62.49 | A | C |
| ATOM | 664 | C | THR | 85 | 54.567 | 25.940 | -10.818 | 1.00 | 62.03 | A | C |
| ATOM | 665 | O | THR | 85 | 55.646 | 25.455 | -10.492 | 1.00 | 62.18 | A | O |
| ATOM | 666 | N | GLN | 86 | 54.104 | 27.098 | -10.356 | 1.00 | 61.75 | A | N |
| ATOM | 667 | CA | GLN | 86 | 54.812 | 27.958 | -9.405 | 1.00 | 61.45 | A | C |
| ATOM | 668 | CB | GLN | 86 | 54.078 | 29.297 | -9.278 | 1.00 | 61.57 | A | C |
| ATOM | 669 | CG | GLN | 86 | 52.614 | 29.108 | -8.858 | 1.00 | 62.14 | A | C |
| ATOM | 670 | CD | GLN | 86 | 51.883 | 30.402 | -8.516 | 1.00 | 62.38 | A | C |
| ATOM | 671 | OE1 | GLN | 86 | 52.299 | 31.158 | -7.634 | 1.00 | 62.74 | A | O |
| ATOM | 672 | NE2 | GLN | 86 | 50.774 | 30.650 | -9.205 | 1.00 | 61.95 | A | N |
| ATOM | 673 | C | GLN | 86 | 54.867 | 27.329 | -8.013 | 1.00 | 61.13 | A | C |
| ATOM | 674 | O | GLN | 86 | 55.673 | 27.740 | -7.160 | 1.00 | 61.20 | A | O |
| ATOM | 675 | N | TYR | 87 | 53.992 | 26.353 | -7.781 | 1.00 | 60.20 | A | N |
| ATOM | 676 | CA | TYR | 87 | 53.916 | 25.693 | -6.485 | 1.00 | 59.46 | A | C |
| ATOM | 677 | CB | TYR | 87 | 52.525 | 25.092 | -6.300 | 1.00 | 58.98 | A | C |
| ATOM | 678 | CG | TYR | 87 | 51.427 | 26.116 | -6.426 | 1.00 | 58.07 | A | C |
| ATOM | 679 | CD1 | TYR | 87 | 50.415 | 25.970 | -7.371 | 1.00 | 57.94 | A | C |
| ATOM | 680 | CE1 | TYR | 87 | 49.409 | 26.928 | -7.501 | 1.00 | 57.73 | A | C |

Figure 9-12

| ATOM | 681 | CD2 | TYR | 87 | 51.411 | 27.245 | -5.610 | 1.00 | 57.71 | A | C |
| ATOM | 682 | CE2 | TYR | 87 | 50.414 | 28.204 | -5.731 | 1.00 | 57.67 | A | C |
| ATOM | 683 | CZ | TYR | 87 | 49.415 | 28.039 | -6.677 | 1.00 | 57.74 | A | C |
| ATOM | 684 | OH | TYR | 87 | 48.411 | 28.976 | -6.778 | 1.00 | 57.74 | A | O |
| ATOM | 685 | C | TYR | 87 | 54.976 | 24.624 | -6.278 | 1.00 | 58.74 | A | C |
| ATOM | 686 | O | TYR | 87 | 55.312 | 24.299 | -5.139 | 1.00 | 58.47 | A | O |
| ATOM | 687 | N | GLY | 88 | 55.507 | 24.110 | -7.385 | 1.00 | 58.26 | A | N |
| ATOM | 688 | CA | GLY | 88 | 56.525 | 23.074 | -7.339 | 1.00 | 58.12 | A | C |
| ATOM | 689 | C | GLY | 88 | 57.862 | 23.439 | -6.715 | 1.00 | 58.05 | A | C |
| ATOM | 690 | O | GLY | 88 | 58.674 | 22.557 | -6.424 | 1.00 | 58.44 | A | O |
| ATOM | 691 | N | VAL | 89 | 58.113 | 24.726 | -6.507 | 1.00 | 57.49 | A | N |
| ATOM | 692 | CA | VAL | 89 | 59.381 | 25.137 | -5.908 | 1.00 | 56.30 | A | C |
| ATOM | 693 | CB | VAL | 89 | 59.850 | 26.519 | -6.441 | 1.00 | 56.80 | A | C |
| ATOM | 694 | CG1 | VAL | 89 | 59.987 | 26.466 | -7.951 | 1.00 | 56.07 | A | C |
| ATOM | 695 | CG2 | VAL | 89 | 58.864 | 27.618 | -6.017 | 1.00 | 56.49 | A | C |
| ATOM | 696 | C | VAL | 89 | 59.233 | 25.213 | -4.395 | 1.00 | 55.45 | A | C |
| ATOM | 697 | O | VAL | 89 | 60.224 | 25.338 | -3.680 | 1.00 | 55.38 | A | O |
| ATOM | 698 | N | GLU | 90 | 57.992 | 25.145 | -3.911 | 1.00 | 54.16 | A | N |
| ATOM | 699 | CA | GLU | 90 | 57.748 | 25.196 | -2.473 | 1.00 | 53.28 | A | C |
| ATOM | 700 | CB | GLU | 90 | 56.255 | 25.286 | -2.156 | 1.00 | 53.99 | A | C |
| ATOM | 701 | CG | GLU | 90 | 55.504 | 26.462 | -2.751 | 1.00 | 54.89 | A | C |
| ATOM | 702 | CD | GLU | 90 | 54.035 | 26.452 | -2.323 | 1.00 | 55.99 | A | C |
| ATOM | 703 | OE1 | GLU | 90 | 53.589 | 25.423 | -1.760 | 1.00 | 55.65 | A | O |
| ATOM | 704 | OE2 | GLU | 90 | 53.322 | 27.455 | -2.555 | 1.00 | 56.55 | A | O |
| ATOM | 705 | C | GLU | 90 | 58.277 | 23.896 | -1.906 | 1.00 | 51.88 | A | C |
| ATOM | 706 | O | GLU | 90 | 58.452 | 22.931 | -2.636 | 1.00 | 52.62 | A | O |
| ATOM | 707 | N | PRO | 91 | 58.550 | 23.847 | -0.598 | 1.00 | 50.56 | A | N |
| ATOM | 708 | CD | PRO | 91 | 58.505 | 24.878 | 0.455 | 1.00 | 49.51 | A | C |
| ATOM | 709 | CA | PRO | 91 | 59.057 | 22.577 | -0.073 | 1.00 | 49.29 | A | C |
| ATOM | 710 | CB | PRO | 91 | 59.598 | 22.973 | 1.300 | 1.00 | 49.36 | A | C |
| ATOM | 711 | CG | PRO | 91 | 58.666 | 24.066 | 1.711 | 1.00 | 49.00 | A | C |
| ATOM | 712 | C | PRO | 91 | 57.946 | 21.514 | -0.004 | 1.00 | 48.29 | A | C |
| ATOM | 713 | O | PRO | 91 | 56.817 | 21.797 | 0.420 | 1.00 | 47.68 | A | O |
| ATOM | 714 | N | TRP | 92 | 58.280 | 20.304 | -0.443 | 1.00 | 47.19 | A | N |
| ATOM | 715 | CA | TRP | 92 | 57.360 | 19.174 | -0.445 | 1.00 | 45.78 | A | C |
| ATOM | 716 | CB | TRP | 92 | 56.958 | 18.806 | -1.881 | 1.00 | 45.47 | A | C |
| ATOM | 717 | CG | TRP | 92 | 56.036 | 19.799 | -2.502 | 1.00 | 46.29 | A | C |
| ATOM | 718 | CD2 | TRP | 92 | 54.611 | 19.864 | -2.340 | 1.00 | 46.73 | A | C |
| ATOM | 719 | CE2 | TRP | 92 | 54.164 | 21.016 | -3.025 | 1.00 | 46.82 | A | C |
| ATOM. | 720 | CE3 | TRP | 92 | 53.671 | 19.062 | -1.679 | 1.00 | 46.77 | A | C |
| ATOM | 721 | CD1 | TRP | 92 | 56.382 | 20.880 | -3.263 | 1.00 | 46.70 | A | C |
| ATOM | 722 | NE1 | TRP | 92 | 55.263 | 21.616 | -3.580 | 1.00 | 46.75 | A | N |
| ATOM | 723 | CZ2 | TRP | 92 | 52.813 | 21.389 | -3.066 | 1.00 | 47.53 | A | C |
| ATOM | 724 | CZ3 | TRP | 92 | 52.329 | 19.431 | -1.719 | 1.00 | 46.89 | A | C |
| ATOM | 725 | CH2 | TRP | 92 | 51.911 | 20.585 | -2.408 | 1.00 | 47.84 | A | C |
| ATOM | 726 | C | TRP | 92 | 58.022 | 17.984 | 0.230 | 1.00 | 44.90 | A | C |
| ATOM | 727 | O | TRP | 92 | 59.022 | 17.458 | -0.250 | 1.00 | 44.47 | A | O |
| ATOM | 728 | N | THR | 93 | 57.453 | 17.566 | 1.350 | 1.00 | 44.52 | A | N |
| ATOM | 729 | CA | THR | 93 | 57.984 | 16.443 | 2.110 | 1.00 | 43.99 | A | C |
| ATOM | 730 | CB | THR | 93 | 57.534 | 16.490 | 3.564 | 1.00 | 43.74 | A | C |
| ATOM | 731 | OG1 | THR | 93 | 56.115 | 16.311 | 3.612 | 1.00 | 43.37 | A | O |
| ATOM | 732 | CG2 | THR | 93 | 57.904 | 17.804 | 4.202 | 1.00 | 42.51 | A | C |
| ATOM | 733 | C | THR | 93 | 57.492 | 15.114 | 1.550 | 1.00 | 44.12 | A | C |
| ATOM | 734 | O | THR | 93 | 56.527 | 15.059 | 0.782 | 1.00 | 43.72 | A | O |
| ATOM | 735 | N | LEU | 94 | 58.168 | 14.046 | 1.956 | 1.00 | 44.10 | A | N |
| ATOM | 736 | CA | LEU | 94 | 57.819 | 12.703 | 1.532 | 1.00 | 44.34 | A | C |
| ATOM | 737 | CB | LEU | 94 | 58.835 | 11.717 | 2.105 | 1.00 | 44.27 | A | C |

Figure 9-13

```
ATOM    738  CG  LEU    94      58.806  10.299   1.548  1.00 45.96      A C
ATOM    739  CD1 LEU    94      60.215   9.713   1.568  1.00 47.11      A C
ATOM    740  CD2 LEU    94      57.840   9.440   2.377  1.00 46.18      A C
ATOM    741  C   LEU    94      56.382  12.364   1.978  1.00 44.03      A C
ATOM    742  O   LEU    94      55.641  11.709   1.253  1.00 43.39      A O
ATOM    743  N   GLN    95      55.990  12.838   3.158  1.00 44.09      A N
ATOM    744  CA  GLN    95      54.643  12.603   3.672  1.00 44.48      A C
ATOM    745  CB  GLN    95      54.517  13.103   5.131  1.00 46.96      A C
ATOM    746  CG  GLN    95      53.057  13.293   5.611  1.00 52.08      A C
ATOM    747  CD  GLN    95      52.914  14.081   6.937  1.00 56.14      A C
ATOM    748  OE1 GLN    95      52.622  13.498   7.997  1.00 57.28      A O
ATOM    749  NE2 GLN    95      53.112  15.413   6.875  1.00 56.83      A N
ATOM    750  C   GLN    95      53.643  13.345   2.785  1.00 43.56      A C
ATOM    751  O   GLN    95      52.610  12.789   2.400  1.00 43.08      A O
ATOM    752  N   ASP    96      53.960  14.605   2.484  1.00 43.21      A N
ATOM    753  CA  ASP    96      53.133  15.479   1.647  1.00 43.12      A C
ATOM    754  CB  ASP    96      53.798  16.857   1.430  1.00 44.46      A C
ATOM    755  CG  ASP    96      53.764  17.756   2.674  1.00 46.02      A C
ATOM    756  OD1 ASP    96      52.806  17.648   3.471  1.00 47.64      A O
ATOM    757  OD2 ASP    96      54.681  18.596   2.841  1.00 46.37      A O
ATOM    758  C   ASP    96      52.850  14.894   0.268  1.00 42.42      A C
ATOM    759  O   ASP    96      51.824  15.203  -0.324  1.00 42.93      A O
ATOM    760  N   THR    97      53.752  14.058  -0.243  1.00 41.67      A N
ATOM    761  CA  THR    97      53.585  13.471  -1.572  1.00 41.23      A C
ATOM    762  CB  THR    97      54.835  13.709  -2.411  1.00 41.10      A C
ATOM    763  OG1 THR    97      55.948  13.087  -1.764  1.00 41.87      A O
ATOM    764  CG2 THR    97      55.113  15.208  -2.546  1.00 40.87      A C
ATOM    765  C   THR    97      53.289  11.968  -1.580  1.00 40.95      A C
ATOM    766  O   THR    97      53.526  11.288  -2.578  1.00 40.67      A O
ATOM    767  N   SER    98      52.764  11.461  -0.470  1.00 40.75      A N
ATOM    768  CA  SER    98      52.444  10.051  -0.330  1.00 40.15      A C
ATOM    769  CB  SER    98      52.515   9.661   1.149  1.00 40.17      A C
ATOM    770  OG  SER    98      51.438  10.232   1.880  1.00 39.17      A O
ATOM    771  C   SER    98      51.052   9.747  -0.866  1.00 40.14      A C
ATOM    772  O   SER    98      50.212  10.623  -0.960  1.00 39.23      A O
ATOM    773  N   TYR    99      50.823   8.493  -1.232  1.00 41.34      A N
ATOM    774  CA  TYR    99      49.517   8.060  -1.712  1.00 41.44      A C
ATOM    775  CB  TYR    99      49.608   6.618  -2.200  1.00 41.19      A C
ATOM    776  CG  TYR    99      48.341   6.109  -2.863  1.00 42.15      A C
ATOM    777  CD1 TYR    99      47.895   6.662  -4.055  1.00 42.04      A C
ATOM    778  CE1 TYR    99      46.714   6.248  -4.642  1.00 42.95      A C
ATOM    779  CD2 TYR    99      47.565   5.107  -2.270  1.00 42.27      A C
ATOM    780  CE2 TYR    99      46.374   4.682  -2.855  1.00 42.84      A C
ATOM    781  CZ  TYR    99      45.952   5.260  -4.043  1.00 43.39      A C
ATOM    782  OH  TYR    99      44.764   4.874  -4.636  1.00 43.42      A O
ATOM    783  C   TYR    99      48.566   8.153  -0.501  1.00 42.33      A C
ATOM    784  O   TYR    99      47.384   8.485  -0.629  1.00 42.42      A O
ATOM    785  N   GLU   100      49.104   7.857   0.678  1.00 42.59      A N
ATOM    786  CA  GLU   100      48.347   7.917   1.915  1.00 43.72      A C
ATOM    787  CB  GLU   100      49.263   7.645   3.103  1.00 44.42      A C
ATOM    788  CG  GLU   100      48.541   7.676   4.434  1.00 46.13      A C
ATOM    789  CD  GLU   100      47.775   6.380   4.718  1.00 48.00      A C
ATOM    790  OE1 GLU   100      47.515   5.605   3.761  1.00 48.00      A O
ATOM    791  OE2 GLU   100      47.431   6.148   5.903  1.00 48.84      A O
ATOM    792  C   GLU   100      47.690   9.281   2.107  1.00 44.23      A C
ATOM    793  O   GLU   100      46.506   9.368   2.411  1.00 43.99      A O
ATOM    794  N   MET   101      48.478  10.340   1.949  1.00 44.91      A N
```

Figure 9-14

| | | | | | | | | | | |
|---|---|---|---|---|---|---|---|---|---|---|
| ATOM | 795 | CA | MET | 101 | 47.990 | 11.702 | 2.103 | 1.00 | 45.55 | A C |
| ATOM | 796 | CB | MET | 101 | 49.172 | 12.674 | 2.104 | 1.00 | 47.28 | A C |
| ATOM | 797 | CG | MET | 101 | 48.947 | 13.958 | 2.899 | 1.00 | 50.47 | A C |
| ATOM | 798 | SD | MET | 101 | 48.528 | 13.596 | 4.638 | 1.00 | 53.82 | A S |
| ATOM | 799 | CE | MET | 101 | 49.699 | 12.310 | 5.010 | 1.00 | 52.81 | A C |
| ATOM | 800 | C | MET | 101 | 47.021 | 12.052 | 0.976 | 1.00 | 45.54 | A C |
| ATOM | 801 | O | MET | 101 | 46.020 | 12.727 | 1.189 | 1.00 | 45.40 | A O |
| ATOM | 802 | N | TRP | 102 | 47.323 | 11.568 | -0.222 | 1.00 | 46.04 | A N |
| ATOM | 803 | CA | TRP | 102 | 46.499 | 11.809 | -1.401 | 1.00 | 46.63 | A C |
| ATOM | 804 | CB | TRP | 102 | 47.077 | 11.029 | -2.586 | 1.00 | 45.54 | A C |
| ATOM | 805 | CG | TRP | 102 | 46.378 | 11.212 | -3.923 | 1.00 | 45.63 | A C |
| ATOM | 806 | CD2 | TRP | 102 | 46.360 | 12.395 | -4.744 | 1.00 | 44.63 | A C |
| ATOM | 807 | CE2 | TRP | 102 | 45.706 | 12.057 | -5.950 | 1.00 | 45.18 | A C |
| ATOM | 808 | CE3 | TRP | 102 | 46.837 | 13.701 | -4.578 | 1.00 | 43.62 | A C |
| ATOM | 809 | CD1 | TRP | 102 | 45.737 | 10.242 | -4.646 | 1.00 | 45.85 | A C |
| ATOM | 810 | NE1 | TRP | 102 | 45.338 | 10.740 | -5.861 | 1.00 | 46.02 | A N |
| ATOM | 811 | CZ2 | TRP | 102 | 45.514 | 12.979 | -6.991 | 1.00 | 45.02 | A C |
| ATOM | 812 | CZ3 | TRP | 102 | 46.648 | 14.622 | -5.612 | 1.00 | 44.72 | A C |
| ATOM | 813 | CH2 | TRP | 102 | 45.991 | 14.254 | -6.805 | 1.00 | 44.79 | A C |
| ATOM | 814 | C | TRP | 102 | 45.059 | 11.382 | -1.136 | 1.00 | 47.34 | A C |
| ATOM | 815 | O | TRP | 102 | 44.111 | 12.096 | -1.475 | 1.00 | 47.56 | A O |
| ATOM | 816 | N | LEU | 103 | 44.900 | 10.213 | -0.523 | 1.00 | 48.53 | A N |
| ATOM | 817 | CA | LEU | 103 | 43.581 | 9.690 | -0.212 | 1.00 | 49.61 | A C |
| ATOM | 818 | CB | LEU | 103 | 43.649 | 8.168 | -0.100 | 1.00 | 49.73 | A C |
| ATOM | 819 | CG | LEU | 103 | 43.103 | 7.362 | -1.295 | 1.00 | 50.72 | A C |
| ATOM | 820 | CD1 | LEU | 103 | 43.308 | 8.085 | -2.616 | 1.00 | 50.30 | A C |
| ATOM | 821 | CD2 | LEU | 103 | 43.787 | 6.004 | -1.318 | 1.00 | 51.65 | A C |
| ATOM | 822 | C | LEU | 103 | 42.940 | 10.305 | 1.035 | 1.00 | 50.33 | A C |
| ATOM | 823 | O | LEU | 103 | 41.747 | 10.170 | 1.235 | 1.00 | 51.11 | A O |
| ATOM | 824 | N | THR | 104 | 43.724 | 10.978 | 1.871 | 1.00 | 51.20 | A N |
| ATOM | 825 | CA | THR | 104 | 43.183 | 11.639 | 3.063 | 1.00 | 51.77 | A C |
| ATOM | 826 | CB | THR | 104 | 44.306 | 12.160 | 3.987 | 1.00 | 51.93 | A C |
| ATOM | 827 | OG1 | THR | 104 | 45.057 | 11.055 | 4.507 | 1.00 | 52.44 | A O |
| ATOM | 828 | CG2 | THR | 104 | 43.719 | 12.945 | 5.144 | 1.00 | 51.88 | A C |
| ATOM | 829 | C | THR | 104 | 42.343 | 12.847 | 2.629 | 1.00 | 53.12 | A C |
| ATOM | 830 | O | THR | 104 | 42.758 | 13.611 | 1.759 | 1.00 | 53.38 | A O |
| ATOM | 831 | N | PRO | 105 | 41.148 | 13.029 | 3.220 | 1.00 | 53.32 | A N |
| ATOM | 832 | CD | PRO | 105 | 40.423 | 12.081 | 4.089 | 1.00 | 53.45 | A C |
| ATOM | 833 | CA | PRO | 105 | 40.289 | 14.166 | 2.857 | 1.00 | 52.56 | A C |
| ATOM | 834 | CB | PRO | 105 | 39.094 | 14.004 | 3.796 | 1.00 | 53.27 | A C |
| ATOM | 835 | CG | PRO | 105 | 38.972 | 12.506 | 3.900 | 1.00 | 53.15 | A C |
| ATOM | 836 | C | PRO | 105 | 40.975 | 15.523 | 3.024 | 1.00 | 53.00 | A C |
| ATOM | 837 | O | PRO | 105 | 41.650 | 15.763 | 4.023 | 1.00 | 52.86 | A O |
| ATOM | 838 | N | CPR | 106 | 40.822 | 16.422 | 2.032 | 1.00 | 52.84 | A N |
| ATOM | 839 | CD | CPR | 106 | 41.222 | 17.835 | 2.167 | 1.00 | 52.65 | A C |
| ATOM | 840 | CA | CPR | 106 | 40.055 | 16.222 | 0.793 | 1.00 | 52.25 | A C |
| ATOM | 841 | CB | CPR | 106 | 39.813 | 17.651 | 0.302 | 1.00 | 52.25 | A C |
| ATOM | 842 | CG | CPR | 106 | 41.030 | 18.373 | 0.752 | 1.00 | 52.14 | A C |
| ATOM | 843 | C | CPR | 106 | 40.819 | 15.375 | -0.225 | 1.00 | 52.11 | A C |
| ATOM | 844 | O | CPR | 106 | 41.880 | 15.776 | -0.698 | 1.00 | 52.11 | A O |
| ATOM | 845 | N | ALA | 107 | 40.251 | 14.221 | -0.562 | 1.00 | 52.00 | A N |
| ATOM | 846 | CA | ALA | 107 | 40.851 | 13.272 | -1.499 | 1.00 | 52.33 | A C |
| ATOM | 847 | CB | ALA | 107 | 39.927 | 12.045 | -1.652 | 1.00 | 51.77 | A C |
| ATOM | 848 | C | ALA | 107 | 41.225 | 13.819 | -2.883 | 1.00 | 52.24 | A C |
| ATOM | 849 | O | ALA | 107 | 40.527 | 14.649 | -3.459 | 1.00 | 52.13 | A O |
| ATOM | 850 | N | ARG | 108 | 42.340 | 13.319 | -3.403 | 1.00 | 52.80 | A N |
| ATOM | 851 | CA | ARG | 108 | 42.857 | 13.705 | -4.712 | 1.00 | 53.46 | A C |

Figure 9-15

```
ATOM    852  CB  ARG  108    41.933  13.189  -5.817  1.00  53.95    A  C
ATOM    853  CG  ARG  108    41.761  11.685  -5.744  1.00  55.50    A  C
ATOM    854  CD  ARG  108    41.737  11.012  -7.099  1.00  56.92    A  C
ATOM    855  NE  ARG  108    41.823   9.561  -6.949  1.00  58.49    A  N
ATOM    856  CZ  ARG  108    40.913   8.816  -6.320  1.00  59.34    A  C
ATOM    857  NH1 ARG  108    39.834   9.393  -5.787  1.00  58.82    A  N
ATOM    858  NH2 ARG  108    41.100   7.500  -6.195  1.00  58.52    A  N
ATOM    859  C   ARG  108    43.090  15.198  -4.845  1.00  53.26    A  C
ATOM    860  O   ARG  108    42.700  15.838  -5.825  1.00  53.40    A  O
ATOM    861  N   CYS  109    43.740  15.727  -3.817  1.00  52.94    A  N
ATOM    862  CA  CYS  109    44.131  17.125  -3.710  1.00  52.72    A  C
ATOM    863  CB  CYS  109    43.115  17.951  -2.910  1.00  53.89    A  C
ATOM    864  SG  CYS  109    41.471  18.187  -3.615  1.00  59.58    A  S
ATOM    865  C   CYS  109    45.399  17.039  -2.869  1.00  51.39    A  C
ATOM    866  O   CYS  109    45.496  16.184  -1.993  1.00  51.22    A  O
ATOM    867  N   PHE  110    46.371  17.899  -3.133  1.00  49.64    A  N
ATOM    868  CA  PHE  110    47.569  17.902  -2.319  1.00  47.92    A  C
ATOM    869  CB  PHE  110    48.768  18.372  -3.132  1.00  46.98    A  C
ATOM    870  CG  PHE  110    49.241  17.376  -4.152  1.00  46.41    A  C
ATOM    871  CD1 PHE  110    49.285  17.716  -5.503  1.00  45.42    A  C
ATOM    872  CD2 PHE  110    49.660  16.099  -3.759  1.00  45.19    A  C
ATOM    873  CE1 PHE  110    49.741  16.800  -6.452  1.00  45.45    A  C
ATOM    874  CE2 PHE  110    50.112  15.179  -4.694  1.00  45.09    A  C
ATOM    875  CZ  PHE  110    50.154  15.529  -6.051  1.00  45.16    A  C
ATOM    876  C   PHE  110    47.284  18.889  -1.198  1.00  47.55    A  C
ATOM    877  O   PHE  110    46.539  19.835  -1.406  1.00  47.55    A  O
ATOM    878  N   LYS  111    47.847  18.661  -0.013  1.00  47.31    A  N
ATOM    879  CA  LYS  111    47.653  19.570   1.121  1.00  47.26    A  C
ATOM    880  CB  LYS  111    46.428  19.177   1.956  1.00  45.97    A  C
ATOM    881  CG  LYS  111    46.249  17.692   2.234  1.00  44.44    A  C
ATOM    882  CD  LYS  111    45.621  17.002   1.024  1.00  42.96    A  C
ATOM    883  CE  LYS  111    44.949  15.697   1.389  1.00  40.41    A  C
ATOM    884  NZ  LYS  111    44.431  15.019   0.180  1.00  38.42    A  N
ATOM    885  C   LYS  111    48.864  19.668   2.038  1.00  47.98    A  C
ATOM    886  O   LYS  111    49.684  18.764   2.089  1.00  47.91    A  O
ATOM    887  N   LYS  112    48.965  20.776   2.766  1.00  49.32    A  N
ATOM    888  CA  LYS  112    50.076  21.004   3.687  1.00  50.55    A  C
ATOM    889  CB  LYS  112    51.223  21.708   2.975  1.00  50.65    A  C
ATOM    890  CG  LYS  112    51.976  20.836   2.007  1.00  51.49    A  C
ATOM    891  CD  LYS  112    53.268  21.515   1.563  1.00  52.43    A  C
ATOM    892  CE  LYS  112    52.999  22.791   0.782  1.00  52.98    A  C
ATOM    893  NZ  LYS  112    54.265  23.446   0.358  1.00  53.48    A  N
ATOM    894  C   LYS  112    49.666  21.838   4.888  1.00  51.41    A  C
ATOM    895  O   LYS  112    48.615  22.482   4.881  1.00  51.71    A  O
ATOM    896  N   GLN  113    50.521  21.830   5.909  1.00  52.68    A  N
ATOM    897  CA  GLN  113    50.303  22.563   7.157  1.00  53.78    A  C
ATOM    898  CB  GLN  113    50.355  24.082   6.922  1.00  55.72    A  C
ATOM    899  CG  GLN  113    51.735  24.592   6.450  1.00  59.38    A  C
ATOM    900  CD  GLN  113    51.805  26.128   6.298  1.00  62.51    A  C
ATOM    901  OE1 GLN  113    52.803  26.672   5.796  1.00  63.29    A  O
ATOM    902  NE2 GLN  113    50.748  26.827   6.736  1.00  63.37    A  N
ATOM    903  C   GLN  113    48.976  22.163   7.764  1.00  53.50    A  C
ATOM    904  O   GLN  113    48.003  22.913   7.734  1.00  53.37    A  O
ATOM    905  N   GLY  114    48.942  20.959   8.313  1.00  53.59    A  N
ATOM    906  CA  GLY  114    47.716  20.480   8.917  1.00  53.83    A  C
ATOM    907  C   GLY  114    47.612  20.901  10.363  1.00  53.74    A  C
ATOM    908  O   GLY  114    48.617  20.930  11.055  1.00  54.26    A  O
```

Figure 9-16

```
ATOM    909  N    ASN   115     46.411 21.257 10.804 1.00 53.42      A  N
ATOM    910  CA   ASN   115     46.182 21.638 12.188 1.00 53.12      A  C
ATOM    911  CB   ASN   115     45.878 23.123 12.311 1.00 53.32      A  C
ATOM    912  CG   ASN   115     47.140 23.960 12.362 1.00 53.81      A  C
ATOM    913  OD1  ASN   115     47.498 24.639 11.395 1.00 54.29      A  O
ATOM    914  ND2  ASN   115     47.837 23.899 13.492 1.00 53.93      A  N
ATOM    915  C    ASN   115     45.045 20.813 12.756 1.00 53.52      A  C
ATOM    916  O    ASN   115     44.200 20.311 12.011 1.00 52.47      A  O
ATOM    917  N    THR   116     45.034 20.672 14.081 1.00 54.18      A  N
ATOM    918  CA   THR   116     44.041 19.857 14.763 1.00 54.83      A  C
ATOM    919  CB   THR   116     44.630 19.207 16.038 1.00 54.43      A  C
ATOM    920  OG1  THR   116     45.766 18.408 15.692 1.00 53.37      A  O
ATOM    921  CG2  THR   116     43.597 18.318 16.718 1.00 54.28      A  C
ATOM    922  C    THR   116     42.771 20.576 15.153 1.00 56.35      A  C
ATOM    923  O    THR   116     42.797 21.695 15.650 1.00 56.33      A  O
ATOM    924  N    VAL   117     41.654 19.899 14.918 1.00 57.98      A  N
ATOM    925  CA   VAL   117     40.337 20.409 15.254 1.00 59.35      A  C
ATOM    926  CB   VAL   117     39.480 20.600 13.990 1.00 58.21      A  C
ATOM    927  CG1  VAL   117     38.060 20.927 14.371 1.00 58.14      A  C
ATOM    928  CG2  VAL   117     40.059 21.697 13.144 1.00 58.11      A  C
ATOM    929  C    VAL   117     39.684 19.365 16.162 1.00 60.67      A  C
ATOM    930  O    VAL   117     39.652 18.178 15.838 1.00 60.79      A  O
ATOM    931  N    GLU   118     39.185 19.801 17.309 1.00 62.42      A  N
ATOM    932  CA   GLU   118     38.533 18.881 18.227 1.00 64.32      A  C
ATOM    933  CB   GLU   118     39.070 19.059 19.643 1.00 65.94      A  C
ATOM    934  CG   GLU   118     40.065 18.001 20.046 1.00 69.34      A  C
ATOM    935  CD   GLU   118     40.645 18.243 21.425 1.00 72.07      A  C
ATOM    936  OE1  GLU   118     39.923 18.797 22.294 1.00 73.23      A  O
ATOM    937  OE2  GLU   118     41.821 17.861 21.642 1.00 73.45      A  O
ATOM    938  C    GLU   118     37.041 19.087 18.247 1.00 64.63      A  C
ATOM    939  O    GLU   118     36.570 20.218 18.270 1.00 64.76      A  O
ATOM    940  N    VAL   119     36.299 17.990 18.232 1.00 65.33      A  N
ATOM    941  CA   VAL   119     34.861 18.073 18.292 1.00 65.93      A  C
ATOM    942  CB   VAL   119     34.213 17.706 16.965 1.00 65.52      A  C
ATOM    943  CG1  VAL   119     32.703 17.729 17.131 1.00 64.71      A  C
ATOM    944  CG2  VAL   119     34.651 18.703 15.889 1.00 65.12      A  C
ATOM    945  C    VAL   119     34.334 17.151 19.379 1.00 67.13      A  C
ATOM    946  O    VAL   119     34.453 15.930 19.303 1.00 67.14      A  O
ATOM    947  N    LYS   120     33.775 17.777 20.402 1.00 68.74      A  N
ATOM    948  CA   LYS   120     33.176 17.108 21.543 1.00 70.48      A  C
ATOM    949  CB   LYS   120     33.396 17.990 22.781 1.00 71.53      A  C
ATOM    950  CG   LYS   120     32.650 17.582 24.052 1.00 74.09      A  C
ATOM    951  CD   LYS   120     33.161 18.401 25.251 1.00 76.34      A  C
ATOM    952  CE   LYS   120     32.438 18.055 26.555 1.00 78.25      A  C
ATOM    953  NZ   LYS   120     33.116 18.692 27.735 1.00 79.51      A  N
ATOM    954  C    LYS   120     31.671 16.935 21.249 1.00 70.98      A  C
ATOM    955  O    LYS   120     30.923 17.904 21.271 1.00 70.66      A  O
ATOM    956  N    PHE   121     31.230 15.711 20.960 1.00 71.97      A  N
ATOM    957  CA   PHE   121     29.823 15.455 20.626 1.00 73.19      A  C
ATOM    958  CB   PHE   121     29.670 14.174 19.787 1.00 71.72      A  C
ATOM    959  CG   PHE   121     30.370 14.237 18.468 1.00 70.35      A  C
ATOM    960  CD1  PHE   121     31.716 13.933 18.378 1.00 69.69      A  C
ATOM    961  CD2  PHE   121     29.697 14.658 17.329 1.00 69.38      A  C
ATOM    962  CE1  PHE   121     32.391 14.043 17.175 1.00 69.41      A  C
ATOM    963  CE2  PHE   121     30.362 14.776 16.108 1.00 69.38      A  C
ATOM    964  CZ   PHE   121     31.718 14.468 16.032 1.00 69.21      A  C
ATOM    965  C    PHE   121     28.869 15.383 21.790 1.00 75.14      A  C
```

Figure 9-17

```
ATOM    966  O    PHE   121      28.814  14.370  22.493  1.00 75.38      A  O
ATOM    967  N    ASP   122      28.114  16.470  21.983  1.00 77.64      A  N
ATOM    968  CA   ASP   122      27.130  16.559  23.058  1.00 79.83      A  C
ATOM    969  CB   ASP   122      26.298  15.278  22.944  1.00 81.18      A  C
ATOM    970  CG   ASP   122      26.253  14.482  24.184  1.00 82.98      A  C
ATOM    971  OD1  ASP   122      27.234  14.521  24.957  1.00 83.92      A  O
ATOM    972  OD2  ASP   122      25.227  13.782  24.343  1.00 84.51      A  O
ATOM    973  C    ASP   122      27.958  16.774  24.356  1.00 81.16      A  C
ATOM    974  O    ASP   122      29.174  16.903  24.258  1.00 81.53      A  O
ATOM    975  N    GLY   123      27.402  16.780  25.562  1.00 82.40      A  N
ATOM    976  CA   GLY   123      28.284  17.050  26.701  1.00 83.84      A  C
ATOM    977  C    GLY   123      29.318  16.105  27.334  1.00 85.22      A  C
ATOM    978  O    GLY   123      29.398  16.083  28.557  1.00 85.75      A  O
ATOM    979  N    CYS   124      30.136  15.382  26.563  1.00 86.08      A  N
ATOM    980  CA   CYS   124      31.152  14.458  27.134  1.00 86.91      A  C
ATOM    981  CB   CYS   124      30.768  13.012  26.792  1.00 87.95      A  C
ATOM    982  SG   CYS   124      29.067  12.519  27.219  1.00 91.09      A  S
ATOM    983  C    CYS   124      32.596  14.701  26.627  1.00 86.83      A  C
ATOM    984  O    CYS   124      32.759  15.168  25.514  1.00 87.20      A  O
ATOM    985  N    GLU   125      33.633  14.351  27.396  1.00 86.01      A  N
ATOM    986  CA   GLU   125      35.007  14.553  26.915  1.00 85.03      A  C
ATOM    987  CB   GLU   125      35.894  15.171  28.005  1.00 85.02      A  C
ATOM    988  CG   GLU   125      35.402  16.581  28.423  1.00 85.55      A  C
ATOM    989  CD   GLU   125      36.408  17.305  29.297  1.00 86.02      A  C
ATOM    990  OE1  GLU   125      36.391  17.059  30.520  1.00 86.07      A  O
ATOM    991  OE2  GLU   125      37.216  18.102  28.764  1.00 85.85      A  O
ATOM    992  C    GLU   125      35.523  13.192  26.447  1.00 84.30      A  C
ATOM    993  O    GLU   125      36.630  13.063  25.933  1.00 84.30      A  O
ATOM    994  N    ASP   126      34.645  12.202  26.598  1.00 83.32      A  N
ATOM    995  CA   ASP   126      34.875  10.840  26.172  1.00 82.20      A  C
ATOM    996  CB   ASP   126      33.995   9.829  26.958  1.00 83.38      A  C
ATOM    997  CG   ASP   126      34.106   8.439  26.407  1.00 84.68      A  C
ATOM    998  OD1  ASP   126      35.004   8.284  25.570  1.00 84.97      A  O
ATOM    999  OD2  ASP   126      33.329   7.521  26.804  1.00 85.40      A  O
ATOM   1000  C    ASP   126      34.401  10.868  24.701  1.00 81.13      A  C
ATOM   1001  O    ASP   126      34.867  10.065  23.883  1.00 81.42      A  O
ATOM   1002  N    ASN   127      33.440  11.747  24.372  1.00 79.74      A  N
ATOM   1003  CA   ASN   127      32.940  11.864  22.993  1.00 77.88      A  C
ATOM   1004  CB   ASN   127      31.423  12.072  22.967  1.00 78.24      A  C
ATOM   1005  CG   ASN   127      30.679  10.874  22.388  1.00 78.99      A  C
ATOM   1006  OD1  ASN   127      30.617  10.732  21.182  1.00 79.47      A  O
ATOM   1007  ND2  ASN   127      30.101   9.999  23.272  1.00 79.55      A  N
ATOM   1008  C    ASN   127      33.657  13.017  22.291  1.00 76.16      A  C
ATOM   1009  O    ASN   127      33.024  13.951  21.833  1.00 76.32      A  O
ATOM   1010  N    VAL   128      34.986  12.906  22.234  1.00 74.53      A  N
ATOM   1011  CA   VAL   128      35.874  13.857  21.591  1.00 72.68      A  C
ATOM   1012  CB   VAL   128      36.981  14.336  22.554  1.00 72.94      A  C
ATOM   1013  CG1  VAL   128      38.014  15.156  21.806  1.00 72.74      A  C
ATOM   1014  CG2  VAL   128      36.343  15.182  23.657  1.00 72.83      A  C
ATOM   1015  C    VAL   128      36.506  13.214  20.365  1.00 71.66      A  C
ATOM   1016  O    VAL   128      36.762  12.016  20.332  1.00 72.13      A  O
ATOM   1017  N    MET   129      36.718  13.998  19.322  1.00 70.69      A  N
ATOM   1018  CA   MET   129      37.325  13.433  18.127  1.00 68.95      A  C
ATOM   1019  CB   MET   129      36.230  13.009  17.139  1.00 69.74      A  C
ATOM   1020  CG   MET   129      36.733  12.122  16.007  1.00 71.57      A  C
ATOM   1021  SD   MET   129      36.349  10.362  16.257  1.00 74.01      A  S
ATOM   1022  CE   MET   129      36.993  10.068  17.947  1.00 72.71      A  C
```

Figure 9-18

| | | | | | | | | | |
|---|---|---|---|---|---|---|---|---|---|
| ATOM | 1023 | C | MET | 129 | 38.238 | 14.473 | 17.507 | 1.00 67.02 | A C |
| ATOM | 1024 | O | MET | 129 | 37.964 | 15.663 | 17.592 | 1.00 67.10 | A O |
| ATOM | 1025 | N | GLU | 130 | 39.326 | 14.026 | 16.895 | 1.00 65.06 | A N |
| ATOM | 1026 | CA | GLU | 130 | 40.266 | 14.941 | 16.261 | 1.00 63.00 | A C |
| ATOM | 1027 | CB | GLU | 130 | 41.708 | 14.593 | 16.635 | 1.00 64.21 | A C |
| ATOM | 1028 | CG | GLU | 130 | 42.171 | 15.101 | 17.991 | 1.00 66.44 | A C |
| ATOM | 1029 | CD | GLU | 130 | 43.674 | 14.920 | 18.165 | 1.00 68.26 | A C |
| ATOM | 1030 | OE1 | GLU | 130 | 44.350 | 14.688 | 17.134 | 1.00 68.99 | A O |
| ATOM | 1031 | OE2 | GLU | 130 | 44.182 | 15.018 | 19.310 | 1.00 68.94 | A O |
| ATOM | 1032 | C | GLU | 130 | 40.133 | 14.888 | 14.750 | 1.00 60.59 | A C |
| ATOM | 1033 | O | GLU | 130 | 39.844 | 13.840 | 14.185 | 1.00 60.21 | A O |
| ATOM | 1034 | N | TYR | 131 | 40.336 | 16.036 | 14.114 | 1.00 58.04 | A N |
| ATOM | 1035 | CA | TYR | 131 | 40.277 | 16.159 | 12.671 | 1.00 55.19 | A C |
| ATOM | 1036 | CB | TYR | 131 | 38.923 | 16.705 | 12.214 | 1.00 55.69 | A C |
| ATOM | 1037 | CG | TYR | 131 | 37.754 | 15.843 | 12.599 | 1.00 56.29 | A C |
| ATOM | 1038 | CD1 | TYR | 131 | 37.048 | 16.081 | 13.774 | 1.00 56.86 | A C |
| ATOM | 1039 | CE1 | TYR | 131 | 35.992 | 15.266 | 14.152 | 1.00 57.62 | A C |
| ATOM | 1040 | CD2 | TYR | 131 | 37.373 | 14.761 | 11.807 | 1.00 56.74 | A C |
| ATOM | 1041 | CE2 | TYR | 131 | 36.313 | 13.933 | 12.175 | 1.00 57.13 | A C |
| ATOM | 1042 | CZ | TYR | 131 | 35.630 | 14.192 | 13.346 | 1.00 57.83 | A C |
| ATOM | 1043 | OH | TYR | 131 | 34.580 | 13.387 | 13.717 | 1.00 59.29 | A O |
| ATOM | 1044 | C | TYR | 131 | 41.373 | 17.117 | 12.250 | 1.00 53.46 | A C |
| ATOM | 1045 | O | TYR | 131 | 41.919 | 17.858 | 13.076 | 1.00 52.91 | A O |
| ATOM | 1046 | N | VAL | 132 | 41.699 | 17.094 | 10.964 | 1.00 51.25 | A N |
| ATOM | 1047 | CA | VAL | 132 | 42.730 | 17.965 | 10.441 | 1.00 49.34 | A C |
| ATOM | 1048 | CB | VAL | 132 | 43.776 | 17.166 | 9.629 | 1.00 48.60 | A C |
| ATOM | 1049 | CG1 | VAL | 132 | 44.864 | 18.091 | 9.127 | 1.00 46.67 | A C |
| ATOM | 1050 | CG2 | VAL | 132 | 44.362 | 16.060 | 10.480 | 1.00 48.13 | A C |
| ATOM | 1051 | C | VAL | 132 | 42.127 | 19.028 | 9.539 | 1.00 49.01 | A C |
| ATOM | 1052 | O | VAL | 132 | 41.170 | 18.768 | 8.811 | 1.00 48.86 | A O |
| ATOM | 1053 | N | VAL | 133 | 42.676 | 20.235 | 9.623 | 1.00 48.45 | A N |
| ATOM | 1054 | CA | VAL | 133 | 42.252 | 21.344 | 8.783 | 1.00 47.54 | A C |
| ATOM | 1055 | CB | VAL | 133 | 41.648 | 22.530 | 9.614 | 1.00 47.95 | A C |
| ATOM | 1056 | CG1 | VAL | 133 | 42.617 | 22.981 | 10.711 | 1.00 48.24 | A C |
| ATOM | 1057 | CG2 | VAL | 133 | 41.345 | 23.703 | 8.687 | 1.00 47.55 | A C |
| ATOM | 1058 | C | VAL | 133 | 43.541 | 21.764 | 8.103 | 1.00 46.68 | A C |
| ATOM | 1059 | O | VAL | 133 | 44.529 | 22.048 | 8.774 | 1.00 46.78 | A O |
| ATOM | 1060 | N | TRP | 134 | 43.539 | 21.763 | 6.774 | 1.00 46.14 | A N |
| ATOM | 1061 | CA | TRP | 134 | 44.730 | 22.100 | 6.014 | 1.00 45.66 | A C |
| ATOM | 1062 | CB | TRP | 134 | 44.817 | 21.222 | 4.750 | 1.00 43.44 | A C |
| ATOM | 1063 | CG | TRP | 134 | 44.748 | 19.743 | 5.022 | 1.00 40.74 | A C |
| ATOM | 1064 | CD2 | TRP | 134 | 45.827 | 18.884 | 5.426 | 1.00 39.81 | A C |
| ATOM | 1065 | CE2 | TRP | 134 | 45.288 | 17.580 | 5.573 | 1.00 39.25 | A C |
| ATOM | 1066 | CE3 | TRP | 134 | 47.193 | 19.087 | 5.678 | 1.00 39.25 | A C |
| ATOM | 1067 | CD1 | TRP | 134 | 43.645 | 18.954 | 4.945 | 1.00 39.38 | A C |
| ATOM | 1068 | NE1 | TRP | 134 | 43.956 | 17.655 | 5.272 | 1.00 38.52 | A N |
| ATOM | 1069 | CZ2 | TRP | 134 | 46.069 | 16.475 | 5.961 | 1.00 39.54 | A C |
| ATOM | 1070 | CZ3 | TRP | 134 | 47.981 | 17.983 | 6.067 | 1.00 39.17 | A C |
| ATOM | 1071 | CH2 | TRP | 134 | 47.410 | 16.694 | 6.204 | 1.00 39.61 | A C |
| ATOM | 1072 | C | TRP | 134 | 44.822 | 23.567 | 5.628 | 1.00 46.47 | A C |
| ATOM | 1073 | O | TRP | 134 | 43.922 | 24.111 | 5.000 | 1.00 46.97 | A O |
| ATOM | 1074 | N | THR | 135 | 45.931 | 24.199 | 5.994 | 1.00 47.30 | A N |
| ATOM | 1075 | CA | THR | 135 | 46.159 | 25.601 | 5.686 | 1.00 48.28 | A C |
| ATOM | 1076 | CB | THR | 135 | 47.442 | 26.100 | 6.385 | 1.00 48.64 | A C |
| ATOM | 1077 | OG1 | THR | 135 | 47.234 | 26.105 | 7.801 | 1.00 48.00 | A O |
| ATOM | 1078 | CG2 | THR | 135 | 47.813 | 27.511 | 5.917 | 1.00 49.40 | A C |
| ATOM | 1079 | C | THR | 135 | 46.276 | 25.822 | 4.172 | 1.00 49.10 | A C |

Figure 9-19

```
ATOM   1080  O    THR  135     45.778  26.809   3.635  1.00  49.62      A    O
ATOM   1081  N    HIS  136     46.939  24.903   3.487  1.00  49.68      A    N
ATOM   1082  CA   HIS  136     47.093  25.012   2.048  1.00  50.38      A    C
ATOM   1083  CB   HIS  136     48.560  25.249   1.685  1.00  52.38      A    C
ATOM   1084  CG   HIS  136     49.199  26.375   2.434  1.00  54.36      A    C
ATOM   1085  CD2  HIS  136     50.298  26.410   3.225  1.00  54.85      A    C
ATOM   1086  ND1  HIS  136     48.688  27.659   2.433  1.00  56.24      A    N
ATOM   1087  CE1  HIS  136     49.442  28.432   3.194  1.00  56.51      A    C
ATOM   1088  NE2  HIS  136     50.426  27.698   3.687  1.00  56.74      A    N
ATOM   1089  C    HIS  136     46.596  23.745   1.346  1.00  50.35      A    C
ATOM   1090  O    HIS  136     46.984  22.632   1.689  1.00  50.05      A    O
ATOM   1091  N    ILE  137     45.714  23.924   0.374  1.00  50.06      A    N
ATOM   1092  CA   ILE  137     45.192  22.807  -0.393  1.00  50.14      A    C
ATOM   1093  CB   ILE  137     43.699  22.555  -0.103  1.00  49.37      A    C
ATOM   1094  CG2  ILE  137     43.097  21.677  -1.190  1.00  48.84      A    C
ATOM   1095  CG1  ILE  137     43.551  21.893   1.263  1.00  48.68      A    C
ATOM   1096  CD1  ILE  137     42.125  21.765   1.734  1.00  48.72      A    C
ATOM   1097  C    ILE  137     45.380  23.144  -1.864  1.00  50.53      A    C
ATOM   1098  O    ILE  137     45.111  24.264  -2.299  1.00  50.35      A    O
ATOM   1099  N    TYR  138     45.860  22.173  -2.622  1.00  51.06      A    N
ATOM   1100  CA   TYR  138     46.098  22.379  -4.036  1.00  51.99      A    C
ATOM   1101  CB   TYR  138     47.544  21.986  -4.359  1.00  50.94      A    C
ATOM   1102  CG   TYR  138     48.555  22.658  -3.439  1.00  50.53      A    C
ATOM   1103  CD1  TYR  138     48.650  22.290  -2.092  1.00  50.38      A    C
ATOM   1104  CE1  TYR  138     49.536  22.924  -1.225  1.00  49.79      A    C
ATOM   1105  CD2  TYR  138     49.386  23.689  -3.898  1.00  50.23      A    C
ATOM   1106  CE2  TYR  138     50.284  24.337  -3.034  1.00  49.69      A    C
ATOM   1107  CZ   TYR  138     50.350  23.946  -1.697  1.00  50.46      A    C
ATOM   1108  OH   TYR  138     51.209  24.578  -0.815  1.00  50.40      A    O
ATOM   1109  C    TYR  138     45.087  21.584  -4.858  1.00  52.88      A    C
ATOM   1110  O    TYR  138     45.109  20.353  -4.879  1.00  52.87      A    O
ATOM   1111  N    LEU  139     44.178  22.308  -5.505  1.00  54.71      A    N
ATOM   1112  CA   LEU  139     43.141  21.701  -6.336  1.00  57.15      A    C
ATOM   1113  CB   LEU  139     41.827  22.490  -6.225  1.00  56.83      A    C
ATOM   1114  CG   LEU  139     41.286  22.691  -4.802  1.00  57.16      A    C
ATOM   1115  CD1  LEU  139     40.186  23.743  -4.802  1.00  57.16      A    C
ATOM   1116  CD2  LEU  139     40.787  21.368  -4.248  1.00  56.93      A    C
ATOM   1117  C    LEU  139     43.610  21.689  -7.780  1.00  58.65      A    C
ATOM   1118  O    LEU  139     44.216  22.645  -8.262  1.00  58.62      A    O
ATOM   1119  N    GLN  140     43.331  20.599  -8.472  1.00  61.37      A    N
ATOM   1120  CA   GLN  140     43.750  20.483  -9.850  1.00  64.81      A    C
ATOM   1121  CB   GLN  140     44.183  19.050 -10.136  1.00  65.56      A    C
ATOM   1122  CG   GLN  140     44.726  18.839 -11.527  1.00  67.60      A    C
ATOM   1123  CD   GLN  140     45.186  17.419 -11.732  1.00  68.95      A    C
ATOM   1124  OE1  GLN  140     44.580  16.487 -11.194  1.00  69.91      A    O
ATOM   1125  NE2  GLN  140     46.251  17.235 -12.518  1.00  69.22      A    N
ATOM   1126  C    GLN  140     42.647  20.892 -10.812  1.00  66.59      A    C
ATOM   1127  O    GLN  140     41.470  20.684 -10.536  1.00  66.91      A    O
ATOM   1128  N    ASP  141     43.039  21.492 -11.934  1.00  68.77      A    N
ATOM   1129  CA   ASP  141     42.088  21.917 -12.958  1.00  70.93      A    C
ATOM   1130  CB   ASP  141     41.902  23.438 -12.948  1.00  71.74      A    C
ATOM   1131  CG   ASP  141     40.781  23.881 -13.868  1.00  72.93      A    C
ATOM   1132  OD1  ASP  141     39.631  23.438 -13.646  1.00  73.67      A    O
ATOM   1133  OD2  ASP  141     41.045  24.656 -14.816  1.00  73.57      A    O
ATOM   1134  C    ASP  141     42.622  21.485 -14.315  1.00  71.66      A    C
ATOM   1135  O    ASP  141     43.439  22.186 -14.918  1.00  71.86      A    O
ATOM   1136  N    ASN  142     42.149  20.339 -14.796  1.00  72.57      A    N
```

Figure 9-20

```
ATOM   1137  CA   ASN  142     42.614  19.796  -16.073  1.00  73.63      A  C
ATOM   1138  CB   ASN  142     42.326  20.777  -17.224  1.00  74.43      A  C
ATOM   1139  CG   ASN  142     40.924  20.589  -17.824  1.00  75.38      A  C
ATOM   1140  OD1  ASN  142     39.921  20.504  -17.103  1.00  75.67      A  O
ATOM   1141  ND2  ASN  142     40.857  20.529  -19.151  1.00  75.26      A  N
ATOM   1142  C    ASN  142     44.115  19.534  -15.930  1.00  73.67      A  C
ATOM   1143  O    ASN  142     44.531  18.389  -15.721  1.00  74.16      A  O
ATOM   1144  N    ASP  143     44.928  20.582  -16.028  1.00  73.02      A  N
ATOM   1145  CA   ASP  143     46.363  20.416  -15.865  1.00  72.01      A  C
ATOM   1146  CB   ASP  143     47.060  20.185  -17.208  1.00  73.04      A  C
ATOM   1147  CG   ASP  143     48.280  19.267  -17.078  1.00  74.14      A  C
ATOM   1148  OD1  ASP  143     48.087  18.039  -16.908  1.00  74.19      A  O
ATOM   1149  OD2  ASP  143     49.429  19.768  -17.129  1.00  74.26      A  O
ATOM   1150  C    ASP  143     46.956  21.634  -15.181  1.00  71.10      A  C
ATOM   1151  O    ASP  143     48.178  21.799  -15.128  1.00  71.13      A  O
ATOM   1152  N    SER  144     46.086  22.496  -14.666  1.00  69.33      A  N
ATOM   1153  CA   SER  144     46.541  23.674  -13.945  1.00  67.69      A  C
ATOM   1154  CB   SER  144     45.833  24.939  -14.459  1.00  68.20      A  C
ATOM   1155  OG   SER  144     44.419  24.854  -14.327  1.00  68.88      A  O
ATOM   1156  C    SER  144     46.229  23.433  -12.462  1.00  66.50      A  C
ATOM   1157  O    SER  144     45.492  22.500  -12.119  1.00  65.91      A  O
ATOM   1158  N    TRP  145     46.789  24.262  -11.586  1.00  64.71      A  N
ATOM   1159  CA   TRP  145     46.565  24.104  -10.157  1.00  62.81      A  C
ATOM   1160  CB   TRP  145     47.801  23.484   -9.515  1.00  61.71      A  C
ATOM   1161  CG   TRP  145     48.030  22.083   -9.934  1.00  59.97      A  C
ATOM   1162  CD2  TRP  145     47.699  20.908   -9.189  1.00  59.11      A  C
ATOM   1163  CE2  TRP  145     48.051  19.795   -9.987  1.00  58.74      A  C
ATOM   1164  CE3  TRP  145     47.138  20.686   -7.924  1.00  58.42      A  C
ATOM   1165  CD1  TRP  145     48.555  21.653  -11.117  1.00  60.11      A  C
ATOM   1166  NE1  TRP  145     48.572  20.278  -11.157  1.00  59.32      A  N
ATOM   1167  CZ2  TRP  145     47.859  18.480   -9.565  1.00  58.39      A  C
ATOM   1168  CZ3  TRP  145     46.946  19.377   -7.503  1.00  58.50      A  C
ATOM   1169  CH2  TRP  145     47.307  18.289   -8.325  1.00  58.75      A  C
ATOM   1170  C    TRP  145     46.196  25.387   -9.420  1.00  62.21      A  C
ATOM   1171  O    TRP  145     46.746  26.456   -9.685  1.00  62.18      A  O
ATOM   1172  N    VAL  146     45.260  25.262   -8.484  1.00  61.19      A  N
ATOM   1173  CA   VAL  146     44.792  26.390   -7.684  1.00  60.12      A  C
ATOM   1174  CB   VAL  146     43.266  26.590   -7.848  1.00  60.23      A  C
ATOM   1175  CG1  VAL  146     42.757  27.571   -6.808  1.00  60.53      A  C
ATOM   1176  CG2  VAL  146     42.952  27.086   -9.246  1.00  59.65      A  C
ATOM   1177  C    VAL  146     45.083  26.165   -6.199  1.00  59.22      A  C
ATOM   1178  O    VAL  146     44.731  25.123   -5.643  1.00  59.20      A  O
ATOM   1179  N    LYS  147     45.713  27.150   -5.563  1.00  57.98      A  N
ATOM   1180  CA   LYS  147     46.034  27.070   -4.144  1.00  56.55      A  C
ATOM   1181  CB   LYS  147     47.389  27.721   -3.894  1.00  56.27      A  C
ATOM   1182  CG   LYS  147     47.848  27.700   -2.456  1.00  56.65      A  C
ATOM   1183  CD   LYS  147     49.313  28.069   -2.393  1.00  57.15      A  C
ATOM   1184  CE   LYS  147     49.863  28.036   -0.978  1.00  57.41      A  C
ATOM   1185  NZ   LYS  147     51.345  28.230   -1.001  1.00  57.08      A  N
ATOM   1186  C    LYS  147     44.946  27.766   -3.321  1.00  55.93      A  C
ATOM   1187  O    LYS  147     44.716  28.963   -3.471  1.00  56.42      A  O
ATOM   1188  N    VAL  148     44.271  27.007   -2.462  1.00  54.77      A  N
ATOM   1189  CA   VAL  148     43.201  27.539   -1.621  1.00  53.26      A  C
ATOM   1190  CB   VAL  148     41.839  26.880   -1.960  1.00  52.65      A  C
ATOM   1191  CG1  VAL  148     41.450  27.198   -3.391  1.00  52.47      A  C
ATOM   1192  CG2  VAL  148     41.913  25.387   -1.752  1.00  52.13      A  C
ATOM   1193  C    VAL  148     43.506  27.306   -0.143  1.00  52.90      A  C
```

Figure 9-21

```
ATOM   1194  O    VAL  148     44.503  26.667   0.192  1.00  53.08      A    O
ATOM   1195  N    THR  149     42.657  27.827   0.743  1.00  52.10      A    N
ATOM   1196  CA   THR  149     42.867  27.647   2.184  1.00  51.43      A    C
ATOM   1197  CB   THR  149     43.320  28.974   2.866  1.00  51.98      A    C
ATOM   1198  OG1  THR  149     43.851  28.680   4.163  1.00  52.76      A    O
ATOM   1199  CG2  THR  149     42.147  29.939   3.028  1.00  51.01      A    C
ATOM   1200  C    THR  149     41.588  27.151   2.849  1.00  50.58      A    C
ATOM   1201  O    THR  149     40.521  27.181   2.232  1.00  50.94      A    O
ATOM   1202  N    SER  150     41.684  26.716   4.106  1.00  49.39      A    N
ATOM   1203  CA   SER  150     40.514  26.199   4.831  1.00  47.99      A    C
ATOM   1204  CB   SER  150     40.833  24.822   5.423  1.00  46.92      A    C
ATOM   1205  OG   SER  150     41.250  23.919   4.428  1.00  45.54      A    O
ATOM   1206  C    SER  150     39.984  27.092   5.958  1.00  47.86      A    C
ATOM   1207  O    SER  150     40.651  28.011   6.413  1.00  47.01      A    O
ATOM   1208  N    SER  151     38.768  26.788   6.403  1.00  48.32      A    N
ATOM   1209  CA   SER  151     38.101  27.501   7.496  1.00  48.97      A    C
ATOM   1210  CB   SER  151     37.152  28.579   6.964  1.00  49.47      A    C
ATOM   1211  OG   SER  151     37.847  29.562   6.220  1.00  51.39      A    O
ATOM   1212  C    SER  151     37.286  26.466   8.253  1.00  48.85      A    C
ATOM   1213  O    SER  151     37.139  25.339   7.790  1.00  48.66      A    O
ATOM   1214  N    VAL  152     36.757  26.842   9.412  1.00  48.57      A    N
ATOM   1215  CA   VAL  152     35.950  25.928  10.196  1.00  49.10      A    C
ATOM   1216  CB   VAL  152     36.739  25.382  11.413  1.00  49.08      A    C
ATOM   1217  CG1  VAL  152     35.837  24.498  12.252  1.00  48.87      A    C
ATOM   1218  CG2  VAL  152     37.963  24.592  10.953  1.00  48.72      A    C
ATOM   1219  C    VAL  152     34.707  26.642  10.711  1.00  49.90      A    C
ATOM   1220  O    VAL  152     34.761  27.833  11.012  1.00  50.84      A    O
ATOM   1221  N    ASP  153     33.586  25.931  10.785  1.00  50.10      A    N
ATOM   1222  CA   ASP  153     32.352  26.501  11.322  1.00  50.89      A    C
ATOM   1223  CB   ASP  153     31.529  27.239  10.243  1.00  50.32      A    C
ATOM   1224  CG   ASP  153     31.016  26.330   9.141  1.00  50.79      A    C
ATOM   1225  OD1  ASP  153     30.669  25.156   9.411  1.00  50.43      A    O
ATOM   1226  OD2  ASP  153     30.929  26.811   7.993  1.00  50.46      A    O
ATOM   1227  C    ASP  153     31.525  25.416  12.016  1.00  51.52      A    C
ATOM   1228  O    ASP  153     31.963  24.270  12.125  1.00  51.99      A    O
ATOM   1229  N    ALA  154     30.346  25.767  12.505  1.00  52.34      A    N
ATOM   1230  CA   ALA  154     29.511  24.797  13.217  1.00  53.50      A    C
ATOM   1231  CB   ALA  154     28.205  25.458  13.651  1.00  52.89      A    C
ATOM   1232  C    ALA  154     29.201  23.533  12.408  1.00  54.42      A    C
ATOM   1233  O    ALA  154     28.940  22.468  12.973  1.00  54.64      A    O
ATOM   1234  N    LYS  155     29.229  23.657  11.085  1.00  54.67      A    N
ATOM   1235  CA   LYS  155     28.923  22.537  10.218  1.00  54.71      A    C
ATOM   1236  CB   LYS  155     28.241  23.035   8.947  1.00  56.45      A    C
ATOM   1237  CG   LYS  155     26.868  23.659   9.150  1.00  59.30      A    C
ATOM   1238  CD   LYS  155     26.352  24.191   7.820  1.00  62.05      A    C
ATOM   1239  CE   LYS  155     25.055  24.980   7.966  1.00  63.92      A    C
ATOM   1240  NZ   LYS  155     24.648  25.564   6.640  1.00  65.38      A    N
ATOM   1241  C    LYS  155     30.109  21.664   9.832  1.00  53.95      A    C
ATOM   1242  O    LYS  155     29.929  20.479   9.568  1.00  54.75      A    O
ATOM   1243  N    GLY  156     31.312  22.221   9.773  1.00  52.44      A    N
ATOM   1244  CA   GLY  156     32.438  21.384   9.402  1.00  50.89      A    C
ATOM   1245  C    GLY  156     33.688  22.107   8.955  1.00  50.02      A    C
ATOM   1246  O    GLY  156     33.865  23.293   9.208  1.00  49.98      A    O
ATOM   1247  N    ILE  157     34.563  21.370   8.288  1.00  49.17      A    N
ATOM   1248  CA   ILE  157     35.819  21.913   7.804  1.00  48.42      A    C
ATOM   1249  CB   ILE  157     37.000  20.959   8.164  1.00  47.74      A    C
ATOM   1250  CG2  ILE  157     38.345  21.599   7.819  1.00  46.13      A    C
```

Figure 9-22

```
ATOM   1251 CG1  ILE   157      36.934 20.625   9.658  1.00 46.72      A  C
ATOM   1252 CD1  ILE   157      38.052 19.758  10.150  1.00 46.92      A  C
ATOM   1253 C    ILE   157      35.641 22.037   6.305  1.00 48.49      A  C
ATOM   1254 O    ILE   157      35.092 21.141   5.671  1.00 48.65      A  O
ATOM   1255 N    TYR   158      36.086 23.151   5.739  1.00 48.61      A  N
ATOM   1256 CA   TYR   158      35.915 23.371   4.315  1.00 48.88      A  C
ATOM   1257 CB   TYR   158      34.553 24.030   4.056  1.00 48.99      A  C
ATOM   1258 CG   TYR   158      34.391 25.427   4.649  1.00 49.49      A  C
ATOM   1259 CD1  TYR   158      34.835 26.556   3.957  1.00 49.88      A  C
ATOM   1260 CE1  TYR   158      34.707 27.836   4.501  1.00 49.51      A  C
ATOM   1261 CD2  TYR   158      33.807 25.617   5.910  1.00 49.07      A  C
ATOM   1262 CE2  TYR   158      33.669 26.892   6.459  1.00 49.23      A  C
ATOM   1263 CZ   TYR   158      34.123 27.999   5.747  1.00 49.98      A  C
ATOM   1264 OH   TYR   158      33.988 29.276   6.267  1.00 50.43      A  O
ATOM   1265 C    TYR   158      37.005 24.228   3.719  1.00 49.05      A  C
ATOM   1266 O    TYR   158      37.796 24.825   4.434  1.00 48.94      A  O
ATOM   1267 N    TYR   159      37.067 24.248   2.396  1.00 49.74      A  N
ATOM   1268 CA   TYR   159      38.019 25.093   1.712  1.00 50.64      A  C
ATOM   1269 CB   TYR   159      39.056 24.273   0.924  1.00 49.98      A  C
ATOM   1270 CG   TYR   159      38.540 23.373  -0.173  1.00 49.39      A  C
ATOM   1271 CD1  TYR   159      38.225 23.881  -1.434  1.00 48.85      A  C
ATOM   1272 CE1  TYR   159      37.791 23.047  -2.460  1.00 49.06      A  C
ATOM   1273 CD2  TYR   159      38.407 22.003   0.037  1.00 49.83      A  C
ATOM   1274 CE2  TYR   159      37.969 21.154  -0.983  1.00 50.35      A  C
ATOM   1275 CZ   TYR   159      37.662 21.686  -2.229  1.00 49.99      A  C
ATOM   1276 OH   TYR   159      37.210 20.853  -3.223  1.00 50.26      A  O
ATOM   1277 C    TYR   159      37.163 25.978   0.816  1.00 51.71      A  C
ATOM   1278 O    TYR   159      36.044 25.609   0.460  1.00 51.22      A  O
ATOM   1279 N    THR   160      37.671 27.155   0.478  1.00 53.28      A  N
ATOM   1280 CA   THR   160      36.913 28.079  -0.342  1.00 55.09      A  C
ATOM   1281 CB   THR   160      36.763 29.440   0.368  1.00 55.25      A  C
ATOM   1282 OG1  THR   160      36.469 29.225   1.749  1.00 55.76      A  O
ATOM   1283 CG2  THR   160      35.628 30.241  -0.249  1.00 55.89      A  C
ATOM   1284 C    THR   160      37.547 28.330  -1.698  1.00 56.20      A  C
ATOM   1285 O    THR   160      38.698 28.730  -1.788  1.00 56.64      A  O
ATOM   1286 N    CYS   161      36.792 28.087  -2.755  1.00 57.65      A  N
ATOM   1287 CA   CYS   161      37.281 28.337  -4.103  1.00 59.16      A  C
ATOM   1288 CB   CYS   161      37.327 27.047  -4.923  1.00 59.84      A  C
ATOM   1289 SG   CYS   161      38.296 27.216  -6.454  1.00 63.61      A  S
ATOM   1290 C    CYS   161      36.261 29.303  -4.696  1.00 59.67      A  C
ATOM   1291 O    CYS   161      35.127 28.915  -4.982  1.00 59.38      A  O
ATOM   1292 N    GLY   162      36.657 30.561  -4.857  1.00 60.17      A  N
ATOM   1293 CA   GLY   162      35.735 31.552  -5.379  1.00 61.06      A  C
ATOM   1294 C    GLY   162      34.609 31.787  -4.380  1.00 61.75      A  C
ATOM   1295 O    GLY   162      34.854 32.195  -3.245  1.00 61.74      A  O
ATOM   1296 N    GLN   163      33.372 31.525  -4.792  1.00 62.05      A  N
ATOM   1297 CA   GLN   163      32.232 31.712  -3.904  1.00 62.36      A  C
ATOM   1298 CB   GLN   163      31.134 32.515  -4.622  1.00 64.20      A  C
ATOM   1299 CG   GLN   163      31.511 33.964  -4.985  1.00 66.71      A  C
ATOM   1300 CD   GLN   163      31.821 34.822  -3.760  1.00 68.81      A  C
ATOM   1301 OE1  GLN   163      31.010 34.919  -2.831  1.00 69.89      A  O
ATOM   1302 NE2  GLN   163      32.998 35.448  -3.754  1.00 69.42      A  N
ATOM   1303 C    GLN   163      31.681 30.363  -3.426  1.00 61.70      A  C
ATOM   1304 O    GLN   163      30.668 30.305  -2.734  1.00 61.50      A  O
ATOM   1305 N    PHE   164      32.371 29.281  -3.773  1.00 60.92      A  N
ATOM   1306 CA   PHE   164      31.932 27.940  -3.393  1.00 60.29      A  C
ATOM   1307 CB   PHE   164      32.117 26.958  -4.567  1.00 61.29      A  C
```

Figure 9-23

```
ATOM   1308  CG   PHE   164      31.480  27.404  -5.866  1.00  62.67      A  C
ATOM   1309  CD1  PHE   164      30.951  26.463  -6.748  1.00  63.53      A  C
ATOM   1310  CD2  PHE   164      31.464  28.744  -6.240  1.00  63.75      A  C
ATOM   1311  CE1  PHE   164      30.426  26.848  -7.982  1.00  63.93      A  C
ATOM   1312  CE2  PHE   164      30.940  29.140  -7.470  1.00  64.31      A  C
ATOM   1313  CZ   PHE   164      30.422  28.189  -8.342  1.00  64.37      A  C
ATOM   1314  C    PHE   164      32.661  27.375  -2.164  1.00  59.30      A  C
ATOM   1315  O    PHE   164      33.883  27.362  -2.106  1.00  59.50      A  O
ATOM   1316  N    LYS   165      31.911  26.920  -1.173  1.00  58.24      A  N
ATOM   1317  CA   LYS   165      32.527  26.327   0.005  1.00  57.50      A  C
ATOM   1318  CB   LYS   165      31.873  26.841   1.298  1.00  57.45      A  C
ATOM   1319  CG   LYS   165      32.049  28.333   1.544  1.00  58.71      A  C
ATOM   1320  CD   LYS   165      31.987  28.686   3.032  1.00  59.66      A  C
ATOM   1321  CE   LYS   165      30.568  28.734   3.593  1.00  61.21      A  C
ATOM   1322  NZ   LYS   165      29.961  30.106   3.528  1.00  61.03      A  N
ATOM   1323  C    LYS   165      32.333  24.812  -0.115  1.00  57.02      A  C
ATOM   1324  O    LYS   165      31.217  24.344  -0.345  1.00  57.29      A  O
ATOM   1325  N    THR   166      33.418  24.051   0.011  1.00  55.71      A  N
ATOM   1326  CA   THR   166      33.341  22.598  -0.073  1.00  54.19      A  C
ATOM   1327  CB   THR   166      34.222  22.035  -1.215  1.00  54.28      A  C
ATOM   1328  OG1  THR   166      33.837  22.625  -2.463  1.00  53.60      A  O
ATOM   1329  CG2  THR   166      34.050  20.518  -1.309  1.00  53.52      A  C
ATOM   1330  C    THR   166      33.822  22.020   1.246  1.00  53.12      A  C
ATOM   1331  O    THR   166      34.911  22.338   1.701  1.00  53.11      A  O
ATOM   1332  N    TYR   167      33.001  21.172   1.851  1.00  52.56      A  N
ATOM   1333  CA   TYR   167      33.317  20.560   3.138  1.00  52.18      A  C
ATOM   1334  CB   TYR   167      32.046  20.404   3.982  1.00  51.45      A  C
ATOM   1335  CG   TYR   167      31.441  21.700   4.458  1.00  51.13      A  C
ATOM   1336  CD1  TYR   167      30.782  22.552   3.575  1.00  50.77      A  C
ATOM   1337  CE1  TYR   167      30.281  23.778   4.003  1.00  51.25      A  C
ATOM   1338  CD2  TYR   167      31.578  22.100   5.793  1.00  50.94      A  C
ATOM   1339  CE2  TYR   167      31.083  23.314   6.235  1.00  51.21      A  C
ATOM   1340  CZ   TYR   167      30.438  24.153   5.337  1.00  52.03      A  C
ATOM   1341  OH   TYR   167      29.970  25.371   5.772  1.00  52.80      A  O
ATOM   1342  C    TYR   167      33.943  19.190   2.979  1.00  52.19      A  C
ATOM   1343  O    TYR   167      33.353  18.320   2.340  1.00  52.89      A  O
ATOM   1344  N    TYR   168      35.128  18.982   3.544  1.00  51.68      A  N
ATOM   1345  CA   TYR   168      35.740  17.672   3.450  1.00  51.77      A  C
ATOM   1346  CB   TYR   168      37.217  17.757   3.016  1.00  50.74      A  C
ATOM   1347  CG   TYR   168      38.102  18.762   3.733  1.00  50.24      A  C
ATOM   1348  CD1  TYR   168      38.911  18.374   4.807  1.00  49.59      A  C
ATOM   1349  CE1  TYR   168      39.768  19.273   5.420  1.00  49.27      A  C
ATOM   1350  CD2  TYR   168      38.173  20.090   3.298  1.00  49.08      A  C
ATOM   1351  CE2  TYR   168      39.026  21.000   3.907  1.00  48.83      A  C
ATOM   1352  CZ   TYR   168      39.819  20.585   4.964  1.00  48.85      A  C
ATOM   1353  OH   TYR   168      40.650  21.479   5.570  1.00  47.97      A  O
ATOM   1354  C    TYR   168      35.555  16.917   4.757  1.00  52.66      A  C
ATOM   1355  O    TYR   168      36.026  15.796   4.923  1.00  52.85      A  O
ATOM   1356  N    VAL   169      34.857  17.550   5.691  1.00  53.89      A  N
ATOM   1357  CA   VAL   169      34.522  16.932   6.971  1.00  55.29      A  C
ATOM   1358  CB   VAL   169      35.524  17.245   8.112  1.00  55.18      A  C
ATOM   1359  CG1  VAL   169      35.071  16.534   9.394  1.00  54.38      A  C
ATOM   1360  CG2  VAL   169      36.926  16.782   7.743  1.00  54.02      A  C
ATOM   1361  C    VAL   169      33.163  17.510   7.332  1.00  56.80      A  C
ATOM   1362  O    VAL   169      33.001  18.719   7.446  1.00  56.84      A  O
ATOM   1363  N    ASN   170      32.185  16.627   7.468  1.00  58.43      A  N
ATOM   1364  CA   ASN   170      30.818  17.002   7.777  1.00  60.13      A  C
```

Figure 9-24

```
ATOM  1365 CB   ASN 170    29.858 16.183  6.899 1.00 60.17      A C
ATOM  1366 CG   ASN 170    28.401 16.581  7.083 1.00 60.23      A C
ATOM  1367 OD1  ASN 170    27.891 16.626  8.203 1.00 59.61      A O
ATOM  1368 ND2  ASN 170    27.721 16.864  5.972 1.00 60.20      A N
ATOM  1369 C    ASN 170    30.595 16.676  9.240 1.00 61.46      A C
ATOM  1370 O    ASN 170    30.648 15.509  9.627 1.00 61.44      A O
ATOM  1371 N    PHE 171    30.340 17.697 10.051 1.00 62.83      A N
ATOM  1372 CA   PHE 171    30.129 17.472 11.472 1.00 64.67      A C
ATOM  1373 CB   PHE 171    30.211 18.796 12.236 1.00 63.85      A C
ATOM  1374 CG   PHE 171    31.611 19.328 12.374 1.00 63.34      A C
ATOM  1375 CD1  PHE 171    31.834 20.643 12.770 1.00 62.67      A C
ATOM  1376 CD2  PHE 171    32.711 18.520 12.089 1.00 63.04      A C
ATOM  1377 CE1  PHE 171    33.130 21.149 12.874 1.00 61.85      A C
ATOM  1378 CE2  PHE 171    34.012 19.018 12.191 1.00 62.54      A C
ATOM  1379 CZ   PHE 171    34.220 20.337 12.583 1.00 62.07      A C
ATOM  1380 C    PHE 171    28.845 16.724 11.824 1.00 66.31      A C
ATOM  1381 O    PHE 171    28.789 16.047 12.848 1.00 66.51      A O
ATOM  1382 N    ASN 172    27.819 16.823 10.986 1.00 68.23      A N
ATOM  1383 CA   ASN 172    26.579 16.115 11.277 1.00 70.40      A C
ATOM  1384 CB   ASN 172    25.433 16.662 10.426 1.00 70.89      A C
ATOM  1385 CG   ASN 172    24.077 16.185 10.906 1.00 71.91      A C
ATOM  1386 OD1  ASN 172    23.985 15.367 11.827 1.00 72.56      A O
ATOM  1387 ND2  ASN 172    23.013 16.693 10.285 1.00 71.98      A N
ATOM  1388 C    ASN 172    26.758 14.615 11.013 1.00 71.60      A C
ATOM  1389 O    ASN 172    26.324 13.775 11.808 1.00 71.59      A O
ATOM  1390 N    ALA 173    27.401 14.286  9.896 1.00 73.21      A N
ATOM  1391 CA   ALA 173    27.649 12.894  9.538 1.00 75.11      A C
ATOM  1392 CB   ALA 173    28.466 12.812  8.245 1.00 74.79      A C
ATOM  1393 C    ALA 173    28.407 12.236 10.686 1.00 76.59      A C
ATOM  1394 O    ALA 173    28.122 11.093 11.062 1.00 76.88      A O
ATOM  1395 N    GLU 174    29.369 12.969 11.246 1.00 77.97      A N
ATOM  1396 CA   GLU 174    30.159 12.466 12.364 1.00 79.40      A C
ATOM  1397 CB   GLU 174    31.233 13.483 12.767 1.00 79.41      A C
ATOM  1398 CG   GLU 174    32.278 13.742 11.693 1.00 79.51      A C
ATOM  1399 CD   GLU 174    32.979 12.475 11.238 1.00 79.77      A C
ATOM  1400 OE1  GLU 174    33.662 11.838 12.069 1.00 79.72      A O
ATOM  1401 OE2  GLU 174    32.842 12.115 10.047 1.00 79.63      A O
ATOM  1402 C    GLU 174    29.243 12.191 13.550 1.00 80.55      A C
ATOM  1403 O    GLU 174    29.420 11.213 14.271 1.00 80.65      A O
ATOM  1404 N    ALA 175    28.257 13.061 13.739 1.00 81.88      A N
ATOM  1405 CA   ALA 175    27.304 12.928 14.835 1.00 83.35      A C
ATOM  1406 CB   ALA 175    26.199 13.969 14.683 1.00 83.10      A C
ATOM  1407 C    ALA 175    26.695 11.528 14.900 1.00 84.55      A C
ATOM  1408 O    ALA 175    26.874 10.794 15.872 1.00 84.29      A O
ATOM  1409 N    GLN 176    25.963 11.176 13.853 1.00 86.09      A N
ATOM  1410 CA   GLN 176    25.314  9.884 13.762 1.00 87.67      A C
ATOM  1411 CB   GLN 176    24.740  9.725 12.358 1.00 88.42      A C
ATOM  1412 CG   GLN 176    23.913 10.924 11.935 1.00 89.33      A C
ATOM  1413 CD   GLN 176    23.587 10.921 10.458 1.00 90.03      A C
ATOM  1414 OE1  GLN 176    22.928 11.833  9.956 1.00 90.22      A O
ATOM  1415 NE2  GLN 176    24.051  9.895  9.750 1.00 90.59      A N
ATOM  1416 C    GLN 176    26.278  8.740 14.068 1.00 88.75      A C
ATOM  1417 O    GLN 176    25.885  7.731 14.654 1.00 89.04      A O
ATOM  1418 N    LYS 177    27.538  8.901 13.671 1.00 89.40      A N
ATOM  1419 CA   LYS 177    28.538  7.864 13.897 1.00 90.10      A C
ATOM  1420 CB   LYS 177    29.818  8.147 13.113 1.00 90.35      A C
ATOM  1421 CG   LYS 177    29.641  8.176 11.605 1.00 90.71      A C
```

Figure 9-25

```
ATOM  1422 CD   LYS 177   30.925  8.646 10.937 1.00 90.89   A C
ATOM  1423 CE   LYS 177   30.657  9.135  9.521 1.00 91.24   A C
ATOM  1424 NZ   LYS 177   31.847  9.803  8.918 1.00 91.45   A N
ATOM  1425 C    LYS 177   28.899  7.738 15.369 1.00 90.71   A C
ATOM  1426 O    LYS 177   29.018  6.625 15.890 1.00 91.04   A O
ATOM  1427 N    TYR 178   29.072  8.873 16.039 1.00 91.02   A N
ATOM  1428 CA   TYR 178   29.435  8.852 17.442 1.00 91.27   A C
ATOM  1429 CB   TYR 178   30.590  9.824 17.653 1.00 91.36   A C
ATOM  1430 CG   TYR 178   31.672  9.435 16.690 1.00 91.90   A C
ATOM  1431 CD1  TYR 178   32.106  8.110 16.628 1.00 92.19   A C
ATOM  1432 CE1  TYR 178   33.008  7.694 15.675 1.00 92.32   A C
ATOM  1433 CD2  TYR 178   32.183 10.339 15.770 1.00 92.01   A C
ATOM  1434 CE2  TYR 178   33.097  9.933 14.803 1.00 92.31   A C
ATOM  1435 CZ   TYR 178   33.502  8.608 14.764 1.00 92.51   A C
ATOM  1436 OH   TYR 178   34.409  8.194 13.823 1.00 92.66   A O
ATOM  1437 C    TYR 178   28.265  9.082 18.398 1.00 91.60   A C
ATOM  1438 O    TYR 178   28.466  9.289 19.592 1.00 91.72   A O
ATOM  1439 N    GLY 179   27.057  9.055 17.828 1.00 91.62   A N
ATOM  1440 CA   GLY 179   25.777  9.152 18.522 1.00 91.51   A C
ATOM  1441 C    GLY 179   25.144 10.169 19.437 1.00 91.41   A C
ATOM  1442 O    GLY 179   25.739 11.157 19.866 1.00 91.54   A O
ATOM  1443 N    ALA 180   23.881  9.857 19.715 1.00 91.12   A N
ATOM  1444 CA   ALA 180   22.964 10.604 20.570 1.00 90.70   A C
ATOM  1445 CB   ALA 180   23.614 10.899 21.936 1.00 90.56   A C
ATOM  1446 C    ALA 180   22.368 11.888 19.969 1.00 90.37   A C
ATOM  1447 O    ALA 180   21.553 11.870 19.028 1.00 90.36   A O
ATOM  1448 N    THR 181   22.814 12.982 20.556 1.00 89.86   A N
ATOM  1449 CA   THR 181   22.491 14.364 20.251 1.00 89.03   A C
ATOM  1450 CB   THR 181   23.187 15.313 21.283 1.00 89.41   A C
ATOM  1451 OG1  THR 181   22.907 14.888 22.627 1.00 89.64   A O
ATOM  1452 CG2  THR 181   22.689 16.766 21.100 1.00 89.61   A C
ATOM  1453 C    THR 181   22.904 14.849 18.854 1.00 88.16   A C
ATOM  1454 O    THR 181   23.618 14.176 18.129 1.00 88.17   A O
ATOM  1455 N    ALA 182   22.386 16.019 18.491 1.00 87.02   A N
ATOM  1456 CA   ALA 182   22.692 16.687 17.238 1.00 85.69   A C
ATOM  1457 CB   ALA 182   21.436 16.854 16.400 1.00 85.72   A C
ATOM  1458 C    ALA 182   23.269 18.042 17.665 1.00 84.51   A C
ATOM  1459 O    ALA 182   23.042 19.076 17.031 1.00 84.37   A O
ATOM  1460 N    ALA 183   23.993 17.999 18.785 1.00 82.95   A N
ATOM  1461 CA   ALA 183   24.635 19.167 19.373 1.00 81.18   A C
ATOM  1462 CB   ALA 183   23.938 19.565 20.661 1.00 81.26   A C
ATOM  1463 C    ALA 183   26.092 18.813 19.662 1.00 79.80   A C
ATOM  1464 O    ALA 183   26.389 17.748 20.221 1.00 79.54   A O
ATOM  1465 N    TRP 184   27.000 19.700 19.263 1.00 77.96   A N
ATOM  1466 CA   TRP 184   28.426 19.477 19.467 1.00 75.97   A C
ATOM  1467 CB   TRP 184   28.996 18.704 18.274 1.00 76.12   A C
ATOM  1468 CG   TRP 184   28.768 19.375 16.952 1.00 76.49   A C
ATOM  1469 CD2  TRP 184   27.807 19.007 15.956 1.00 76.75   A C
ATOM  1470 CE2  TRP 184   27.924 19.937 14.898 1.00 76.54   A C
ATOM  1471 CE3  TRP 184   26.854 17.981 15.855 1.00 77.03   A C
ATOM  1472 CD1  TRP 184   29.412 20.480 16.470 1.00 76.50   A C
ATOM  1473 NE1  TRP 184   28.910 20.823 15.239 1.00 76.43   A N
ATOM  1474 CZ2  TRP 184   27.127 19.874 13.750 1.00 76.71   A C
ATOM  1475 CZ3  TRP 184   26.058 17.917 14.710 1.00 77.27   A C
ATOM  1476 CH2  TRP 184   26.202 18.861 13.673 1.00 77.34   A C
ATOM  1477 C    TRP 184   29.188 20.783 19.666 1.00 74.13   A C
ATOM  1478 O    TRP 184   28.674 21.869 19.403 1.00 73.90   A O
```

Figure 9-26

```
ATOM   1479  N    GLU   185      30.420  20.657  20.141  1.00  72.29       A  N
ATOM   1480  CA   GLU   185      31.289  21.796  20.394  1.00  70.43       A  C
ATOM   1481  CB   GLU   185      31.631  21.863  21.887  1.00  71.06       A  C
ATOM   1482  CG   GLU   185      32.438  23.083  22.315  1.00  72.56       A  C
ATOM   1483  CD   GLU   185      32.777  23.079  23.810  1.00  73.65       A  C
ATOM   1484  OE1  GLU   185      31.838  23.049  24.637  1.00  74.15       A  O
ATOM   1485  OE2  GLU   185      33.983  23.108  24.159  1.00  74.14       A  O
ATOM   1486  C    GLU   185      32.553  21.583  19.565  1.00  68.61       A  C
ATOM   1487  O    GLU   185      33.132  20.496  19.572  1.00  68.46       A  O
ATOM   1488  N    VAL   186      32.968  22.621  18.848  1.00  66.52       A  N
ATOM   1489  CA   VAL   186      34.145  22.559  17.989  1.00  64.43       A  C
ATOM   1490  CB   VAL   186      33.788  23.035  16.570  1.00  63.84       A  C
ATOM   1491  CG1  VAL   186      34.952  22.839  15.645  1.00  63.98       A  C
ATOM   1492  CG2  VAL   186      32.583  22.285  16.063  1.00  63.65       A  C
ATOM   1493  C    VAL   186      35.272  23.434  18.533  1.00  63.67       A  C
ATOM   1494  O    VAL   186      35.044  24.580  18.889  1.00  63.22       A  O
ATOM   1495  N    CYS   187      36.487  22.894  18.591  1.00  63.15       A  N
ATOM   1496  CA   CYS   187      37.637  23.647  19.092  1.00  62.57       A  C
ATOM   1497  CB   CYS   187      38.031  23.180  20.494  1.00  63.20       A  C
ATOM   1498  SG   CYS   187      36.880  23.612  21.799  1.00  68.12       A  S
ATOM   1499  C    CYS   187      38.874  23.559  18.215  1.00  61.46       A  C
ATOM   1500  O    CYS   187      39.458  22.489  18.054  1.00  61.40       A  O
ATOM   1501  N    TYR   188      39.281  24.696  17.667  1.00  60.10       A  N
ATOM   1502  CA   TYR   188      40.472  24.771  16.841  1.00  59.07       A  C
ATOM   1503  CB   TYR   188      40.101  24.686  15.358  1.00  59.06       A  C
ATOM   1504  CG   TYR   188      39.355  25.877  14.822  1.00  59.23       A  C
ATOM   1505  CD1  TYR   188      40.038  26.943  14.245  1.00  59.48       A  C
ATOM   1506  CE1  TYR   188      39.361  28.061  13.767  1.00  60.34       A  C
ATOM   1507  CD2  TYR   188      37.968  25.951  14.911  1.00  59.53       A  C
ATOM   1508  CE2  TYR   188      37.270  27.069  14.438  1.00  60.39       A  C
ATOM   1509  CZ   TYR   188      37.976  28.123  13.866  1.00  60.99       A  C
ATOM   1510  OH   TYR   188      37.308  29.239  13.401  1.00  61.99       A  O
ATOM   1511  C    TYR   188      41.146  26.095  17.169  1.00  58.96       A  C
ATOM   1512  O    TYR   188      40.505  27.152  17.159  1.00  58.52       A  O
ATOM   1513  N    GLY   189      42.437  26.040  17.476  1.00  58.84       A  N
ATOM   1514  CA   GLY   189      43.140  27.254  17.840  1.00  58.97       A  C
ATOM   1515  C    GLY   189      42.630  27.683  19.205  1.00  59.36       A  C
ATOM   1516  O    GLY   189      42.595  26.875  20.139  1.00  58.91       A  O
ATOM   1517  N    SER   190      42.224  28.944  19.326  1.00  59.68       A  N
ATOM   1518  CA   SER   190      41.694  29.457  20.589  1.00  60.22       A  C
ATOM   1519  CB   SER   190      42.485  30.687  21.049  1.00  60.36       A  C
ATOM   1520  OG   SER   190      43.442  30.329  22.031  1.00  60.80       A  O
ATOM   1521  C    SER   190      40.237  29.825  20.397  1.00  60.38       A  C
ATOM   1522  O    SER   190      39.661  30.594  21.165  1.00  60.16       A  O
ATOM   1523  N    THR   191      39.650  29.247  19.360  1.00  60.83       A  N
ATOM   1524  CA   THR   191      38.267  29.494  18.997  1.00  61.06       A  C
ATOM   1525  CB   THR   191      38.192  29.846  17.507  1.00  60.44       A  C
ATOM   1526  OG1  THR   191      38.946  31.039  17.277  1.00  59.31       A  O
ATOM   1527  CG2  THR   191      36.752  30.044  17.061  1.00  60.36       A  C
ATOM   1528  C    THR   191      37.352  28.304  19.281  1.00  61.97       A  C
ATOM   1529  O    THR   191      37.755  27.149  19.132  1.00  62.05       A  O
ATOM   1530  N    VAL   192      36.121  28.592  19.694  1.00  63.08       A  N
ATOM   1531  CA   VAL   192      35.143  27.549  19.980  1.00  64.51       A  C
ATOM   1532  CB   VAL   192      34.943  27.380  21.510  1.00  64.48       A  C
ATOM   1533  CG1  VAL   192      33.918  26.292  21.787  1.00  64.67       A  C
ATOM   1534  CG2  VAL   192      36.258  27.020  22.172  1.00  63.63       A  C
ATOM   1535  C    VAL   192      33.802  27.884  19.321  1.00  65.82       A  C
```

Figure 9-27

```
ATOM   1536 O    VAL  192      33.414 29.046 19.256 1.00 66.10      A  O
ATOM   1537 N    ILE  193      33.111 26.868 18.810 1.00 67.53      A  N
ATOM   1538 CA   ILE  193      31.803 27.059 18.168 1.00 69.37      A  C
ATOM   1539 CB   ILE  193      31.852 26.964 16.626 1.00 69.76      A  C
ATOM   1540 CG2  ILE  193      30.991 28.055 16.011 1.00 70.19      A  C
ATOM   1541 CG1  ILE  193      33.290 27.013 16.132 1.00 70.06      A  C
ATOM   1542 CD1  ILE  193      33.410 26.717 14.659 1.00 70.59      A  C
ATOM   1543 C    ILE  193      30.883 25.931 18.577 1.00 70.57      A  C
ATOM   1544 O    ILE  193      31.315 24.787 18.667 1.00 70.70      A  O
ATOM   1545 N    CYS  194      29.612 26.240 18.795 1.00 72.14      A  N
ATOM   1546 CA   CYS  194      28.651 25.207 19.153 1.00 73.58      A  C
ATOM   1547 CB   CYS  194      28.079 25.486 20.537 1.00 73.49      A  C
ATOM   1548 SG   CYS  194      29.322 25.330 21.848 1.00 74.79      A  S
ATOM   1549 C    CYS  194      27.546 25.135 18.102 1.00 74.91      A  C
ATOM   1550 O    CYS  194      27.367 26.063 17.310 1.00 75.03      A  O
ATOM   1551 N    SER  195      26.822 24.023 18.080 1.00 76.51      A  N
ATOM   1552 CA   SER  195      25.740 23.831 17.118 1.00 78.12      A  C
ATOM   1553 CB   SER  195      25.759 22.391 16.613 1.00 78.00      A  C
ATOM   1554 OG   SER  195      25.648 21.493 17.707 1.00 77.74      A  O
ATOM   1555 C    SER  195      24.393 24.128 17.775 1.00 79.38      A  C
ATOM   1556 O    SER  195      24.320 24.343 18.986 1.00 79.81      A  O
ATOM   1557 N    ALA  196      23.327 24.141 16.981 1.00 80.40      A  N
ATOM   1558 CA   ALA  196      22.001 24.404 17.525 1.00 81.43      A  C
ATOM   1559 CB   ALA  196      21.733 25.905 17.528 1.00 81.02      A  C
ATOM   1560 C    ALA  196      20.911 23.668 16.742 1.00 82.42      A  C
ATOM   1561 O    ALA  196      19.852 24.280 16.455 1.00 82.83      A  O
ATOM   1562 OXT  ALA  196      21.122 22.469 16.439 1.00 83.48      A  O
TER    1563      ALA  196                                           A
ATOM   1564 C1   BLHA   0      54.773  3.853  2.521 1.00 39.81      C  C
ATOM   1565 C2   BLHA   0      55.261  3.475  3.919 1.00 37.85      C  C
ATOM   1566 O4   BLHA   0      55.566  4.809  1.866 1.00 40.61      C  O
ATOM   1567 C5   BLHA   0      54.859  5.336  0.769 1.00 40.28      C  C
ATOM   1568 C6   BLHA   0      53.403  4.861  0.864 1.00 41.30      C  C
ATOM   1569 C8   BLHA   0      53.334  4.276  2.285 1.00 42.52      C  C
ATOM   1570 C10  BLHA   0      55.059  6.835  0.806 1.00 38.97      C  C
ATOM   1571 C11  BLHA   0      55.789  7.247 -0.390 1.00 39.51      C  C
ATOM   1572 O12  BLHA   0      54.675  7.568  1.683 1.00 37.65      C  O
ATOM   1573 C13  BLHA   0      55.530  4.931 -0.512 1.00 39.96      C  C
ATOM   1574 O14  BLHA   0      55.615  3.807 -0.941 1.00 40.04      C  O
ATOM   1575 C15  BLHA   0      56.183  8.530 -0.770 1.00 39.69      C  C
ATOM   1576 C17  BLHA   0      56.894  8.665 -1.984 1.00 40.51      C  C
ATOM   1577 C19  BLHA   0      57.182  7.538 -2.779 1.00 39.62      C  C
ATOM   1578 C21  BLHA   0      56.765  6.250 -2.367 1.00 39.39      C  C
ATOM   1579 C23  BLHA   0      56.068  6.139 -1.167 1.00 39.57      C  C
ATOM   1580 C24  BLHA   0      52.363  5.941  0.525 1.00 42.21      C  C
ATOM   1581 O25  BLHA   0      51.244  6.080  1.015 1.00 42.18      C  O
ATOM   1582 O26  BLHA   0      52.793  6.742 -0.350 1.00 42.55      C  O
ATOM   1583 C28  BLHA   0      52.663  4.935  3.494 1.00 46.05      C  C
ATOM   1584 O29  BLHA   0      51.773  4.464  4.167 1.00 46.64      C  O
ATOM   1585 N30  BLHA   0      53.259  6.186  3.691 1.00 50.54      C  N
ATOM   1586 C31  BLHA   0      52.809  7.074  4.722 1.00 55.52      C  C
ATOM   1587 C33  BLHA   0      52.914  8.457  4.545 1.00 56.81      C  C
ATOM   1588 C35  BLHA   0      52.493  9.343  5.528 1.00 59.75      C  C
ATOM   1589 C37  BLHA   0      51.947  8.874  6.732 1.00 62.90      C  C
ATOM   1590 C38  BLHA   0      51.531  9.840  7.748 1.00 66.37      C  C
ATOM   1591 C39  BLHA   0      51.834  7.479  6.918 1.00 60.60      C  C
ATOM   1592 C41  BLHA   0      52.258  6.591  5.926 1.00 58.11      C  C
```

Figure 9-28

```
ATOM   1593 N43  BLHA  0      51.331  11.169   7.437  1.00 68.53      C  N
ATOM   1594 N44  BLHA  0      50.967  11.809   8.557  1.00 70.73      C  C
ATOM   1595 S46  BLHA  0      50.862  10.900   9.935  1.00 73.47      C  S
ATOM   1596 C47  BLHA  0      51.317   9.521   9.078  1.00 68.98      C  C
ATOM   1597 C49  BLHA  0      56.597   3.702   4.311  1.00 36.12      C  C
ATOM   1598 C51  BLHA  0      57.040   3.343   5.592  1.00 34.98      C  C
ATOM   1599 C53  BLHA  0      56.147   2.744   6.505  1.00 35.63      C  C
ATOM   1600 C55  BLHA  0      54.816   2.519   6.121  1.00 35.24      C  C
ATOM   1601 C57  BLHA  0      54.381   2.877   4.847  1.00 36.58      C  C
ATOM   1602 C3   BLHA  0      57.356  10.064  -2.435  1.00 39.48      C  C
ATOM   1603 CL1  BLHA  0      58.650   3.621   6.036  1.00 29.54      C  C
ATOM   1604 CL2  BLHA  0      56.681   2.297   8.069  1.00 31.33      C  C
TER    1605      BLHA  0                                               C
ATOM   1606 C1   BLHB  0      51.956   0.371   1.421  1.00 60.65      D  C
ATOM   1607 C2   BLHB  0      51.966   0.911  -0.011  1.00 60.16      D  C
ATOM   1608 O4   BLHB  0      53.068   0.731   2.245  1.00 61.06      D  O
ATOM   1609 C5   BLHB  0      53.716  -0.424   2.768  1.00 60.93      D  C
ATOM   1610 C6   BLHB  0      53.039  -1.658   2.219  1.00 61.54      D  C
ATOM   1611 C8   BLHB  0      51.754  -1.152   1.596  1.00 61.53      D  C
ATOM   1612 C10  BLHB  0      55.224  -0.343   2.510  1.00 60.50      D  C
ATOM   1613 C11  BLHB  0      55.918  -0.438   3.800  1.00 60.25      D  C
ATOM   1614 O12  BLHB  0      55.777  -0.229   1.424  1.00 59.21      D  O
ATOM   1615 C13  BLHB  0      53.631  -0.538   4.269  1.00 60.45      D  C
ATOM   1616 O14  BLHB  0      52.623  -0.621   4.931  1.00 60.70      D  O
ATOM   1617 C15  BLHB  0      57.287  -0.434   4.062  1.00 59.93      D  C
ATOM   1618 C17  BLHB  0      57.679  -0.551   5.415  1.00 60.09      D  C
ATOM   1619 C19  BLHB  0      56.717  -0.662   6.442  1.00 60.26      D  C
ATOM   1620 C21  BLHB  0      55.350  -0.662   6.154  1.00 60.17      D  C
ATOM   1621 C23  BLHB  0      54.981  -0.555   4.822  1.00 60.29      D  C
ATOM   1622 C24  BLHB  0      54.011  -2.402   1.346  1.00 62.41      D  C
ATOM   1623 O25  BLHB  0      54.181  -2.254   0.145  1.00 64.02      D  O
ATOM   1624 O26  BLHB  0      54.679  -3.218   2.033  1.00 62.13      D  O
ATOM   1625 C28  BLHB  0      51.214  -1.950   0.406  1.00 62.21      D  C
ATOM   1626 O29  BLHB  0      51.916  -2.512  -0.406  1.00 62.19      D  O
ATOM   1627 N30  BLHB  0      49.834  -1.982   0.389  1.00 63.92      D  N
ATOM   1628 C31  BLHB  0      49.014  -2.712  -0.515  1.00 65.97      D  C
ATOM   1629 C33  BLHB  0      49.158  -2.683  -1.904  1.00 66.81      D  C
ATOM   1630 C35  BLHB  0      48.298  -3.419  -2.712  1.00 69.27      D  C
ATOM   1631 C37  BLHB  0      47.271  -4.204  -2.149  1.00 70.75      D  C
ATOM   1632 C38  BLHB  0      46.362  -4.958  -3.001  1.00 73.01      D  C
ATOM   1633 C39  BLHB  0      47.130  -4.238  -0.759  1.00 69.05      D  C
ATOM   1634 C41  BLHB  0      47.995  -3.499   0.047  1.00 67.23      D  C
ATOM   1635 N43  BLHB  0      45.660  -6.046  -2.532  1.00 74.64      D  N
ATOM   1636 N44  BLHB  0      44.916  -6.511  -3.542  1.00 75.80      D  C
ATOM   1637 S46  BLHB  0      45.027  -5.717  -4.978  1.00 77.16      D  S
ATOM   1638 C47  BLHB  0      46.126  -4.645  -4.325  1.00 74.10      D  C
ATOM   1639 C49  BLHB  0      53.158   1.169  -0.722  1.00 60.03      D  C
ATOM   1640 C51  BLHB  0      53.118   1.667  -2.030  1.00 59.96      D  C
ATOM   1641 C53  BLHB  0      51.899   1.921  -2.652  1.00 59.87      D  C
ATOM   1642 C55  BLHB  0      50.716   1.676  -1.961  1.00 60.05      D  C
ATOM   1643 C57  BLHB  0      50.748   1.178  -0.654  1.00 59.54      D  C
ATOM   1644 C3   BLHB  0      59.166  -0.563   5.788  1.00 58.63      D  C
ATOM   1645 CL1  BLHB  0      54.562   1.967  -2.876  1.00 60.59      D  C
ATOM   1646 CL2  BLHB  0      51.855   2.518  -4.251  1.00 58.33      D  C
TER    1647      BLHB  0                                               D
END
```

Figure 9-29

FIGURE 10

```
         15      21.....28         39.....68         72.....90              104
HPV11            LLELYEE....KHIMHWKCIRLE.....KGHNA......EPWTLQDTSYEMWLT
                   (i)         (ii)           (iii)           (iv)

HPV6A            LLELYEE....KHVLHWKCMRHE.....KGHNA......EPWTLQETSYEMWQT
                   (i)          (v)           (iii)           (vi)

HPV16            ILTHYEN....DHIDYWKQMRLE.....KALQA......EKWTLQDVSLEVYLT
                  (vii)        (viii)          (ix)            (x)

HPV18            ILDHYEN....SQIQYWQLIRWE.....KAHKA......EDWTLQDTCEELWNT
                   (xi)         (xii)         (xiii)          (xiv)
```

Legend:

(i) SEQ ID NO.9; (ii) SEQ ID NO.10; (iii) SEQ ID NO.11; (iv) SEQ ID NO.12; (v) SEQ ID NO.13; (vi) SEQ ID NO.14; (vii) SEQ ID NO.15; (viii) SEQ ID NO.16; (ix) SEQ ID NO.17; (x) SEQ ID NO.18; (xi) SEQ ID NO.19; (xii) SEQ ID NO.20; (xiii) SEQ ID NO.21; and (xiv) SEQ ID NO.22

SEQUENCE LISTING

```
<160> NUMBER OF SEQ ID NOS: 22

<210> SEQ ID NO 1
<211> LENGTH: 220
<212> TYPE: PRT
<213> ORGANISM: HPV11

<400> SEQUENCE: 1

Met Glu Ala Ile Ala Lys Arg Leu Asp Ala Cys Gln Asp Gln Leu Leu
 1               5                  10                  15

Glu Leu Tyr Glu Glu Asn Ser Ile Asp Ile His Lys His Ile Met His
            20                  25                  30
```

```
Trp Lys Cys Ile Arg Leu Glu Ser Val Leu His Lys Ala Lys Gln
         35                  40                  45
Met Gly Leu Ser His Ile Gly Leu Gln Val Val Pro Pro Leu Thr Val
 50                  55                  60
Ser Glu Thr Lys Gly His Asn Ala Ile Glu Met Gln Met His Leu Glu
 65                  70                  75                  80
Ser Leu Ala Lys Thr Gln Tyr Gly Val Glu Pro Trp Thr Leu Gln Asp
                 85                  90                  95
Thr Ser Tyr Glu Met Trp Leu Thr Pro Pro Lys Arg Cys Phe Lys Lys
                100                 105                 110
Gln Gly Asn Thr Val Glu Val Lys Phe Asp Gly Cys Glu Asp Asn Val
                115                 120                 125
Met Glu Tyr Val Val Trp Thr His Ile Tyr Leu Gln Asp Asn Asp Ser
130                 135                 140
Trp Val Lys Val Thr Ser Ser Val Asp Ala Lys Gly Ile Tyr Tyr Thr
145                 150                 155                 160
Cys Gly Gln Phe Lys Thr Tyr Tyr Val Asn Phe Asn Lys Glu Ala Gln
                165                 170                 175
Lys Tyr Gly Ser Thr Asn His Trp Glu Val Cys Tyr Gly Ser Thr Val
                180                 185                 190
Ile Cys Ser Pro Ala Ser Val Ser Ser Thr Val Arg Glu Val Ser Ile
                195                 200                 205
Ala Glu Pro Thr Thr Tyr Thr Pro Ala Gln Thr Thr
                210                 215                 220

<210> SEQ ID NO 2
<211> LENGTH: 211
<212> TYPE: PRT
<213> ORGANISM: HPV11

<400> SEQUENCE: 2

Gly His His His His His Glu Ala Ile Ala Lys Arg Leu Asp Ala
  1               5                  10                  15
Cys Gln Asp Gln Leu Leu Glu Leu Tyr Glu Glu Asn Ser Ile Asp Ile
                 20                  25                  30
His Lys His Ile Met His Trp Lys Cys Ile Arg Leu Glu Ser Val Leu
             35                  40                  45
Leu His Lys Ala Lys Gln Met Gly Leu Ser His Ile Gly Leu Gln Val
 50                  55                  60
Val Pro Pro Leu Thr Val Ser Glu Thr Lys Gly His Asn Ala Ile Glu
 65                  70                  75                  80
Met Gln Met His Leu Glu Ser Leu Ala Lys Thr Gln Tyr Gly Val Glu
                 85                  90                  95
Pro Trp Thr Leu Gln Asp Thr Ser Tyr Glu Met Trp Leu Thr Pro Pro
                100                 105                 110
Lys Arg Cys Phe Lys Lys Gln Gly Asn Thr Val Glu Val Lys Phe Asp
                115                 120                 125
Gly Cys Glu Asp Asn Val Met Glu Tyr Val Val Trp Thr His Ile Tyr
130                 135                 140
Leu Gln Asp Asn Asp Ser Trp Val Lys Val Thr Ser Ser Val Asp Ala
145                 150                 155                 160
Lys Gly Ile Tyr Tyr Thr Cys Gly Gln Phe Lys Thr Tyr Tyr Val Asn
                165                 170                 175
Phe Asn Lys Glu Ala Gln Lys Tyr Gly Ser Thr Asn His Trp Glu Val
                180                 185                 190
```

-continued

```
Cys Tyr Gly Ser Thr Val Ile Cys Ser Pro Ala Ser Val Ser Ser Lys
        195                 200                 205
Lys Lys Lys
    210

<210> SEQ ID NO 3
<211> LENGTH: 57
<212> TYPE: DNA
<213> ORGANISM: HPV11

<400> SEQUENCE: 3
caagacgtgc gctagaccat gggacatcac catcaccatc acgaagcaat agccaag         57

<210> SEQ ID NO 4
<211> LENGTH: 42
<212> TYPE: DNA
<213> ORGANISM: HPV11

<400> SEQUENCE: 4
caccaagtgg atccgctagc ttagctagat acagatgcag ga                         42

<210> SEQ ID NO 5
<211> LENGTH: 58
<212> TYPE: DNA
<213> ORGANISM: HPV11

<400> SEQUENCE: 5
gggcgctaga ccatgggaca tcaccatcac catcacgaag caatagccaa gcgtttag        58

<210> SEQ ID NO 6
<211> LENGTH: 51
<212> TYPE: DNA
<213> ORGANISM: HPV11

<400> SEQUENCE: 6
ccccggatcc tcattacttt ttcttttttgc tagatacaga tgcaggagaa c              51

<210> SEQ ID NO 7
<211> LENGTH: 23
<212> TYPE: DNA
<213> ORGANISM: HPV11

<400> SEQUENCE: 7
gccCCTAACT CCGCCCATCC CGC                                              23

<210> SEQ ID NO 8
<211> LENGTH: 23
<212> TYPE: DNA
<213> ORGANISM: HPV11

<400> SEQUENCE: 8
accagaccgc cacggcttac ggc                                              23

<210> SEQ ID NO 9
<211> LENGTH: 7
<212> TYPE: PRT
<213> ORGANISM: HPV11

<400> SEQUENCE: 9

Leu Leu Glu Leu Tyr Glu Glu
  1               5
```

<210> SEQ ID NO 10
<211> LENGTH: 12
<212> TYPE: PRT
<213> ORGANISM: HPV11

<400> SEQUENCE: 10

Lys His Ile Met His Trp Lys Cys Ile Arg Leu Glu
 1               5                  10

<210> SEQ ID NO 11
<211> LENGTH: 5
<212> TYPE: PRT
<213> ORGANISM: HPV11

<400> SEQUENCE: 11

Lys Gly His Asn Ala
 1               5

<210> SEQ ID NO 12
<211> LENGTH: 15
<212> TYPE: PRT
<213> ORGANISM: HPV11

<400> SEQUENCE: 12

Glu Pro Trp Thr Leu Gln Asp Thr Ser Tyr Glu Met Trp Leu Thr
 1               5                  10                  15

<210> SEQ ID NO 13
<211> LENGTH: 12
<212> TYPE: PRT
<213> ORGANISM: HPV6A

<400> SEQUENCE: 13

Lys His Val Leu His Trp Lys Cys Met Arg His Glu
 1               5                  10

<210> SEQ ID NO 14
<211> LENGTH: 15
<212> TYPE: PRT
<213> ORGANISM: HPV6A

<400> SEQUENCE: 14

Glu Pro Trp Thr Leu Gln Glu Thr Ser Tyr Glu Met Trp Gln Thr
 1               5                  10                  15

<210> SEQ ID NO 15
<211> LENGTH: 7
<212> TYPE: PRT
<213> ORGANISM: HPV16

<400> SEQUENCE: 15

Ile Leu Thr His Tyr Glu Asn
 1               5

```
<210> SEQ ID NO 16
<211> LENGTH: 12
<212> TYPE: PRT
<213> ORGANISM: HPV16

<400> SEQUENCE: 16

Asp His Ile Asp Tyr Trp Lys Gln Met Arg Leu Glu
1               5                  10

<210> SEQ ID NO 17
<211> LENGTH: 5
<212> TYPE: PRT
<213> ORGANISM: HPV16

<400> SEQUENCE: 17

Lys Ala Leu Gln Ala
1               5

<210> SEQ ID NO 18
<211> LENGTH: 15
<212> TYPE: PRT
<213> ORGANISM: HPV16

<400> SEQUENCE: 18

Glu Lys Trp Thr Leu Gln Asp Val Ser Leu Glu Val Tyr Leu Thr
1               5                  10                  15

<210> SEQ ID NO 19
<211> LENGTH: 7
<212> TYPE: PRT
<213> ORGANISM: HPV18

<400> SEQUENCE: 19

Ile Leu Asp His Tyr Glu Asn
1               5

<210> SEQ ID NO 20
<211> LENGTH: 12
<212> TYPE: PRT
<213> ORGANISM: HPV18

<400> SEQUENCE: 20

Ser Gln Ile Gln Tyr Trp Gln Leu Ile Arg Trp Glu
1               5                  10

<210> SEQ ID NO 21
<211> LENGTH: 5
<212> TYPE: PRT
<213> ORGANISM: HPV18

<400> SEQUENCE: 21

Lys Ala His Lys Ala
1               5

<210> SEQ ID NO 22
<211> LENGTH: 15
<212> TYPE: PRT
<213> ORGANISM: HPV18

<400> SEQUENCE: 22

Glu Asp Trp Thr Leu Gln Asp Thr Cys Glu Glu Leu Trp Asn Thr
1               5                  10                  15
```

METHOD OF IDENTIFYING POTENTIAL INHIBITORS OF HUMAN PAPILLOMAVIRUS PROTEIN E2 USING X-RAY ATOMIC COORDINATES

RELATED APPLICATIONS

Benefit of U.S. Provisional Application, Ser. No. 60/304,412, filed on Jul. 12, 2001, is hereby claimed.

FIELD OF THE INVENTION

The invention relates to the papillomavirus E2 protein, particularly the crystalline structure of the human papillomavirus 11 (HPV-11) E2 protein transactivation domain complexed with an inhibitor. Particularly, the invention provides crystal structure coordinates that define an inhibitor-binding pocket and 3-dimension structural model for identifying potential inhibitors that would fit in this pocket. Also disclosed are methods for enabling the design and selection of inhibitors of E2 protein activity involved in papillomavirus DNA replication, particularly human papillomavirus.

BACKGROUND OF THE INVENTION

Papillomaviruses (PV) are non-enveloped DNA viruses that induce hyperproliferative lesions of the epithelia. The papillomaviruses are widespread in nature and have been recognized in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types of papillomavirus (HPV) that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases comprising cervical carcinomas (Fields, 1996, Virology, 3rd ed. Lippincott—Raven Pub., Philadelphia, N.Y.).

There are more than 25 HPV types that are implicated in anogenital diseases; these are grouped into "low risk" and "high risk" types. The low risk types include HPV type 6, and type 11, which induce mostly benign lesions such as condyloma acuminata (genital warts) and low grade squamous intraepithelial lesions (SIL). In the United States, there are approximately 5 million people with genital warts of which 90% is attributed to HPV-6 and HPV-11.

The high-risk types are associated with high grade SIL and cervical cancer and include most frequently HPV types 16, 18, 31, 33, 35, 45, and 52. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide (Fields, 1996, supra).

Treatments for genital warts include physical removal such as cryotherapy, $CO_2$ laser, electrosurgery, or surgical excision. Cytotoxic agents may also be used such as trichloroacetic acid (TCA), podophyllin or podofilox. Immunomodulatory agents are also available such as Interferon and imiquimod (Aldara®, 3M Pharmaceuticals). These treatments are not completely effective in eliminating all viral particles and there is either a high cost incurred or uncomfortable side effects related thereto. Also recurrent warts are common (Beutner & Ferenczy, 1997, Amer. J. Med., 102 (5A):28–37).

The ineffectiveness of the current methods to treat HPV infections has demonstrated the need to identify new means to control or eliminate such infections. In recent years, efforts have been directed towards finding antiviral compounds, and especially compounds capable of interfering with viral replication (Hughes and Romanos, 1993, Nucleic Acids Res. 21:5817–5823; Clark et al., Antiviral Res., 1998, 37(2):97–106; Hajduk et al., 1997, J. Med. Chem., 49(20): 3144–3150 and Cowsert et al., 1993, Antimicrob. Agents. Chemother., 37(2):171–177). To that end, it has therefore become important to study the genetics of HPVs in order to identify potential chemotherapeutic targets to contain and possibly eliminate any diseases caused by HPV infections.

The life cycle of PV is closely coupled to keratinocyte differentiation. Infection is believed to occur at a site of tissue disruption in the basal epithelium. Unlike normal cells, cellular division continues as the cell undergoes vertical differentiation. As the infected cells undergo progressive differentiation, the cellular replication machinery is maintained which allows viral DNA replication to increase, with eventual late gene expression and virion assembly in terminally differentiated keratinocytes and the release of viral particles (Fields, supra).

The coding strand for each of the papillomavirus genome contains approximately ten designated translational open reading frames (ORFs) that have been classified as either early ORFs or late ORFs. The E1 to E8 genes are expressed early in the viral replication cycle. The two late genes (L1 and L2) code for the major and minor capsid proteins respectively. The E1 and E2 gene products function in viral DNA replication, whereas E5, E6 and E7 modulate host cell proliferation. The functions of E3, E4 and E8 gene products are uncertain at present.

Studies of HPV have shown that proteins E1 and E2 are the only viral proteins required for viral DNA replication (Kuo et al., 1994, J. Biol. Chem. 30: 24058–24065). This requirement is similar to that of bovine papillomavirus type 1 (BPV-1). Indeed, there is a high degree of similarity between E1 and E2 proteins and the ori-sequences of all papillomaviruses (PV) regardless of the viral species and type (Kuo et al., 1994, supra).

When viral DNA replication proceeds in vitro, where E1 protein is present in excess, replication can proceed in the absence of E2. In vivo, in the presence of a vast amount of cellular DNA, replication requires the presence of both E1 and E2. The mechanism for initiating replication in vivo is believed to involve the cooperative binding of E1 and E2 to the origin, leading to the assembly of a ternary protein-DNA complex (Mohr et al., 1990, Science 250:1694–1699]. The E2 protein is a transcriptional activator that binds to the E1 protein and, by doing so enhances binding of E1 to the BPV origin of replication (Seo et al., 1993b, Proc. Natl. Acad. Sci., 90:2865–2869). Hence, E2 acts as a specificity factor in directing E1 to the origin of replication (Sedman and Stenlund, 1995, Embo. J. 14:6218–6228). In HPV, Lui et al. suggested that E2 stabilizes binding of E1 to the ori (1995, J. Biol. Chem. 270(45): 27283–27291 and McBride et al., 1991, J. Biol. Chem 266:18411–18414). These interactions of DNA-protein and protein-protein occur at the origin of DNA replication (Sverdrup and Myers, supra).

The ~45 kD E2 proteins characterized from numerous human and animal serotypes share a common organization of two domains. The N-terminal transactivation domain (TAD) is about 220 amino acids and the C-terminal DNA-binding domain (DBD) is 100 amino acids in length. Both domains are joined by a flexible linker region.

E2 activates viral replication through cooperative binding with the viral initiator protein E1 to the origin of DNA replication, ultimately resulting in functional E1 hexamers. E2 is also a central regulator of viral transcription. It interacts with basal transcription factors, including TATA-binding protein, TFIIIB, and human $TAF_{II}70$; proximal promoter binding protein such as Sp1; and other cellular factors such as AMF-1, which positively affect E2's transcriptional activation.

Which of these many interactions are sufficient or necessary to achieve transcriptional activation is more ambiguous. These details are consistent with the idea that enhancer binding proteins function as transcriptional activators by using specific protein-protein contacts to link components of the general transcription machinery to a promoter, with the goal of recruiting RNA polymerase II. A third function of E2 is to aid in the faithful segregation of viral DNA. The bovine papillomavirus (BPV) genome and E2 protein co-localize with host cell chromosomes during mitosis, dependent on an intact E2 TAD.

The E2 DBD dimerizes to form a β-barrel with flanking recognition helices positioned in the major grooves of the DNA binding site. In contrast, the structure of E2 TAD has remained elusive until Harris and Botchan (1999, Science, 284 (5420); 1673) provided a first model of a proteolytic fragment of HPV-18 E2 TAD by X-ray crystallography. The model suggests a cashew-shaped protein of 55 Å×40 Å×30 Å with a concave cleft on one side of the protein and ridges on the opposite surface. Harris and Botchan studied whether discrete surfaces correlated with known E2 activities and particularly identified a prominent cluster of residues constituting the inner edge of the main cavity encompassing E175, L178, Y179, and I73 defining a distinctive surface important for transcription.

Antson et al (2000, Nature, (403) 805–809) disclose the crystal structure of the complete E2 TAD from HPV-16, including a second newly identified putative E2—E2 TAD interface comprising a cluster of 7 conserved residues (R37, A69, I73, E76, L77, T81, and Q80). Anston et al suggested that Q12 and E39 may be involved in interaction with E1.

The E2 protein is considered a potential target for antiviral agents. However, drug discovery efforts directed towards E2 have been hampered by the lack of structural information of an E2 complexed with an inhibitor. Neither the model of Harris, nor that of Antson provides any information as to the localization and/or characterization of a potential inhibitor binding pocket. Structural information of the apo-E2 TAD has provided some valuable knowledge of the surface on the apo-protein but it now appears clear that this is not representative of the changes in conformation induced upon binding with an inhibitor.

The lack of specific E2 inhibitors, which is necessary for obtaining co-crystal of E2 and inhibitors, has hampered the search for the inhibitor binding pocket in E2. Thus, X-ray crystallographic analysis of such protein-inhibitor complex has not been possible.

The present invention refers to a number of documents, the contents of which are herein incorporated by reference.

SUMMARY OF THE INVENTION

The present invention provides a novel composition comprising a human papillomavirus E2 protein transactivation domain complexed with a small molecule inhibitor of E2 and methods for making such composition. Advantageously, the present invention further provides an E2-inhibitor complex that is capable of being crystallized and analyzed by X-ray diffraction, thereby providing important information on the inhibitor-binding pocket of the transactivation domain of the HPV E2 protein. The inhibitor provides an invaluable tool to produce a co-crystal allowing characterization of a previously unknown inhibitor-binding pocket that may be involved in interaction with E1 during the replication cycle of HPV.

The invention also provides a method for determining at least a portion of the three-dimensional structure of molecules or molecular complexes, which contains at least some structurally similar features to a HPV E2 inhibitor binding pocket.

The invention also provides a 3-D model for analyzing and predicting binding of potential inhibitors to aid in the search for further inhibitors binding to the identified pocket. Localization and characterization of this pocket, as described in the present invention provides a potential new therapeutic target in the treatment of PV infections.

The invention also provides a screening method for identifying agents capable of modulating this new target and a system to select at least one such agent capable of interfering with PV DNA replication.

The invention also provides a method for producing a drug, which inhibits interaction of the E1–E2 interaction comprising identifying a drug, or designing a drug that fits into the pocket as described herein.

According to a first aspect of the invention, there is provided a crystallizable composition, comprising an PV E2 TAD-like polypeptide of SEQ ID NO. 2 complexed with an inhibitor L:

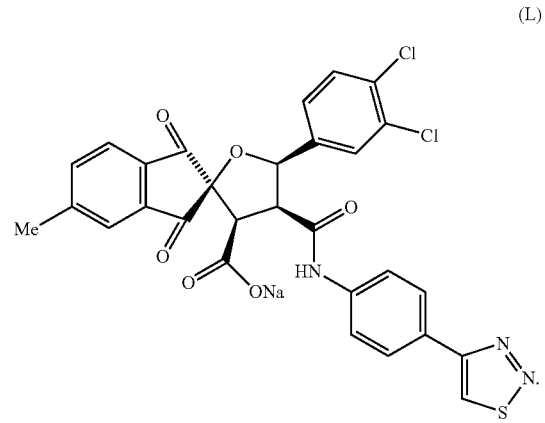

(L)

According to a second aspect of the invention, there is provided a crystal comprising an PV E2 TAD-like polypeptide of SEQ ID NO. 2 complexed with said inhibitor L, as defined above.

According to a third aspect of the invention, there is provided a method for producing a crystallized PV E2 TAD-inhibitor complex (PV E2 TAD-L), as defined above, comprising:

a) mixing purified PV E2 TAD, contained in a purification buffer, with solubilized inhibitor L to generate a complex solution containing said PV E2 TAD-L complex; and b) crystallizing said complex from a) in a crystallization buffer.

According to a fourth aspect of the invention, there is provided a method for producing crystallized apo PV E2 TAD, comprising:

a) mixing apo PV E2 TAD, contained in a purification buffer, with a crystallization buffer.

According to a fifth aspect of the invention, there is provided a method for producing a crystallized PV E2 TAD-inhibitor complex (PV E2 TAD-L), as defined above, comprising:

a) solubilizing inhibitor L in a crystallization buffer; and a) soaking crystallized apo PV E2 TAD, as defined above, into a).

According to a sixth aspect of the invention, there is provided X-ray crystal structure coordinates of PV E2 TAD-inhibitor complex (PV E2 TAD-L), as defined above.

According to a seventh aspect of the invention there is provided a computer-readable data storage medium comprising a data storage material encoded with the X ray crystal structure coordinates, or at least a portion of the structure coordinates, set forth in FIG. 9.

According to a eighth aspect of the present invention, there is provided a computer for generating a three dimensional representation of said PV E2 TAD-L complex, as defined herein, comprising:

a) a computer readable data storage medium having a data storage material encoded with said structure coordinates set forth in FIG. 9;

b) a memory for storing instructions for processing said computer readable data;

c) a central processing unit coupled to said computer readable data storage medium for processing said computer readable data into said three dimensional representation; and d) a display unit coupled to said central processing unit for displaying said three dimensional representation.

According to an ninth aspect of the invention, there is provided a method for producing an E2 protein, said protein being useful for identifying or characterizing E2 TAD inhibitors, comprising:

a) using the HPV E2 TAD-L crystal structure, as defined herein, to identify HPV inhibitor binding pocket residues;

b) comparing said HPV inhibitor binding pocket residues with analogous residues in another PV E2;

c) mutating said other PV residues to said HPV residues, to produce a hybrid; and d) testing said hybrid for inhibition by an inhibitor.

BRIEF DESCRIPTION OF THE DRAWINGS

Having thus generally described the invention, reference will now be made to the accompanying drawings, showing by way of illustration a preferred embodiment thereof, and in which:

FIG. 1A depicts the amino acid sequence of the HPV-11 E2 transactivation domain (SEQ ID NO. 1) as obtained by Sakai, et al. 1996, J Virol. V70 1602–11;

FIG. 1B depicts the amino acid sequence of the HPV-11 E2 transactivation domain (SEQ ID NO. 2) as obtained according to the procedure of Example 1;

FIG. 2 depicts stereo ribbon diagrams of the apo-E2 from HPV-16 as described in Antson et al. (supra);

FIG. 3 depicts stereo ribbon diagrams of the apo-E2 from HPV-11 as produced by the Applicant;

FIG. 4 depicts stereo ribbon diagrams of the E2 from HPV-11 complexed with compound L as described herein;

FIG. 5 depicts a solvent accessible surface representation of the inhibitor-binding pocket of the apo-E2 TAD from HPV-16 (Antson et al., supra);

FIG. 6A depicts a solvent accessible surface representation of the inhibitor-binding pocket of the apo-E2 from HPV-11 as produced by the Applicant;

FIG. 6B depicts a solvent accessible surface representation of the inhibitor-binding pocket of the co-crystal;

FIG. 7 depicts a schematic representation of the movement of Y19 and H32 occurring in the pocket upon binding with an inhibitor;

FIG. 8 depicts a solvent accessible surface top view of the pocket showing particularly a deep cavity and a shallow cavity;

FIG. 9 lists the atomic structure coordinates for the E2 TAD (SEQ ID NO 2) complexed with compound L as derived by X-ray diffraction from co-crystals of that complex (hereinafter referred to HPV TAD E2-L). The preparation of the complex is described in Example 3. The following terms have these meanings: the term A.A. refers to the amino acid which is identified by each coordinate, in this column: the term "CPR" means cis-proline; BLHA=first molecule of inhibitor L; BLHB=second molecule of inhibitor L. Information on amino acids 197 to 201 from chain A is lacking due to the high flexibility of those residues that renders them invisible to x-ray. For the same reason, the following amino acids are modeled as Alanine: E2, K107, K173, S180, M182, H183 and P196. "X, Y, Z" crystallographically define the atomic position determined for each atom in a Cartesian coordinate space. "Occ" is an occupancy factor that refers to the fraction of the molecules in which each atom occupies the position specified by the coordinates. A value of "1" indicates that each atom has the same conformation, e.g., the same position, in all molecules of the crystal. "B" is a thermal factor that measures movement of the atom around its atomic center. The coordinates of the residues that form the deep cavity are shown in bold; and FIG. 10 depicts the alignment of the amino acid sequence clusters that define generally the inhibitor-binding pocket region of the E2 transactivation domain from HPV-6A, HPV-11, HPV-16 and HPV-18. The residues in bold indicate that they define the deep cavity of the inhibitor binding pocket. The single underline defines the residues of the bottom of the deep pocket. The double underline indicates the shallow pocket residues. Y19 is indicated in italics.

DETAILED DESCRIPTION OF THE INVENTION

Definitions

The following abbreviations are used throughout the specification.

The term "associating with" or "binding" refers to a condition of proximity between chemical entities or compounds, or portions thereof. The association may be non-covalent—wherein the juxtaposition is energetically favored by hydrogen bonding or van der Waals or electrostatic interactions—or it may be covalent.

The term "binding pocket", as used herein, refers to a region of a molecule or molecular complex, that, as a result of its shape, favorably associates with another molecule, molecular complex, chemical entity or compound. As used herein, the pocket comprises at least a deep cavity and, optionally a shallow cavity.

As used herein the term "complex" refers to the combination of a molecule or a protein, conservative analogs or truncations thereof associated with a chemical entity.

The abbreviations for the α-amino acids used in this application are set forth as follows:

| Amino Acid | Symbol | Single letter code |
|---|---|---|
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "analog" as used herein denotes, in the context of this invention, a sequence of amino acid that retains a biological activity (either functional or structural) that is substantially similar to that of the original sequence. This analog may be from the same or different species and may be a natural analog or be prepared synthetically. Such analogs include amino acid sequences having substitutions, deletions, or additions of one or more amino acids, provided that the biological activity of the protein is conserved. Particularly, the term "conservative analog" denotes an analog having amino acid substituted by another amino acid having strong or weak similarity (see, for example, Dayhoff, M. O., (1978), Atlas of Protein Sequence and Structure, 5, suppl. 3, National Biomedical Research Foundation, Washington, D.C.) as defined according to the following Table:

Table of amino acid similarity

| Amino acid | Strong | Weak |
|---|---|---|
| A | G, S | C, T, V |
| C | | A, S |
| D | E | G, H, K, N, Q, R, S |
| E | D | H, K, N, Q, R, S |
| F | W, Y | H, I, L, M |
| G | A | D, N, S |
| H | Y | D, E, F, K, N, Q, R |
| I | L, M, V | F |
| K | R | D, E, H, N, Q, S, T |
| L | I, M, V | F |
| M | I, L, V | F |
| N | Q | D, E, G, H, K, R, S, T |
| P | | S, T |
| Q | N | D, E, H, K, R, S |
| R | K | D, E, H, N, Q |
| S | A, T | C, D, E, G, K, N, P, Q |
| T | S | A, K, N, P, V |
| V | I, L, M | A, T |
| W | F, Y | |
| Y | F, H, W | |

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "truncation" refers to any segment of the E2 TAD amino acid sequence and/or any segment of any of the analogs described herein above that comprise the amino acids sufficient to define the deep cavity of the inhibitor-binding pocket of the present invention in the same spatial relationship as the one defined by the coordinates of FIG. 9.

The term "root mean square deviation" or "rms deviation" or "rmsd" means the square root of the arithmetic mean of the square of the deviations from the mean. In the context of atomic objects, the numbers are given in angstroms (Å). It is a way to express the deviation or variation from a trend or object. For the purpose of the present invention, all rmsd comparison were obtained by comparing structures that had been superimposed using the main chain atoms of H32, W33 and L94 only, to the minimum overlap rms, by rigid body movement only. The main chain atom rmsd for this action between our apo structure and the complex disclosed herein is 0.078 Å.

PREFERRED EMBODIMENTS

1. Composition

According to a first embodiment, there is provided a crystallizable composition, comprising an HPV E2 TAD-like polypeptide of SEQ ID NO. 2 complexed with an inhibitor L:

(L)

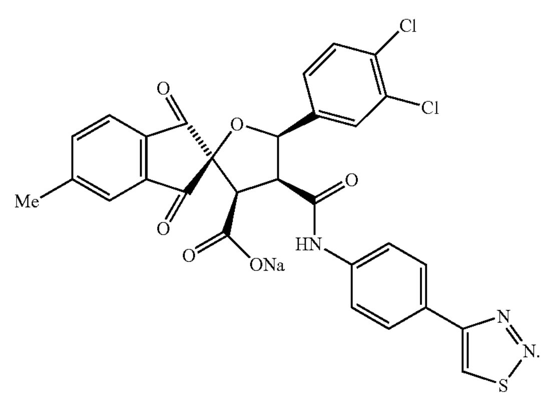

Preferably, the composition comprises amino acids 1–220 of the HPV E2 protein (SEQ ID NO. 1) as defined according to the numbering of Swiss Prot: locus VE2_HPV11 accession P04015; unique ID: g137671, conservative analogs or truncations thereof. More preferably, the trans-activation domain (TAD) of E2 comprises amino acids 1–218, particularly 1–215 and even more preferably 1–201. Still, most preferably, the E2 TAD used for the present invention comprises amino acids 2–201 and still most particularly 2–196. Even most preferably, the composition comprises amino acids 15–104 of the E2 TAD.

In another aspect of the first embodiment, the HPV E2 TAD used for the present invention is obtained from the HPV-11 strain and is complexed with the small molecule inhibitor L. Other types of papillomavirus (PV) are also contemplated by the present invention, including BPV (bovine papillomavirus) or CRPV (Cotton Tail Rabbit Papilloma Virus).

According to a second embodiment, there is provided a crystal comprising an HPV E2 TAD-like polypeptide of SEQ ID NO. 2 complexed with the inhibitor L.

2. Method of Crystallizing

According to a third embodiment of the invention, there is provided a method for producing a crystallized HPV E2 TAD-inhibitor complex (HPV E2 TAD-L), as defined above, comprising:
  a) mixing purified HPV E2 TAD, contained in a purification buffer, with solubilized inhibitor L to generate a complex solution containing said HPV E2 TAD-L complex; and
  b) crystallizing said complex from a) in a crystallization buffer.

In a preferred aspect of the third embodiment step a), the inhibitor L is solubilized in 100% DMSO at a concentration of 60 mM.

In a preferred aspect of the third embodiment step a), the purification buffer contains a reducing agent that may be selected from TCEP or DTT. More preferably the reducing agent is TCEP. Preferably, the reducing agent is TCEP at a concentration of about 1 mM to about 10 mM. More preferably, the reducing agent is TCEP at a concentration of 5 mM.

Preferably, the purification buffer is used at a pH of between 7 and 9. More preferably, the purification buffer is used at pH of 8.

Further to the reducing agent, a salt can be added to aid stability of the HPV E2 TAD. Preferably, the salt may be selected from NaCl, $NH_4SO_4$, or KCl. More preferably, the salt is NaCl at a concentration of about 200 mM to about 800 mM. More preferably, the salt is NaCl at a concentration of 500 mM.

Further to the reducing agent, a buffer can be added to further aid the stability of the HPV E2 TAD. Preferably, the buffer may be selected from Tris-HCl, HEPES or bis-Tris. More preferably, the buffer is Tris-HCl at a concentration of between 0 nM and 50 mM. Most preferably, the buffer is Tris-HCl at a concentration of 25 nM.

Further to the reducing agent, a chelating agent may be added to reduce degradation of HPV E2 TAD by proteases. Preferably, the chelating agent may be EDTA or EGTA. More preferably, the chelating agent is EDTA at a concentration of between 0 mM and 1 mM. Even more preferably, the chelating agent is EDTA at a concentration of between 0 mM and 0.5 mM. Most preferably, the chelating agent is EDTA at a concentration of 0.1 mM.

In a preferred aspect of the third embodiment step a), preferably the HPV E2 TAD protein solution is used at a concentration of about 5 mg/ml to about 15 mg/ml in the purification buffer. More preferably, the HPV E2 TAD is used at a concentration of about 10 mg/ml HPV E2 TAD in the purification buffer.

In a preferred aspect of the third embodiment step b), preferably the crystallization buffer may be selected from MES, sodium phosphate, potassium phosphate, sodium acetate or sodium succinate. More preferably, the crystallization buffer is MES at a concentration of about 50 mM to about 0.2M. Most preferably, the crystallization buffer is MES at a concentration of 0.1M.

Preferably, the crystallization buffer further contains a precipitating agent, which aids crystallization of the HPV E2 TAD. Preferably, the precipitating agent may be selected from MPD, isopropanol, ethanol, or tertiary butanol. More preferably, the precipitating agent is MPD at a concentration of 30% to about 40%. Most preferably, the precipitating agent is MPD at a concentration of 35%.

Preferably, the crystallization buffer is used at a pH of between 4.5 and 6.5. Most preferably, the crystallization buffer is used at a pH of 5.5

In a preferred aspect of the third embodiment step b), the crystallization is carried out at between 0° C. and 10° C. More preferably, the crystallization is carried out at 4° C.

In a preferred aspect of the third embodiment, crystallization of the HPV E2 TAD-L complex was carried out using the hanging drop vapor diffusion technique.

In an important aspect of the third embodiment, the crystallized HPV E2 TAD-L complex invention is amenable to X-ray crystallography. Using X-ray crystallography analysis, the HPV E2 TAD-inhibitor complex crystals obtained belong to space group P4(1) with unit cell dimension of a=b=60.7 Å and c=82.5 Å and contain one molecule per asymmetric unit. Initial diffraction data were measured using a home source x-ray generator (Rigaku, Japan) equipped with an R-axis II image plate area detector (Molecular Structure Corp, Texas). Preferably, data to a resolution of 3.15 Å were collected on a single crystal of the complex cooled at 100 K.

According to a fourth embodiment of the invention, there is provided a method for producing crystallized apo HPV E2 TAD, comprising:
  a) mixing apo HPV E2 TAD, contained in a purification buffer, with a crystallization buffer.

In a preferred aspect of the fourth embodiment, the apo HPV E2 TAD is apo HPV-11 E2 TAD. More preferably, the apo HPV E2 TAD is apo Se-HPV-11 E2 TAD.

In a preferred aspect of the fourth embodiment, the purification buffer contains is as described herein. Preferably, the apo HPV E2 TAD protein solution is used at a concentration of about 1 mg/ml to about 15 mg/ml in the purification buffer. More preferably, the apo HPV E2 TAD is used at a concentration of about 1 mg/ml to about 10 mg/ml E2 TAD in the purification buffer. Most preferably, the apo HPV E2 TAD is used at a concentration of 5 mg/ml in the purification buffer.

In a preferred aspect of the fourth embodiment, the crystallization buffer may be selected from MES, sodium phosphate, potassium phosphate, sodium acetate or sodium succinate. More preferably, the crystallization buffer is sodium succinate at a concentration of about 50 mM to about 0.2M. Most preferably, the crystallization buffer is sodium succinate at a concentration of 0.1M.

Preferably, the crystallization buffer further contains PEG8K, PEG4K or PEG5K mono methyl ether. More preferably, the crystallization buffer further contains PEG5K mono methyl ether at a concentration of about 10% to about 25%. Most preferably, the crystallization buffer further contains PEG5K mono methyl ether at a concentration of 18%.

Preferably, the crystallization buffer is used at a pH of between 4.5 and 6.5. Most preferably, the crystallization buffer is used at a pH of 5.0

Preferably, the crystallization buffer further contains ammonium sulfate at a concentration of about 0.1M to about 0.4M. Most preferably, the crystallization buffer further contains ammonium sulfate at a concentration of 0.2M.

In a preferred aspect of the fourth embodiment step, the crystallization is carried out at between 0° C. and 10° C. More preferably, the crystallization is carried out at 4° C.

The apo HPV-11 E2 TAD crystals belong to space group C222 with unit cell dimension of a=54.9 Å, b=169.9 Å and c=46.1 Å and contained one molecule per asymmetric unit. Diffraction data were collected on beamline X4a (NSLS, Brookhaven National Laboratory, New York). Four data sets were collected form a single crystal cooled at 100 K, at four different x-ray wavelengths near the selenium absorption edge (0.9790 Å, 0.9794 Å, 0.9743 Å, and 0.9879 Å). Images were collected on a ADSC Q4 CCD. Preferably, the maximum resolution was 2.4 Å.

According to a fifth embodiment of the invention, there is provided a method for producing a crystallized HPV E2 TAD-inhibitor complex (HPV E2 TAD-L), as defined above, comprising:
  a) solubilizing inhibitor L in a crystallization buffer; and
  b) soaking crystallized apo HPV E2 TAD, as defined above, into a).

In an alternative aspect of the fifth embodiment of the invention, there is provided a method for producing a crystallized HPV E2 TAD-inhibitor complex (HPV E2 TAD-L), as defined above, comprising:
  a) adding inhibitor L into a crystallization buffer containing crystallized HPV E2 TAD.

3. X-ray Coordinates

According to a sixth embodiment, there is provided X-ray crystal structure coordinates of the HPV E2 TAD-inhibitor complex (HPV E2 TAD-L), as defined above. More preferably, the coordinates are of the inhibitor-binding pocket. Even more preferably, the set of coordinates for the HPV E2 TAD-inhibitor complex are defined according to FIG. 9.

Preferably, the inhibitor-binding pocket comprises a deep cavity which is delimited by the side chains of amino acids H32, W33 and L94, wherein the side chain of Y19 of the HPV E2 TAD is moved away from its native position to form a deep cavity of such dimensions as to allow entry of a small molecule inhibitor. More preferably, the deep cavity is lined at its bottom by amino acids H29 and T97. Most preferably, the pocket further comprises a shallow cavity that is delimited by one or more of amino acids L15, I36, E39, K68, N71 and A72.

Preferably, the inhibitor-binding pocket is defined according to the coordinates assigned to the following clusters of amino acids:

More preferably, the inhibitor-binding pocket and particularly its deep cavity is defined by the coordinates of H32, W33 and L94 according to FIG. 9. More preferably, the coordinates of the side chains of H32, W33 and L94.

Alternatively, one may consider changing the side chain of Y19 from a protein construct that would reproduce a similar deep cavity without the hindrance of the Y19 side chain.

Even more preferably, the bottom of the deep pocket is defined by the coordinates of amino acids H29 and T97. Even most preferably, the shallow cavity of the inhibitor-binding pocket is defined by the coordinates of one or more of amino acids L15, I 36, E39, K68, N71 and A72.

The three-dimensional structure of the HPV E2 TAD-L complex of this invention is defined by a set of structure coordinates as set forth in FIG. 9. The term "structure coordinates" refers to Cartesian coordinates derived from mathematical operations related to the patterns obtained on diffraction of a monochromatic beam of X-rays by the atoms (scattering centers) of an E2-L complex in crystal form. The diffraction data are used to calculate an electron density map of the repeating unit of the crystal. The electron density maps are then used to establish the positions of the individual atoms of the E2 TAD inhibitor pocket.

Those of skill in the art will understand that a set of structure coordinates for a protein or protein-inhibitor complex or a portion thereof, is a relative set of points that define a shape in three dimensions. Thus, it is possible that an entirely different set of coordinates could define a similar or identical shape.

The variations in coordinates may be generated by mathematical manipulations of the structure coordinates. For example, the structure coordinates set forth in FIG. 9 could be manipulated by crystallographic permutations of the structure coordinates, fractionalization or matrix operations to sets of the structure coordinates or any combination of the above.

Various computational analyses are necessary to determine whether a molecule or molecular complex or a portion thereof is sufficiently similar to all or parts of the HPV E2 protein or HPV E2 TAD described above as to be considered the same. Such analyses may be carried out in current software applications, such as the Molecular Similarity application of QUANTA (Molecular Simulations Inc., San Diego, Calif.) version 4.1.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalence in these structures; 3) perform a fitting (superposition) operation; and 4) analyze the results.

Each structure is identified by a name. One structure is then identified as the target (i.e., the fixed structure); all remaining structures are working structures (i.e., moving structures). Since atom equivalency within QUANTA is defined by user input, for the purpose of this invention rmsd

```
15      21.....28         39....68    72......90           104
LLELYEE ..... KHIMHWKCIRLE .... KGHNA ....... EPWTLQDTSYEMLT
(SEQ ID NO.9) (SEQ ID NO.10)    (SEQ ID NO.11)   (SEQ ID NO.18)
``` values were determined using main chain atoms for amino acids H32, W33 and L94 between the two structures being compared.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. After superposition of the two structures, a rmsd value can be calculated for specific sets of equivalent atoms.

4. Coordinates Stored on Machine Readable Medium

In a seventh embodiment, there is provided a computer-readable data storage medium comprising a data storage material encoded with the structure coordinates, or at least a portion of the structure coordinates set forth in FIG. 9. Examples of such computer readable data storage media are well known to those skilled in the art and include, for example CD-ROM and diskette ("floppy disks").

Thus, in accordance with the present invention, the structure coordinates of a HPV E2-inhibitor complex, and in particular a HPV E2 TAD-L complex, and portions thereof can be stored in a machine-readable storage medium. Such data may be used for a variety of purposes, such as drug discovery and X-ray crystallographic analysis of protein crystal.

Accordingly, in an eighth embodiment, there is provided a computer for generating a three dimensional representation of the HPV E2 TAD-L complex, comprising:
 a) a computer readable data storage medium comprising a data storage material encoded with the structure coordinates set forth in FIG. 9;
 b) a memory for storing instructions for processing said computer readable data;
 c) a central processing unit coupled to said computer readable data storage medium for processing said computer readable data into said three dimensional representation; and
 d) a display unit coupled to said central processing unit for displaying said three dimensional representation.

5. 3-Dimensional Structure of Pocket

The invention also provides a 3-dimensional structure of at least a portion of the molecular complex, which contains features structurally similar to a HPV E2 TAD inhibitor binding pocket.

Figure 7:
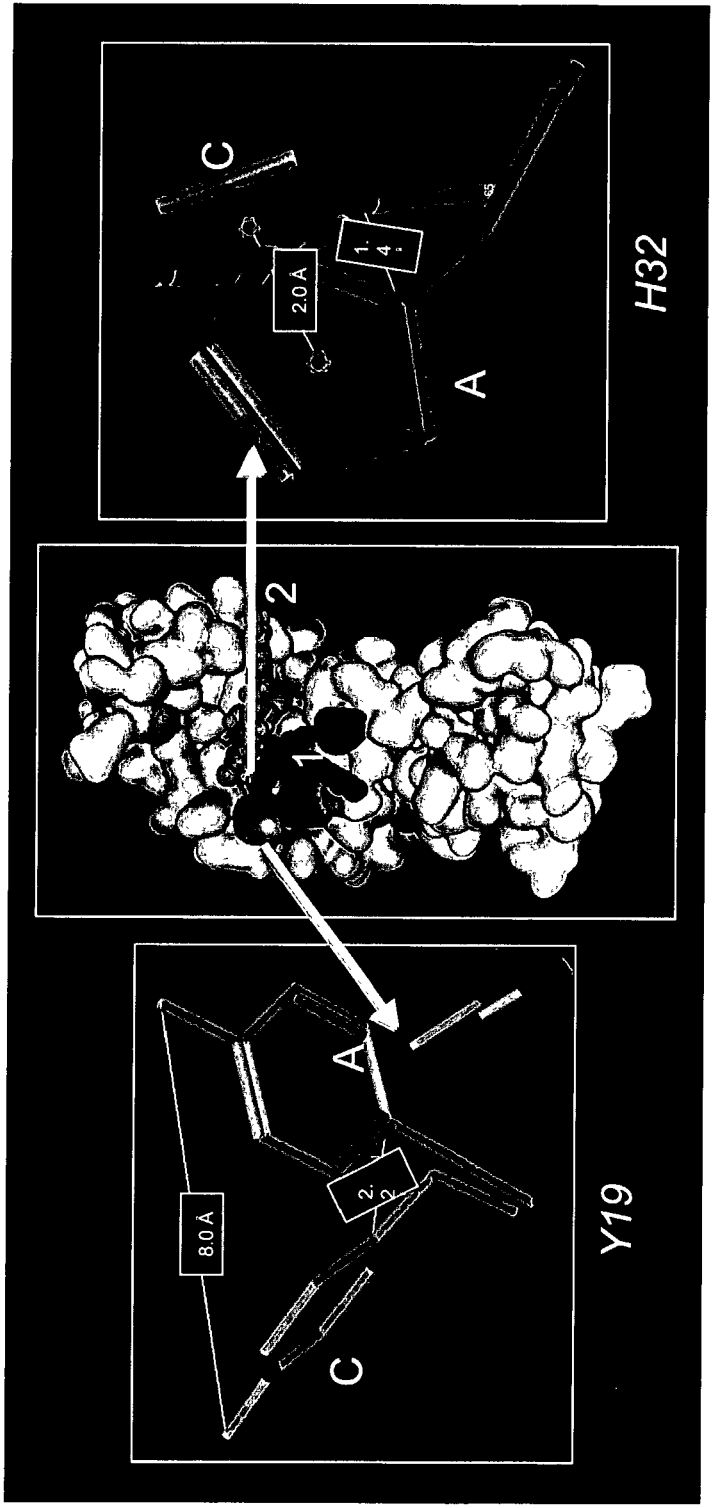

The shape of the inhibitor binding pocket, according to the present invention, can be viewed as comprising a deep pocket and, optionally, a shallower pocket (see FIG. 7). The shape of the deep cavity is defined by the relative positions of the side chains of amino acids H32, W33 and L94 and not their absolute coordinates according to FIG. 9. Similar coordinates or three-dimensional model may be obtained from different techniques (e.g. NMR, modeling, etc.) and are considered to fall within the scope of the present invention.

Thus, this invention also provides the three-dimensional structure of an HPV E2-inhibitor complex, specifically an HPV E2 TAD-L complex. Importantly, this has provided for the first time, information about the shape and structure of this HPV E2 TAD inhibitor-binding pocket.

6. Using the Three-dimensional Model for Screening

In a ninth embodiment, there is provided a method for evaluating the potential of a chemical entity to associate with a papillomavirus E2 transactivation domain comprising a binding pocket defined by the structure coordinates of an HPV-11 E2 protein transactivation domain comprising amino acids H32, W33 and L94, or a three-dimensional model thereof.

Optionally, the invention further provides for the same method where the binding pocket further comprises the structure coordinates of one or both of H29 and T97 that define the bottom of the deep pocket.

Optionally, the invention further provides for the same method where the binding pocket further comprises the structure coordinate of at least one amino acid selected from the group consisting of: L15, I36, E39, K68, N71 and A72.

For the first time, the present invention permits the use of structure-based or rational drug design techniques to design, select, and synthesize chemical entities, including inhibitory compounds that are capable of fitting and/or binding to HPV E2 TAD inhibitor binding pocket, or any portion thereof.

One particularly useful drug design technique enabled by this invention is iterative drug design. Iterative drug design is a method for optimizing associations between a protein and a compound by determining and evaluating the three-dimensional structures of successive sets of protein/compound complexes.

Those of skill in the art will realize that association of natural ligands or substrates with the binding pocket of their corresponding receptors or enzymes is the basis of many biological mechanisms of action. Similarly, many drugs exert their biological effects through association with the binding cavities of receptors and enzymes. Such associations may occur with all or any parts of the binding pocket. An understanding of such associations will help lead to the design of drugs having more favorable associations with their target receptor or enzyme, and thus, improved biological effects. Therefore, this information is valuable in designing potential ligands or inhibitors of receptors or enzymes, such as inhibitors of HPV E2-like polypeptides, and more importantly HPV E2 TAD.

In iterative drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, as described above, thereby forming a protein/compound complex and obviating the need to crystallize each individual protein/compound complex. Advantageously, the HPV E2 protein crystals, and in particular the E2 TAD crystals, provided by this invention may be soaked in the presence of an inhibitor or in particular an E2 inhibitor, such as compound L, to provide E2-inhibitor crystal complexes, as described above.

7. Using the Pocket for Screening

In certain instances, one may be able to engineer an E2 TAD lacking the side chain of Y19 to reproduce the inhibitor-binding pocket as defined herein. Such modifications of the primary sequence to achieve a similar binding pocket is intended to be within the scope of the present invention. Also covered is the use of such a modified E2 TAD for screening purposes (either by NMR, MS, probe displacement assays, etc.) to screen for potential inhibitor of the newly defined pocket.

8. Alteration of Cottontail Rabbit Papillomavirus (CRPV) E2 for Efficient Binding of Inhibitors In tenth embodiment, there is provided a method for producing an E2 protein, said protein being useful for identifying or characterizing E2 TAD inhibitors, comprising:

a) using the HPV E2 TAD-L crystal structure, as defined above, to identify HPV inhibitor binding pocket residues;
b) comparing said HPV inhibitor binding pocket residues with Cottontail Rabbit Papilloma Virus (CRPV) protein residues;
c) mutating said CRPV residues to said HPV residues, to produce a hybrid; and
d) testing said hybrid for inhibition by an inhibitor.

Infection of laboratory rabbits with cottontail rabbit papillomavirus (CRPV) or introduction of the CRPV genome into the skin of these rabbits results in the growth of large warts. The CRPV model system has been used to evaluate potential anti-HPV treatments (Kreider, J. W., et al. (1992) "Preclinical system for evaluating topical podofilox treatment of papillomas: dose response and duration of growth prior to treatment" *J. Invest. Dermatol.* 99, 813–818.). One can envisage that this would constitute a convenient system for testing the in vivo efficacy of E2-binding HPV DNA replication inhibitors. However, the CRPV and HPV E2 proteins share only 39% sequence identity and inhibitors which bind to the HPV protein may not bind to CRPV E2.

The HPV E2 TAD-inhibitor crystal structure, as described herein, can be used to identify residues, which are members of the HPV inhibitor binding pocket and which differ in the CRPV protein. The corresponding CRPV residues can then be mutated to the HPV counterpart. The resulting hybrid can be tested by in vitro translation of the hybrid gene to produce an E2 protein which could be tested in vitro assays, such as the E2-dependent E1-DNA binding assay (see Example 6). If the hybrid protein is functional in the assay, and proves to be sensitive to HPV inhibitors, the corresponding gene can be used to induce the growth of warts on rabbits. Warts resulting from this procedure should be treatable by inhibitors originally targeted to HPV E2. Thus use of this hybrid model, generated by analysis of the HPV TAD inhibitor complex, could be used to test HPV compounds in an animal model. This technique may also be applicable to other papilloma viruses such as, but limited to, bovine papilloma virus (BPV).

In order that this invention be more fully understood, the following examples are set forth. These examples are for the illustrative purposes only and are not to be construed as limiting the scope of this invention in any way.

EXAMPLES

Example 1

Expression and Purification of HPV-11 E2 TAD

Expression of His-tagged HPV-11 E2 transactivation domain. Amino acids 2–201 of HPV-11 E2 (SEQ ID NO. 2) were amplified by PCR from plasmid pCR3-E2 (Titolo, 1999) using the primers 5'-CAA GAC GTG CGC TAG ACC ATG GGA CAT CAC CAT CAC CAT CAC GAA GCA ATA GCC AAG-3'(sense) (SEQ ID NO. 3) and 5'-CAC CAA GTG GAT CCG CTA GCT TAG CTA GAT ACA GAT GCA GGA-3' (antisense) (SEQ ID NO. 4). The PCR product was digested using NcoI and BamHI and ligated into plasmid pET-28b, which had been similarly digested. The ligation product was transformed into MAX Efficiency® competent DH5α *E. coli* (Life Technologies). Recombinant plasmid encoding His-tagged HPV11 E2 TAD (His-TAD) was isolated from a culture of the transformed DH5α, and the DNA sequence of the E2 TAD was verified to be correct. The isolated plasmid was then transformed into *E. coli* strain BL21(DE3)pLysS (Novagen).

A second construct encoding an additional four lysines placed at the C-terminus of the E2 transactivation domain (Lys-tailed TAD) was generated by pcr using the sense primer 5'-GGG CGC TAG ACC ATG GGA CAT CAC CAT CAC CAT CAC GAA GCA ATA GCC AAG CGT TTA G-3' (SEQ ID NO. 5) and the anti sense primer 5'-CCC CGG ATC CTC ATT ACT TTT TCT TTT TGC TAG ATA CAG ATG CAG GAG AAC-3' (SEQ ID NO. 6). This PCR product was digested as above and ligated into plasmid pET15b. The DNA sequence encoding for HPV11 E2 amino acids 2–201 was verified to be correct, and the plasmid was transformed into *E. coli* strain BL21 (DE3)pLysS as described above.

For protein expression, CircleGrow medium (Bio101) containing 34 μg/mL chloramphenicol and 50 μg/mL kanamycin (His-TAD) or 100 μg/mL ampicillin (Lys-tailed TAD) was inoculated with one-twenty fifth volume of a fresh overnight culture and cells were grown at 37° C. until an O.D.(600 nm) of approximately 1.0 was reached. The culture was then shifted to 22° C. and protein expression was induced at O.D.(600 nm)=1.4 with 0.5 mM IPTG. After six hours, cells were harvested by centrifugation and frozen on dry ice, then stored at −80° C.

Purification of His-tagged HPV11 TAD proteins. The purification procedure was identical for the His-tagged TAD and Lys-tailed TAD proteins; all steps were performed at 4° C. Cells were resuspended at 5 mL per gram in purification buffer (25 mM Tris-HCl pH 8.0, 500 mM NaCl, 5 mM TCEP) plus protease inhibitors pepstatin, leupeptin, and antipain (each at 5 μg/ml), phenylmethylsulfonyl fluoride (1 mM), and Pefabloc® (Roche, 0.4 mM). The suspension was sonicated, and the crude lysate was centrifuged for 30 min at 26,000 g. The supernatant was injected onto a 5 mL Hi-Trap chelating column (APB) equilibrated with nickel sulfate. After washing with purification buffer plus 0 mM and 25 mM imidazole, TAD was eluted with purification buffer containing 100 mM imidazole. TAD-containing fractions were pooled and concentrated to less than 5 mL, then loaded onto a Superdex-75 gel filtration column (APB) equilibrated with purification buffer plus 0.1 mM EDTA. Fractions containing pure TAD were pooled and concentrated to approximately 5 mg/mL (His-tagged TAD) or 12 mg/mL (Lys-tailed TAD). Concentrated protein was aliquoted, frozen on dry ice, and stored at −80° C.

Expression and purification of His-TAD containing selenomethionine. The plasmid encoding His-TAD was transformed into *E. coli* strain B834 (auxotrophic for methionine). A single bacterial colony was used to inoculate an overnight culture in LB medium containing 34 μg/mL chloramphenicol and 50 μg/mL kanamycin. A portion of this culture was diluted 4000-fold in DL30 medium (D. M. LeMaster and R. M. Richards, Biochemistry (1985) v24, 7263–68), lacking methionine and supplemented with 2 μg/mL biotin and thiamin and 50 μg/mL D,L-selenomethionine and the same antibiotics. After 26 hours at 37° C., the culture had reached a density of 0.8 (O.D. 600 nm), and expression was induced at 23° C. with 0.5 mM IPTG. After approximately seven hours, cells were harvested and stored as described above. Purification was performed as described above for His-TAD, except that purification buffers were sparged with helium before use,and His-TAD was eluted with 200 mM imidazole after washes at 50 and 100 mM.

Example 2
Synthesis and Purification of Compound L
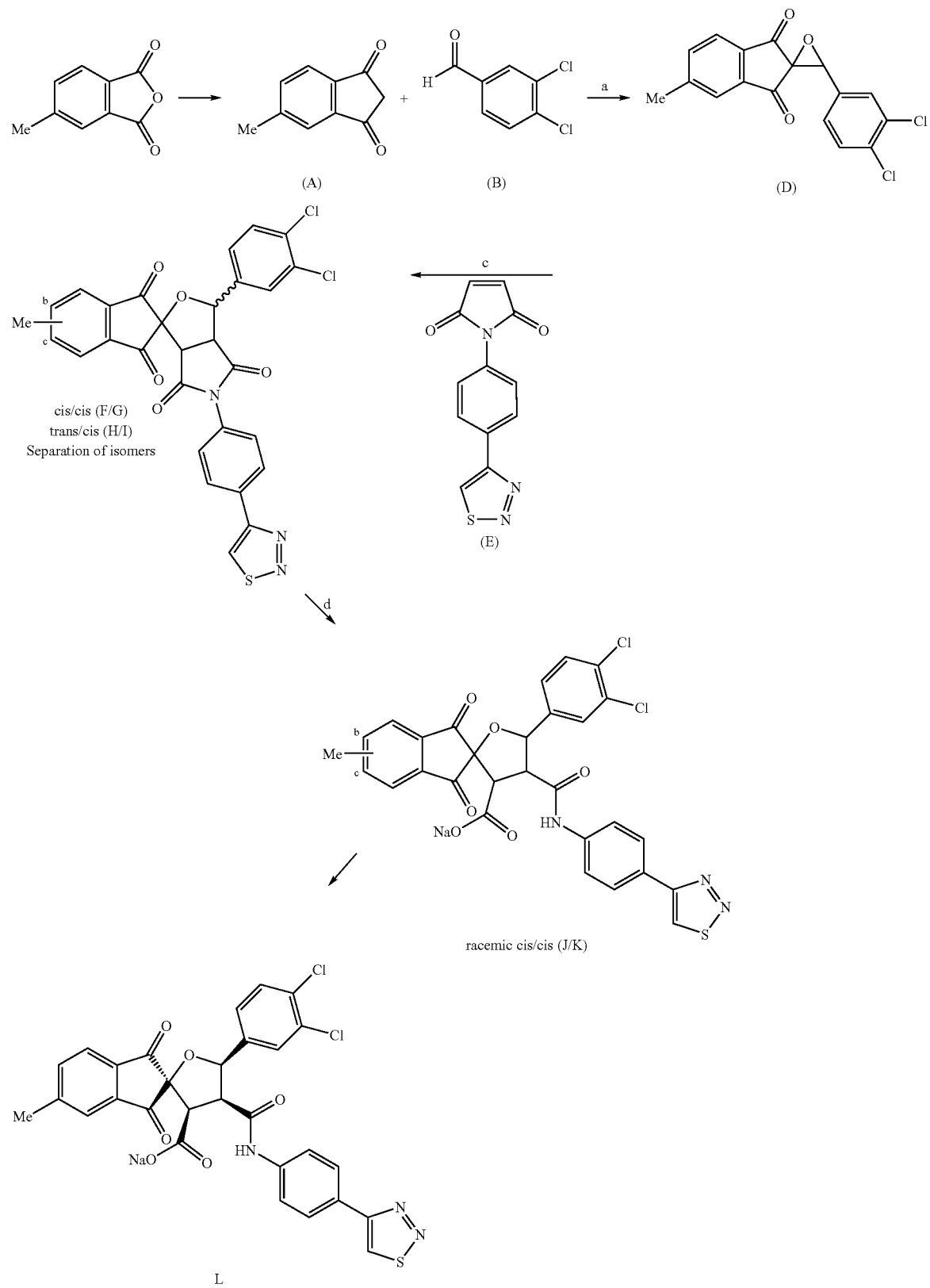

5-Methyl 1,3-indanedione (A)

To a suspension of 4-methyl phthalic anhydride (25.65 g, 158.2 mmol) in MeOH (79 mL) at room temperature, was added sodium methoxide (69 mL of 25% wt solution, 316 mmol). After 30 min. the reaction mixture was diluted with water and the aqueous layer was washed with Et$_2$O. The aqueous layer was acidified with HCl (4N) and extracted with Et$_2$O. The organic layer was rinsed with brine, dried (MgSO$_4$), filtered and concentrated under reduced pressure.

The crude residue was dissolved in acetonitrile (79 mL) and cooled to 0° C. To the resulting solution was added successively DBU (31.3 g, 206 mmol), and iodomethane (33.7 g, 237.3 mmol). After 1 hour at 0° C., iodomethane (33.7 g, 237.3 mmol) was added and the reaction was warmed to room temperature and stirred for a further hour. The reaction mixture was concentrated under reduced pressure, and the residue was diluted with Et$_2$O (300 mL). The ethereal solution was washed successively with aqueous HCl (4N, 100 mL), NaOH (10%) and Brine, dried (MgSO4), filtered and concentrated to dryness. The resulting residue was treated with an ethereal solution of diazomethane to complete the esterification, after which was concentrated to give the 4-methyl dimethyl phtalate (22.2 g, 67% yield) as a pale yellow oil.

To a solution of crude 4-methyl dimethyl phthalate (22.20 g, 106.6 mmol) in ethyl acetate (107 mL), was added sodium hydride (97%, 3.84 g, 160 mmol). The resulting suspension was heated to reflux for 4.5 hours followed by cooling to room temperature and Et$_2$O (100 mL) addition to give a yellow precipitate. The yellow solid was filtered and washed twice with a mixture of ethyl alcohol/diethyl ether (1/1).

This yellow solid was then dissolved in HCl (4N, 100 mL) and heated to reflux for 30 min. After cooling EtOAc was added and the organic phase separated and washed with brine, dried (MgSO$_4$), filtered and concentrated to give 5-methyl 1,3-indanedione as a yellow solid (3.7 g, 22% yield)

Step a:

To a solution of 5-methyl indan-1,3-dione (A) (410 mg, 2.6 mmol) in EtOH (13 mL) was added 3,4-dichlorobenzaldehyde (B) (493 mg, 2.8 mmol) followed by piperidine (1 drops). The reaction mixture was heated at reflux for 30 min. After cooling, to the reaction mixture was added aqueous hydrogen peroxide (30%, 0.87 mL, 7.7 mmol) and DBU (97 mg, 0.6 mmol). Stirring was continued for 30 min. then hexane (5 mL) was added and the precipitate was filtered. The resulting solid was triturated twice with a mixture of propanol/hexane (1/1) and dried under high vacuum to give 3-(3,4-dichlorophenyl)-spiro (oxirane-2,2'-[5-Methyl-indan])-1',3'-dione (D) (701 mg, 82% yield).

Step c:

A mixture of 3-(3,4-dichlorophenyl)-spiro (oxirane-2,2'-[5-Methyl-indan])-1',3'-dione (D) (200 mg, 0.8 mmol) and 1-(4-[1,2,3]thiazol-4yl-phenyl)-pyrrole-2,5-dione (e) (155 mg, 0.6 mmol) in toluene (4.6 mL) was heated to reflux for 16 h. After cooling and concentration, the residue was triturated with EtOAc to give a mixture of two compounds F/G (racemic cis/cis isomers, 228 mg, 60% yield)

Step d:

To a solution of compounds F/G (210 mg, 0.36 mmol) in CH$_3$CN (36 mL) was added NaOH (0.02N, 17.8 mL, 0.36 mmol) using a syringe pump over 1 h. After the addition was completed, the reaction mixture was stirred for an extra 1 h. The solution was then lyophilized to give a mixture of racemic compounds J/K (227 mg, quantitative yield). Pure enantiomer L was obtained via separation on preparative HPLC using a chiral column (Chiracel OD, isocratic eluent 65% CH$_3$CN/H$_2$O containing 0.06% TFA; UV lamp at 205 nm; flow 7 mL/min.). The desired fractions were combined and lyophilized. The corresponding sodium salt was prepared by treatment with NaOH (0.02N, 1 equiv.) in acetonitrile followed by lyophilization to give the sodium salts (15 mg) as white solid. L: $^1$H-NMR (400 MHz, DMSO-d$_6$) δ 10.35 (s, 1H), 8.40 (d, J=8.6 Hz, 2H), 7.89–7.80 (m, 3H), 7.64 (m, 3H), 7.52 (d, J=8.3 Hz, 1H), 7.51–7.34 (m, 1H), 5.75 (s, 1H), 4.19 (m, 1H), 3.78 (m, 1H), 2.57 (s, 3H); ES MS m/z 606 (MH+).

The inhibitory activity of the compound was assessed according to the enzymatic assays described in Example 6 and was determined to have an IC$_{50}$ of 180 nM. Selectivity of the inhibitor was verified by lack of activity (or lower potency) in the SV40 large T antigen assay as described in Example 7.

Example 3

E2 TAD-Inhibitor Complex Formation

Inhibitor L powder was solubilized in 100% DMSO at a concentration of 60 mM. The protein solution consisted of 10 mg/ml E2TAD in purification buffer (25 mM Tris-HCl pH to 8.0, 500 mM NaCl, 5 mM TCEP, 0.1 mM EDTA). The complex of E2TAD-L was made by mixing 1 μl of inhibitor L in 74 μL of protein solution. The solution was kept at 4° C. for 2–3 hours before the crystallization experiments were performed.

Example 4

Crystallization and Data Collection

Crystallization of the apo-E2 TAD and complex E2TAD-L were carried out using the hanging drop vapor diffusion technique (A. McPherson, Preparation and Analysis of Protein Crystals, Krieger Pub. 1989) in VDX crystallization plates (Hamton Research, Laguna Niguel, Calif.).

In particular for the apo HPV-11 E2 TAD: 1 μL of the Se-E2 TAD solution (5 mg/ml in purification buffer) was mixed with 1 μL of a solution made of 0.1M Na succinate pH 5.0, 18% PEG5000 mme and 0.2M ammonium sulfate. The resulting 2 μL drop was suspended above a 1 ml reservoir solution made of 0.1M Na succinate pH5.0, 18% PEG5000 mme and 0.2M ammonium sulfate. The crystals obtained at 4° C. belong to space group C222 with unit cell dimension of a=54.9 Å, b=169.9 Å and c=46.1 Å and contained one molecule per asymmetric unit Diffraction data were collected on beamline X4a (NSLS, Brookhaven National Laboratory, New York). Four data sets were collected form a single crystal cooled at 100 K, at four different x-ray wavelengths near the selenium absorption edge (0.9790 Å, 0.9794 Å, 0.9743 Å, and 0.9879 Å). Images were collected on a ADSC Q4 CCD, the maximum resolution was 2.4 Å.

For crystallization of the complex: 1 μL of the complex solution, as described in example 3, was mixed with 1 μL of a solution made of 0.1M MES pH 5.5 and 35% MPD (methyl pentane diol). The resulting drop was suspended above a 1 mL reservoir solution made of 0.1M MES pH 5.5, 35% MPD. Plates were then stored at 4 C. The crystals obtained belong to space group P4(1) with unit cell dimension of a=b=60.7 Å and c=82.5 Å and contain one molecule per asymmetric unit.

Initial diffraction data were measured using a home source x-ray generator (Rigaku, Japan) equipped with an R-axis II image plate area detector (Molecular Structure Corp, Texas). Data to a resolution of 3.15 Å were collected on a single crystal of the complex cooled at 100 K.

High resolution diffraction data were then collected on beamline X25 (NSLS, Brookhaven National Laboratory, New York). Diffraction image were collected on a Brandeis B4 detector (Brandeis University) mounted on a kappa-axis goniometer (Enraf-Nonius, The Netherlands). A full data set to a resolution of 2.4 Å was collected on a single crystal of the complex cooled at 100 K (presented in FIG. 9).

Example 5

Phasing, Model Building and Refinement

Phasing of the apo crystal data was done by MAD (Multi wavelength Anomalous Dispersion) using the program MLPHARE (Collaborative Computational Project, number4, 1994, the CCP4 suite: programs for Protein Crystallography, Acta Cryst. D50, 760–763).

For the complex crystal, Molecular Replacement (MR) method was used for initial estimation of diffraction data phases. The apo structure of Se-E2TAD was used as a model. A rotation and translation search were done using the program AMORE (Collaborative Computational Project, number4, 1994, the CCP4 suite: programs for Protein Crystallography, Acta Cryst. D50, 760–763).

Model building into electron density map was carried out with the software O (Alwyn Jones, Upsala University, Sweden) and model refinement was done with software CNX (Molecular Simulation Inc, San Diego, Calif.). The new model was then improved by a cycling procedure including electron-density map calculation, model rebuilding and model refinement steps. The final model included residues 2 to 196 of E2TAD and two inhibitor L molecules. The latest crystallographic R factor was 24.6% and $R_{free}$ factor is 29.3%.

Example 6

E2-Dependent E1 Origin-Binding Assay

This assay was modeled on a similar assay for SV40 T Antigen described by McKay (J. Mol. Biol., 1981,145:471). A 400 bp radiolabeled DNA probe, containing the HPV-11 origin of replication (Chiang et al., 1992, Proc. Natl. Acad. Sci. USA 89:5799) was produced by PCR, using plasmid pBluescript™ SK encoding the origin (nucleotides 7886-61 of the HPV-11 genome in unique BAMH1 site) as template and primers flanking the origin. Radiolabel was incorporated as [$^{33}$P]dCTP. Binding assay buffer consisted of: 20 mM Tris pH 7.6, 100 mM NaCl, 1 mM DTT, 1 mM EDTA.

Other reagents used were protein A-SPA beads (type II, Amersham) and K72 rabbit polyclonal antiserum, raised against a peptide corresponding to the C-terminal 14 amino acids of HPV-11 E1. Following the protocol from Amersham, one bottle of beads was mixed with 25 mL of binding assay buffer. For the assay, a saturating amount of K72 antiserum was added to the beads and the mixture was incubated for 1 h, washed with one volume of binding assay buffer, and then resuspended in the same volume of fresh binding assay buffer. Binding reactions contained 8 ng of E2, approximately 100–200 ng of E1-containing nuclear extract expressed from baculovirus-infected cells (as reported in WO 99/57283), and 0.4 ng of radiolabeled probe in a total of 80 μL of binding assay buffer. After 1 h at room temperature, 25 μL of K72 antibody-SPA bead suspension was added to the binding reaction and mixed. After an additional hour of incubation at room temperature, the reactions were centrifuged briefly to pellet the beads and the extent of complex formation was determined by scintillation counting on a Packard TopCount™. Typically, the signal for reactions containing E1 and E2 was 20–30 fold higher than the background observed when either E1, E2, or both was omitted.

Example 7

SV40 T Antigen-DNA Binding Assay

This assay measures the formation of an SV40 T Antigen (TAg)-origin complex. The assay was developed by R. D. G. McKay (J. Mol. Biol. (1981) 145, 471–488). In principle, it is very similar to the E2-dependent E1-DNA binding assay (Example 6), with TAg replacing E1 and E2, and a radiolabeled SV40 ori probe replacing the HPV ori probe. The assay is used as a counterscreen for the assay of Example 6, since TAg shares functional homology to E1 and E2, but has very low sequence similarity.

The radiolabeled ori-containing DNA probe was made by PCR using pCH110 plasmid (Pharmacia) as a template. This template encodes the SV40 minimal origin of replication at nucleotides 7098-7023. Primers were "sv40-6958sens"=5'-GCC CCT AAC TCC GCC CAT CCC GC (SEQ ID NO. 7), and "sv40-206anti"=5'-ACC AGA CCG CCA CGG CTT ACG GC (SEQ ID NO. 8). The PCR product was approximately 370 base pairs long and was radiolabeled using 50 μCi/100 μL PCR reaction of dCTP ($\alpha$-$^{33}$P). Subsequent to the PCR reaction, the product was purified using either the Qiagen® PCR purification kit, or a phenol extraction/ethanol precipitation procedure. The purified product was diluted to 1.5 ng/μL (estimated by gel electrophoresis) in TE. Fresh preparations had approximately 150,000 cpm/μL.

Binding reactions were performed by mixing 30 μl of TAg solution (100 ng/well, 200 ng of a $^{33}$P-radiolabeled DNA probe, and 7.5 μl of 10×DNA binding buffer (200 mM Tris-HCl pH 7.6, 100 mM NaCl, 1 mM EDTA, 10 mM DTT) in a final volume of 75 μl. Binding reactions were allowed to proceed at room temperature for 60 min. The Large T Antigen: Purchased from Chimerx, at 2.0 mg/mL.

The protein-DNA complexes were immunocaptured using an α-TAg monoclonal antibody (PAb 101, subtype IgG2a, hybridoma obtained from ATCC and antibody purified in-house) bound to protein A-SPA beads. Immunoprecipitation of protein-DNA complexes was carried out for 1 hr at room temperature. The plates were spun briefly and the precipitated radiolabeled DNA fragments were counted on a Top-Count® counter.

Discussion

Figure 5:
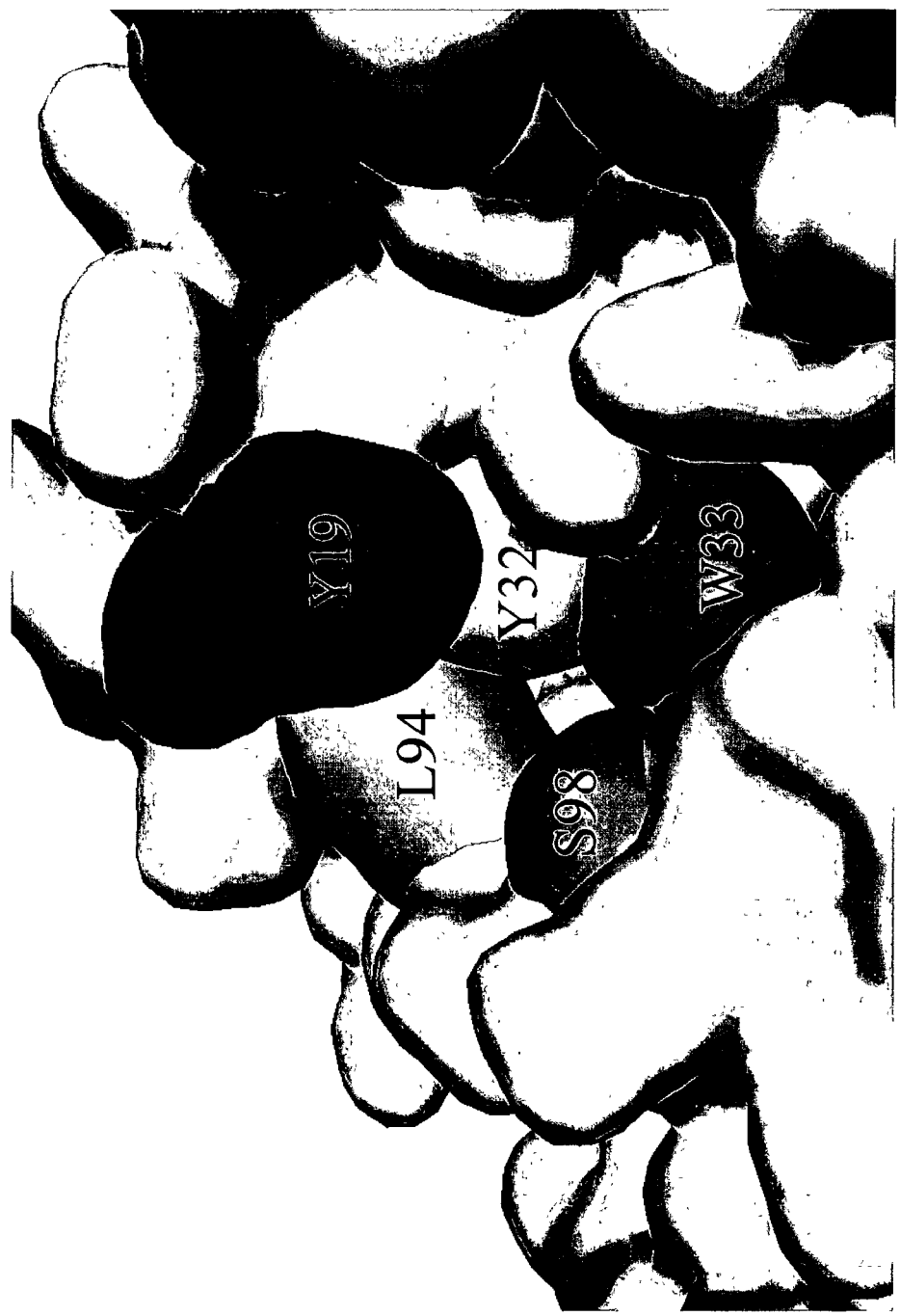

FIG. 2 shows a model of the crystal structure of E2 TAD from HPV-16 (Antson et al., 2000, Nature, (403) 805–809). A zoom view on the binding pocket region in this model, as shown in FIG. 5, reveals that amino acids Y32, W33 and L94 define a cavity that is too small to define a suitable pocket that will enable a small molecule inhibitor to bind therein, without comparable adjustments of the amino acid side chains to accommodate the inhibitor.

Figure 6:

Even when the corresponding HPV-11 E2 TAD domain is crystallized and modeled, the corresponding amino acids again reveal a cavity too small to define any sort of pocket that could be viewed as a target suitable for inhibitor-binding (FIG. 6A). As shown in FIG. 6B, the present invention for the first time, now shows that the crystal structure of the new E2 TAD-inhibitor complex provides a novel and unexpected inhibitor-binding pocket that constitutes a unique tool for identifying potential inhibitors of the HPV DNA replication process.

Surprisingly, the structure of the E2 TAD-inhibitor complex reveals that binding of inhibitor L induces a movement of the side chain of tyrosine at position 19 (FIG. 7) where the aromatic ring rotates in a significant manner out of the small cavity seen in the apo-structure, resulting in the formation of a deep cavity. The movement of the tyrosine 19 side chain gives an rms deviation for all atoms of 1.959 Å. One skilled in the art will understand that this deviation constitutes a huge movement, which could not have been predicted to occur on its own or in the presence of a small molecule inhibitor.

In addition, the imidazole ring of histidine 32 rotates by 90 degrees to accommodate the inhibitor but still remains part of the deep cavity. The movement of the histidine 32 main chain gives an rms deviation for all atoms of 0.704 Å. Neither of these two rotational movements could have been predicted to occur and result in the formation of this deep cavity within the binding pocket.

As shown in FIG. 6A, the deep cavity is defined by amino acids histidine 32, tryptophan 33, and leucine 94. The "all atoms" rmsd displacement of these three amino acids residues is 0.515 Å. Such rms can not be accounted for by the native flexibility of these residues within the context of the binding pocket. Indeed, a rms deviation of 1.0 Å is considered within normal limits in the context of a whole protein of 200 amino acids. In the present case, the rms variation for all atoms of H32, W33 and L94 between HPV-16 apo E2TAD of Antson supra and Applicant's HPV-11 apo E2TAD, is 0.212 Å. This defines the predictable (upper) limit by which these 3 residues can move in concert. The present invention is outside that range of predictable movement for these three residues.

Figure 8:

Serine 98 is not on the same plane as H32, W33 and L94 and forms part of a shallower portion that may also be used for generating models of a larger pocket comprising a deep cavity formed by the H32, W33 and L94 and a shallow cavity defined by one or more amino acids selected from: L15, I36, E39, K68, N71, A72, S98 and Y99 (see FIG. 8).

FIG. 9 lists the X-ray coordinates of the protein-inhibitor complex which can be used for modeling purposes. Apparent from these coordinates is the fact that the complex obtained by the Applicant contains two molecules of inhibitor, however the model revealed that the second inhibitor resides outside the deep cavity and does not interact with the protein in a significant manner. Also, the following amino acids are modeled as Alanine due to their high flexibility that renders them invisible to x-ray: E2, K107, K173, S180, M182, H183 and P196.

According to Harris & Botchan, 1999 (Science, 284 (5420); 1673), various E2 proteins average only 30% amino acid sequence identity. However, mutational analysis suggest that various E2 TADs share a common fold and mechanism of action. In keeping with this last statement, the amino acid clusters defining the inhibitor-binding pocket identified by the Applicant possess a surprising amount of identity/similarity, even between low-risk and high-risk HPVs (FIG. 10). The first cluster identified comprises the side chain of amino acid Y19 that moves away from the pocket region thereby opening up the deep cavity. This amino acid is highly conserved among various types of HPV having 100% identity between HPV-6, 11, 16, and 18. The second cluster comprises histidine 32 and tryptophan 33 that define the deep cavity of the pocket. Histidine 32 is identical between HPV-6 and -11 and has strong similarity between low-risk and high-risk HPV, whereas tryptophan 33 is 100% identical amongst the four types. Finally, the fourth cluster comprises Leucine 94 that also define the deep cavity of the pocket and is 100% conserved between the 4 HPV types.

When defining the bottom of the deep pocket, H29 is identical among HPV-6, -11 and -16 and is similar in HPV-18. Similarly, T97 is identical among HPV-6, -11 and -18 and is similar in HPV-16.

When defining the shallow cavity of the pocket, amino acid L15 is part of the first cluster identified and is highly similar between the low risk and high risk HPV. Within the second cluster, I36 is also highly similar whereas E39 is highly conserved amongst all 4 types. A third cluster is identified that lines the shallow cavity of the binding pocket wherein K68 and N72 are both highly conserved throughout the types. Finally, N71 is identical between HPV-6 and 11 and is similar with the high risk types. The shallow pocket further comprises amino acids of the fourth cluster such as S98 and Y99 that are also highly similar among the different types of HPV.

The high degree of identity/similarity strongly indicates that this pocket as defined according to the HPV-11 E2 TAD of the invention will also be found in other types of HPV, either low risk or high risk. Presumably, inhibitors binding to this pocket, particularly the deep cavity, as modeled using the data of FIG. 9 have a strong likelihood of binding/inhibiting the E2 protein from a wide range of papilloma viruses

What is claimed is:

1. A method of identifying a potential inhibitor of a Human Papillomavirus (HPV) E2-protein comprising a deep cavity binding pocket, wherein said HPV E2-protein is selected from the group consisting of: HPV-6, HPV-11, HPV-16 and HPV-18, said method comprising the steps of:
   (a) using the atomic coordinates of FIG. 9 to generate a three-dimensional model;
   (b) identifying said binding pocket residues which comprises at least residues His-32, Trp-33 and Leu-94, and using said residues to generate a specific three-dimensional (3-D) target;
   (c) employing said 3-D target of (b) to design or select said potential inhibitor;
   (d) synthesizing said potential inhibitor; and
   (e) contacting said potential inhibitor with said HPV E2 protein in vitro to determine the ability of said potential inhibitor to interact with said HPV E2 protein;
whereby the ability to interact is an indication that said potential inhibitor of said HPV E2 protein is identified.

2. A method of designing a compound which binds to the transactivation domain (TAD) of a HPV-11 protein comprising a deep cavity binding pocket, wherein said TAD is characterized by:
   (i) the atomic coordinates of amino acids 9-203 of SEQ ID No: 2 shown in FIG. 9 positioned within a rmsd of 1.0 Å;
   (ii) the atomic coordinates of one or more peptides selected from the group consisting of SEQ ID No: 9, 10, 11 and 18 defined three-dimensionally by performing whole body translations and/or rotations on the coordinates shown in FIG. 9; and/or
   (iii) the atomic coordinates of said deep cavity binding pocket defined by amino acids His-32, Trp-33 and Leu-94 of FIG. 9 and which are within a rmsd of 0.212 Å; said method comprising the steps of:
   (a) using the atomic coordinates of FIG. 9 to build a 3-D computer model of a compound interaction region of said protein comprising at least one of (i)–(iii);
   (b) assessing the stereochemical complementarity between a compound and said interaction region;
   (c) optimizing said stereochemical complementarity in an iterative approach by observing changes in the protein or compound that affect the protein/compound associations; and
   (d) designing a compound which optimizes said protein/compound stereochemical complementarity.

3. The method according to claim 1 or claim 2, wherein said binding pocket is further defined by one or more amino acids selected from the group consisting of: H29, T97, L15, J36, E39, K68, N71 and A72 positioned at atomic coordinates as shown in FIG. 9.

* * * * *